(12) United States Patent
LaVon et al.

(10) Patent No.: US 7,670,324 B2
(45) Date of Patent: *Mar. 2, 2010

(54) DISPOSABLE ABSORBENT ARTICLES WITH REPLACEABLE ABSORBENT CORE COMPONENTS HAVING REGIONS OF PERMEABILITY AND IMPERMEABILITY ON SAME SURFACE

(75) Inventors: Gary Dean LaVon, Liberty Township, OH (US); Theodora Beck, Colerain Township, OH (US); Gerald Alfred Young, Miller Township, Dearborn County, IN (US); Stephen Lebeuf Hardie, Symmes Township, OH (US); Thomas Henrich, Montgomery, OH (US); Edward John Milbrada, West Chester, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 1753 days.

This patent is subject to a terminal disclaimer.

(21) Appl. No.: 10/308,430

(22) Filed: Dec. 3, 2002

(65) Prior Publication Data

US 2003/0199844 A1 Oct. 23, 2003

Related U.S. Application Data

(63) Continuation of application No. 09/911,108, filed on Jul. 23, 2001, now Pat. No. 6,932,800, which is a continuation-in-part of application No. 09/431,322, filed on Nov. 2, 1999, now abandoned, which is a continuation of application No. 08/825,071, filed on Mar. 27, 1997, now Pat. No. 6,015,935, and a continuation-in-part of application No. 08/828,005, filed on Mar. 27, 1997, now Pat. No. 6,989,005.

(51) Int. Cl.
*A61F 13/20* (2006.01)

(52) U.S. Cl. .................. 604/385.14; 604/385.05; 604/385.09; 604/358; 604/378; 604/385.01; 604/385.24; 604/381; 604/385.101; 604/385.02; 604/385.03; 604/385.04; 604/385.08; 604/385.11; 604/385.15; 604/385.16; 604/385.201; 604/385.21; 604/385.23; 604/385.25; 604/385.28; 604/385.29; 604/385.3; 604/385.31; 604/386; 604/387; 604/389; 604/390; 604/391; 604/392; 604/393; 604/394; 604/395; 604/397; 604/398; 604/401; 604/402; 119/171; 442/412

(58) Field of Classification Search ............ 604/385.14, 604/358, 378, 385.01, 385.24, 381, 382, 604/385.101, 385.02–385.09, 385.11–385.19, 604/385.201–385.31, 386–402, 380, 383, 604/361; D24/124; 119/171; 442/412

See application file for complete search history.

(56) References Cited

U.S. PATENT DOCUMENTS

| | | |
|---|---|---|
| 833,849 A | 10/1906 | Schiff |
| 1,695,109 A | 12/1928 | Kosloff |
| 1,893,745 A | 1/1933 | Josias |
| 2,468,445 A | 4/1949 | Hurst |
| 2,476,585 A | 7/1949 | Cohen |
| 2,530,647 A | 11/1950 | Buchler |
| 2,574,279 A | 11/1951 | Oberle |
| 2,688,328 A | 9/1954 | Marcus |
| 2,695,025 A | 11/1954 | Andrews |
| 2,788,786 A | 4/1957 | Dexter |
| 2,826,199 A | 3/1958 | Brandon |
| 2,832,346 A | 4/1958 | Morstad |
| 2,842,129 A | 7/1958 | Emstorff |
| 2,868,205 A | 1/1959 | Epstein |
| 3,050,063 A | 8/1962 | Margraf |
| 3,162,196 A | 12/1964 | Salk |
| RE26,151 E | 1/1967 | Duncan et al. |
| RE26,152 E | 1/1967 | Andren |
| 3,306,293 A | 2/1967 | Marder et al. |
| 3,556,932 A | 1/1971 | Coscia et al. |
| 3,595,235 A | 7/1971 | Jespersen |
| 3,658,064 A | 4/1972 | Pociluyko |
| 3,661,875 A | 5/1972 | Sieja |
| 3,771,524 A | 11/1973 | Ralph |
| 3,848,594 A | 11/1974 | Buell |
| 3,860,003 A | 1/1975 | Buell |

| | | | | | | |
|---|---|---|---|---|---|---|
| 3,886,941 | A | 6/1975 | Duane et al. | 5,147,345 A | 9/1992 | Young et al. |
| 3,911,173 | A | 10/1975 | Sprague, Jr. | 5,149,335 A | 9/1992 | Kellenberger et al. |
| 3,918,433 | A | 11/1975 | Fuisz | 5,167,655 A | 12/1992 | McCoy |
| 3,926,189 | A | 12/1975 | Taylor | 5,176,668 A | 1/1993 | Bernardin |
| 4,019,517 | A | 4/1977 | Glassman | 5,188,624 A | 2/1993 | Young, Sr. et al. |
| 4,022,210 | A | 5/1977 | Glassman | 5,207,662 A | 5/1993 | James |
| 4,062,817 | A | 12/1977 | Westerman | 5,207,663 A * | 5/1993 | McQueen ............... 604/385.05 |
| 4,072,150 | A | 2/1978 | Glassman | 5,217,445 A | 6/1993 | Young et al. |
| 4,076,663 | A | 2/1978 | Masuda et al. | 5,236,428 A * | 8/1993 | Zajaczkowski ......... 604/385.26 |
| 4,081,301 | A | 3/1978 | Buell | 5,260,345 A | 11/1993 | DesMarais et al. |
| 4,093,776 | A | 6/1978 | Aoki et al. | 5,268,224 A | 12/1993 | DesMarais et al. |
| 4,257,418 | A | 3/1981 | Hessner | 5,318,554 A | 6/1994 | Young et al. |
| 4,260,443 | A | 4/1981 | Lindsay et al. | 5,324,561 A | 6/1994 | Rezai et al. |
| 4,265,245 | A | 5/1981 | Glassman | 5,325,543 A | 7/1994 | Allen |
| 4,326,302 | A | 4/1982 | Lowe et al. | 5,358,500 A | 10/1994 | LaVon et al. |
| 4,467,012 | A | 8/1984 | Pedersen et al. | 5,360,419 A | 11/1994 | Chen et al. |
| 4,496,360 | A | 1/1985 | Joffe et al. | 5,360,422 A * | 11/1994 | Brownlee et al. ....... 604/385.15 |
| 4,515,595 | A | 5/1985 | Kievit et al. | 5,383,867 A | 1/1995 | Klinger |
| 4,560,381 | A | 12/1985 | Southwell | 5,387,207 A | 2/1995 | Dyer et al. |
| 4,573,986 | A | 3/1986 | Minetola et al. | 5,401,266 A | 3/1995 | Runeman et al. |
| 4,578,073 | A | 3/1986 | Dysart et al. | 5,405,342 A * | 4/1995 | Roessler et al. ............. 604/364 |
| 4,597,760 | A | 7/1986 | Buell | 5,409,476 A | 4/1995 | Coates |
| 4,597,761 | A | 7/1986 | Buell | 5,458,591 A | 10/1995 | Roessler et al. |
| 4,605,403 | A | 8/1986 | Tucker | 5,476,457 A | 12/1995 | Roessler et al. |
| 4,610,678 | A | 9/1986 | Weisman et al. | 5,486,168 A | 1/1996 | Runeman et al. |
| 4,615,695 | A | 10/1986 | Cooper | 5,531,728 A | 7/1996 | Lash |
| 4,625,001 | A | 11/1986 | Tsubakimoto et al. | 5,549,589 A | 8/1996 | Horney et al. |
| 4,654,039 | A | 3/1987 | Brandt et al. | 5,550,167 A | 8/1996 | DesMarais |
| 4,666,983 | A | 5/1987 | Tsubakimoto et al. | 5,556,393 A | 9/1996 | Rönnberg |
| 4,695,278 | A | 9/1987 | Lawson | 5,562,646 A | 10/1996 | Goldman et al. |
| 4,699,619 | A | 10/1987 | Bernardin | 5,563,179 A | 10/1996 | Stone et al. |
| 4,710,188 | A | 12/1987 | Runeman | 5,569,229 A | 10/1996 | Rogers |
| 4,715,918 | A | 12/1987 | Lang | 5,599,335 A | 2/1997 | Goldman et al. |
| 4,734,478 | A | 3/1988 | Tsubakimoto et al. | 5,613,959 A * | 3/1997 | Roessler et al. ............. 604/364 |
| 4,756,709 | A | 7/1988 | Stevens | 5,636,387 A | 6/1997 | Lundy |
| 4,770,656 | A | 9/1988 | Proxmire et al. | 5,650,222 A | 7/1997 | DesMarais et al. |
| 4,773,903 | A | 9/1988 | Weisman et al. | 5,667,503 A | 9/1997 | Roe et al. |
| D298,566 | S | 11/1988 | Runeman | 5,778,110 A | 7/1998 | Furuya |
| 4,785,996 | A | 11/1988 | Ziecker et al. | 5,800,416 A | 9/1998 | Seger et al. |
| 4,808,178 | A | 2/1989 | Aziz et al. | 5,817,081 A | 10/1998 | LaVon et al. |
| 4,816,025 | A | 3/1989 | Foreman | 5,827,253 A | 10/1998 | Young et al. |
| 4,822,453 | A | 4/1989 | Dean et al. | 5,843,055 A | 12/1998 | Seger |
| 4,826,499 | A | 5/1989 | Ahr | 5,843,065 A | 12/1998 | Wyant |
| 4,834,736 | A | 5/1989 | Boland et al. | 5,853,404 A * | 12/1998 | Schmitz ....................... 604/386 |
| 4,834,737 | A * | 5/1989 | Khan .................... 604/385.14 | 5,906,602 A | 5/1999 | Weber et al. |
| 4,834,738 | A | 5/1989 | Kielpikowski et al. | 5,910,137 A * | 6/1999 | Clark et al. .................. 604/387 |
| 4,842,666 | A | 6/1989 | Werenicz | 5,941,863 A | 8/1999 | Guidotti et al. |
| 4,851,069 | A | 7/1989 | Packard et al. | 6,015,935 A | 1/2000 | LaVon et al. |
| 4,872,871 | A | 10/1989 | Proxmire et al. | 6,083,210 A | 7/2000 | Young et al. |
| 4,888,093 | A | 12/1989 | Dean et al. | 6,229,061 B1 | 5/2001 | Dragoo et al. |
| 4,892,598 | A | 1/1990 | Stevens et al. | 6,336,923 B1 | 1/2002 | Fujioka et al. |
| 4,898,642 | A | 2/1990 | Moore et al. | 6,443,932 B1* | 9/2002 | Maggiulli ............... 604/385.01 |
| 4,923,454 | A | 5/1990 | Seymour et al. | 6,443,933 B1 | 9/2002 | Suzuki et al. |
| 4,938,756 | A | 7/1990 | Salek | 6,623,466 B1 | 9/2003 | Richardson |
| 4,950,264 | A | 8/1990 | Osborn, III | 6,689,114 B2 | 2/2004 | Bouchard et al. |
| 4,961,736 | A * | 10/1990 | McCloud ................ 604/385.15 | 6,793,649 B1 | 9/2004 | Fujioka et al. |
| 4,964,857 | A | 10/1990 | Osborn | 6,932,800 B2* | 8/2005 | LaVon et al. ........... 604/385.14 |
| 4,964,860 | A | 10/1990 | Gipson et al. | 6,989,005 B1* | 1/2006 | LaVon et al. ........... 604/385.14 |
| 4,968,312 | A | 11/1990 | Khan | 6,989,006 B2* | 1/2006 | Lavon et al. ........... 604/385.14 |
| 4,988,344 | A | 1/1991 | Reising et al. | 7,175,613 B2 | 2/2007 | Sugiyama et al. |
| 4,988,345 | A | 1/1991 | Reising | 7,291,137 B2* | 11/2007 | LaVon et al. ........... 604/385.14 |
| 4,994,037 | A | 2/1991 | Bernardin | 2002/0013566 A1 | 1/2002 | Chappell et al. |
| 5,009,650 | A | 4/1991 | Bernardin | 2002/0058921 A1 | 5/2002 | Sigl |
| 5,009,653 | A | 4/1991 | Osborn, III | 2002/0091368 A1 | 7/2002 | LaVon et al. |
| 5,019,068 | A | 5/1991 | Perez et al. | 2002/0112982 A1 | 8/2002 | Stagray et al. |
| 5,061,259 | A | 10/1991 | Goldman et al. | 2002/0143311 A1 | 10/2002 | Brisebois |
| 5,069,672 | A * | 12/1991 | Wippler et al. ......... 604/385.14 | 2002/0143316 A1 | 10/2002 | Sherrod et al. |
| 5,098,423 | A | 3/1992 | Pieniak et al. | 2002/0165515 A1* | 11/2002 | Burnham ............... 604/385.14 |
| 5,102,597 | A | 4/1992 | Roe et al. | 2003/0220623 A1 | 11/2003 | Sugiyama et al. |
| 5,108,385 | A * | 4/1992 | Snyder ....................... 604/397 | 2004/0024379 A1 | 2/2004 | LaVon et al. |
| 5,128,082 | A | 7/1992 | Makoui | 2004/0030314 A1 | 2/2004 | LaVon et al. |
| 5,137,537 | A | 8/1992 | Herron et al. | 2004/0039361 A1 | 2/2004 | LaVon et al. |
| 5,141,505 | A | 8/1992 | Barrett | | | |

FOREIGN PATENT DOCUMENTS

| | | | |
|---|---|---|---|
| CN | 2073744 U | | 3/1991 |
| EP | 0 319 314 A2 | | 6/1989 |
| EP | 0549988 A1 | * | 7/1993 |
| EP | 0919213 A2 | * | 6/1999 |
| GB | 493819 | | 10/1938 |
| GB | 734994 | | 8/1955 |
| GB | 1411087 | | 10/1975 |
| GB | 2042342 | | 9/1980 |
| GB | 2042342 A | * | 9/1980 |
| GB | 2 269 998 | | 3/1994 |
| GB | 2295321 | | 5/1996 |
| JP | 1993-86314 | | 11/1993 |
| JP | 6121812 | | 5/1994 |
| WO | WO 89/11843 | | 12/1989 |
| WO | WO 91/10413 | | 7/1991 |
| WO | WO 91/16871 | | 11/1991 |
| WO | WO 9210984 A1 | * | 7/1992 |
| WO | WO 94/24973 | | 11/1994 |
| WO | WO 95/17870 | | 7/1995 |
| WO | WO 01/60300 A1 | | 8/2001 |

OTHER PUBLICATIONS

U.S. Appl. No. 11/143,691, filed Jun. 2, 2005, All Offices Actions and Responses, beginning Jun. 2, 2005.
U.S. Appl. No. 10/410,782, filed Apr. 9, 2003, All Office Actions and Responses, Apr. 9, 2003 through Oct. 17, 2007 (now U.S. Patent 7,291,137).
U.S. Appl. No. 10/410,783, filed Apr. 9, 2003, All Office Actions and Reponses, beginning Apr. 9, 2003.
U.S. Appl. No. 11/430,367, filed May 9, 2006, All Office Actions and Responses, beginning May 9, 2006.
U.S. Appl. No. 11/430,388, filed May 9, 2006, All Office Actions and Responses, beginning May 9, 2006.
U.S. Appl. No. 11/430,744, filed May 9, 2006, All Office Actions and Responses, beginning May 9, 2006.
U.S. Appl. No. 11/430,569, filed May 9, 2006, All Office Actions and Responses, beginning May 9, 2006.
U.S. Appl. No. 11/445,624, filed Jun. 2, 2006, All Office Actions and Responses, beginning Jun. 2, 2006.
U.S. Appl. No. 11/446,460, filed Jun. 2, 2006, All Office Actions and Responses, begining Jun. 2, 2006.
U.S. Appl. No. 11/430,746, filed May 9, 2006, All Office Actions and Responses, beginning May 9, 2006.
U.S. Appl. No. 11/636,675, filed Dec. 11, 2006, All Office Actions and Responses, beginning Dec. 11, 2006.
U.S. Appl. No. 11/978,051, filed Oct. 29, 2007, All Office Actions and Responses, beginning Oct. 29, 2007.

* cited by examiner

*Primary Examiner*—Tatyana Zalukaeva
*Assistant Examiner*—Ginger T Chapman
(74) *Attorney, Agent, or Firm*—William E. Gallagher

(57) ABSTRACT

A disposable absorbent article adapted to be worn about a lower torso of a human body and having a chassis, a non-removable absorbent core component disposed in a crotch region of the chassis, and a replaceable absorbent core component disposed in capillary liquid communication with the non-removable absorbent core component and having longitudinally disposed regions of liquid permeability and liquid impermeability on the same surface. The replaceable absorbent core component may be removed and a like component may be substituted without the removal of the absorbent article from the wearer. The replaceable absorbent core component may be disposed inside an openable chassis pocket, with access for its removal and replacement provided by an aperture in a backsheet, an openable end of an external pocket, or an openable end of an internal pocket formed at an area of a waist end edge where the backsheet and a topsheet may be separated.

22 Claims, 54 Drawing Sheets

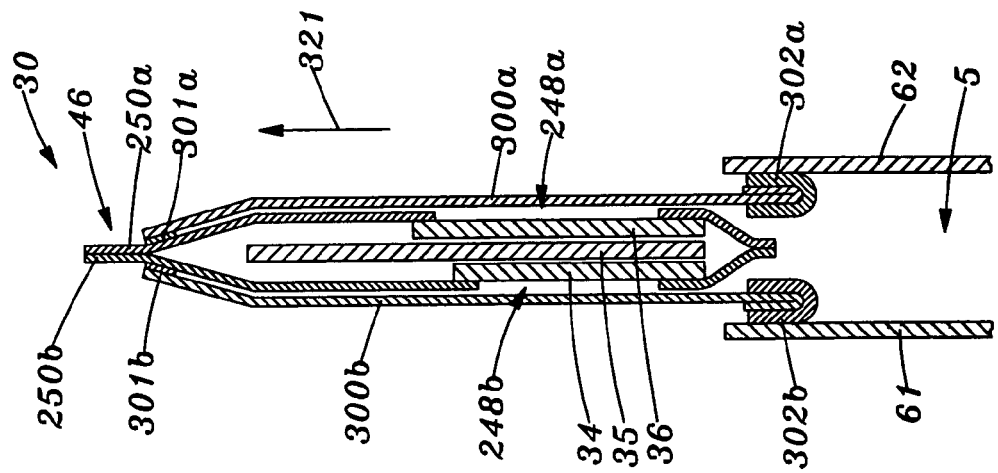
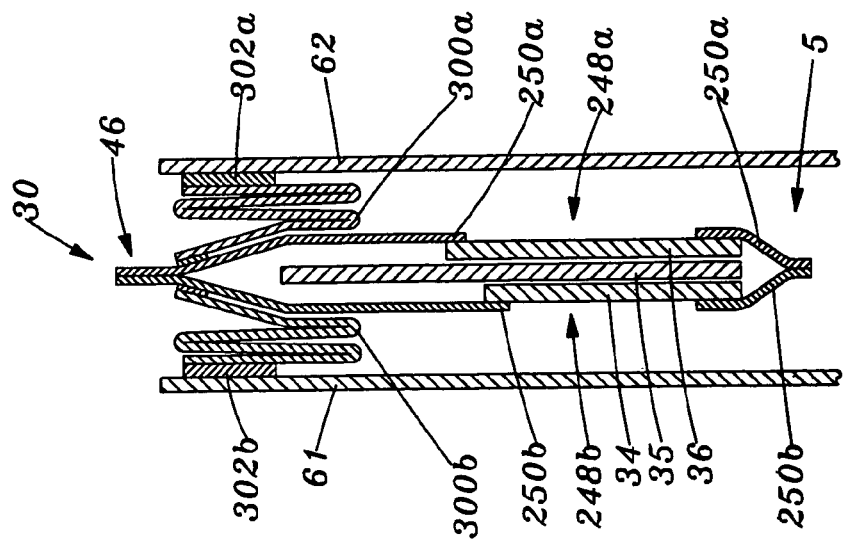

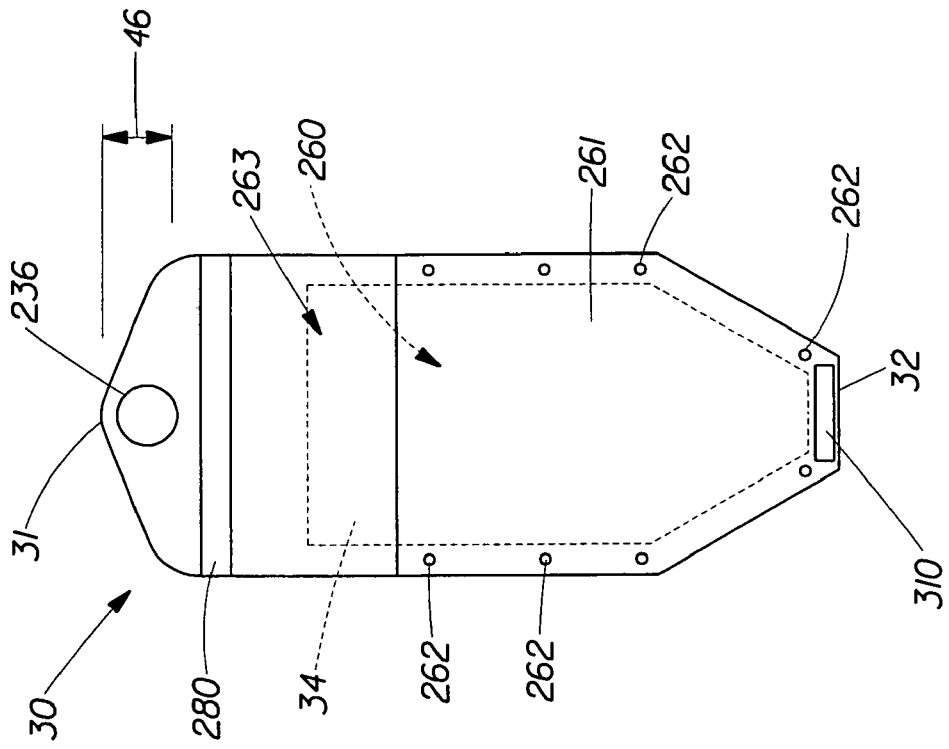
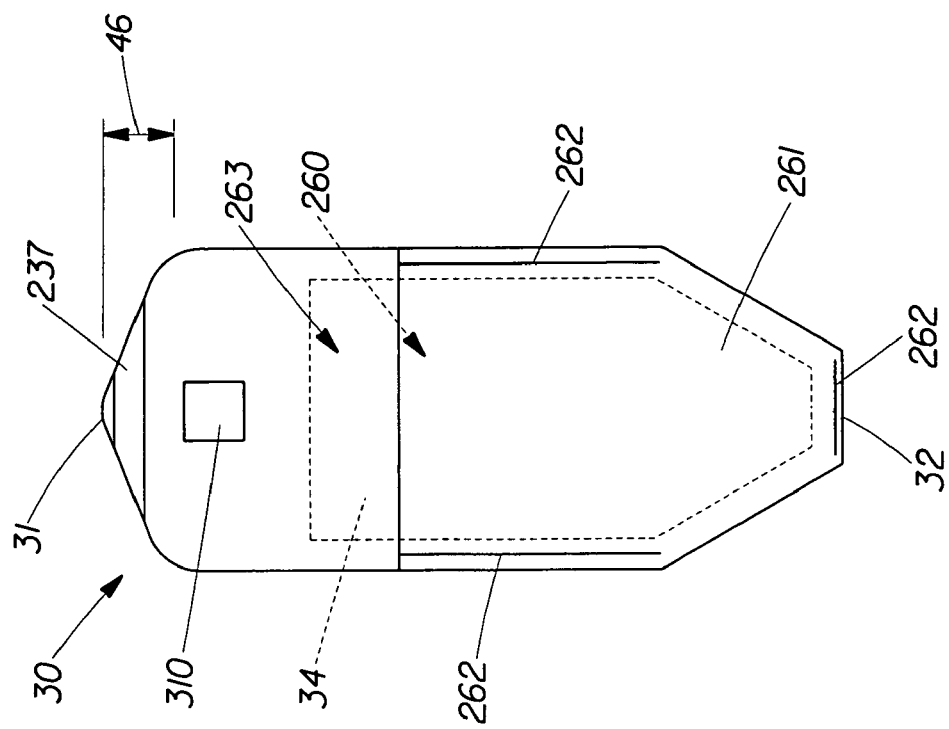

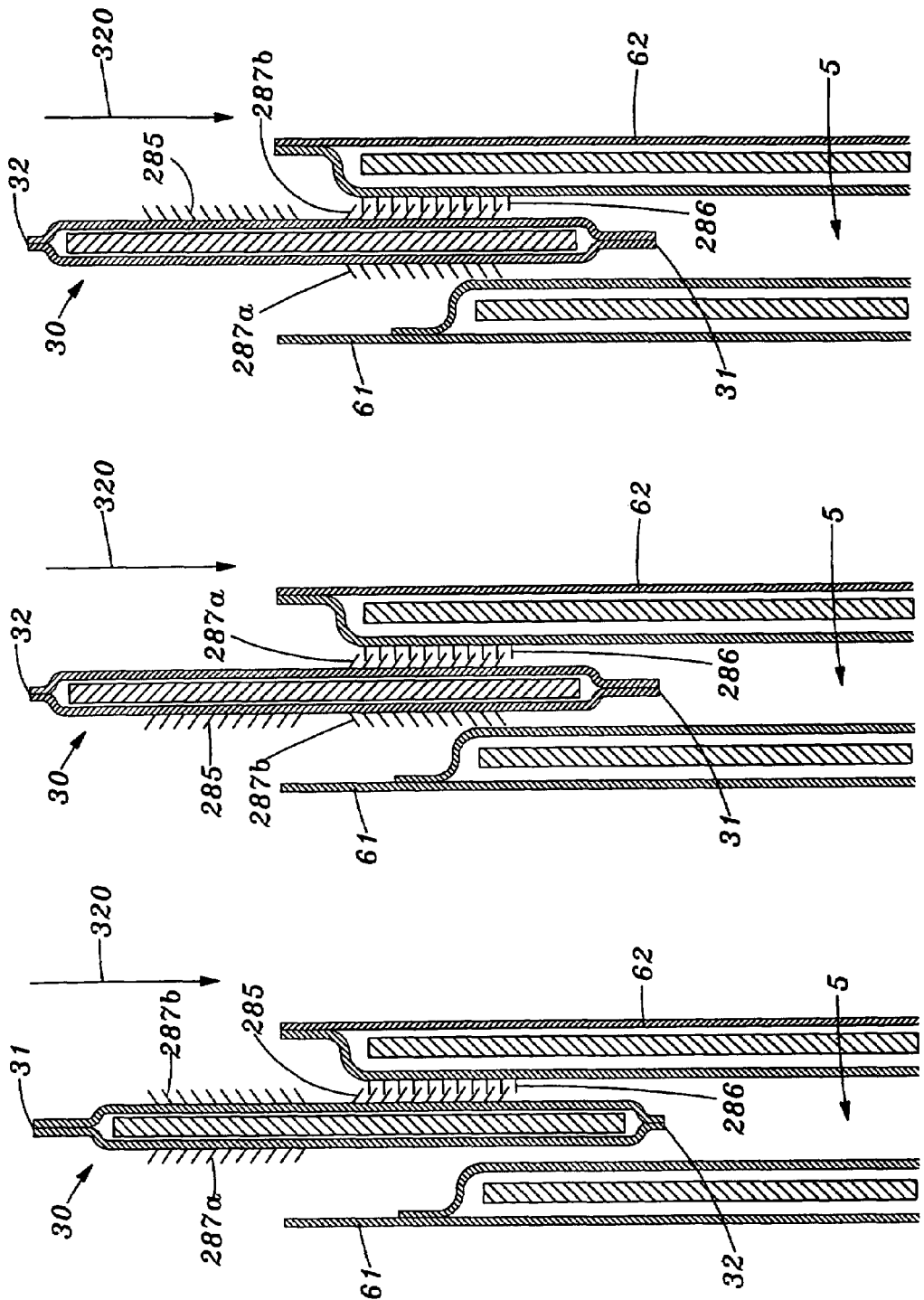

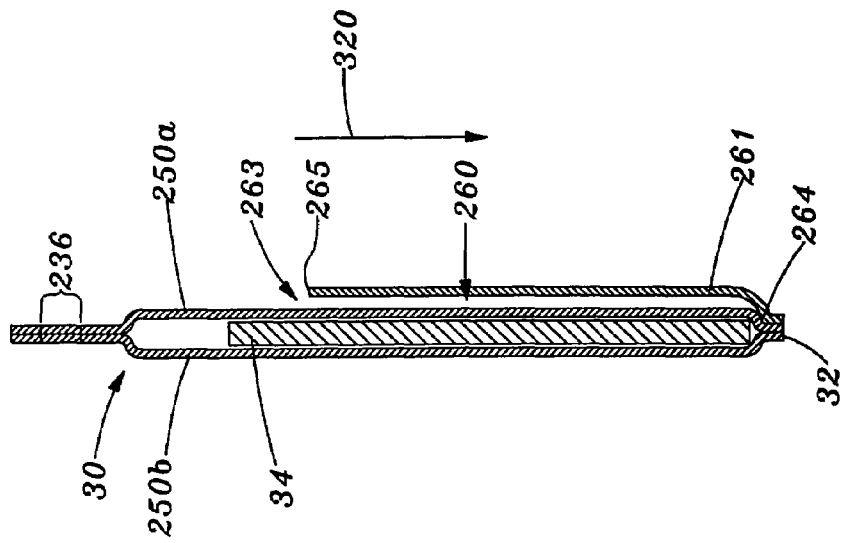
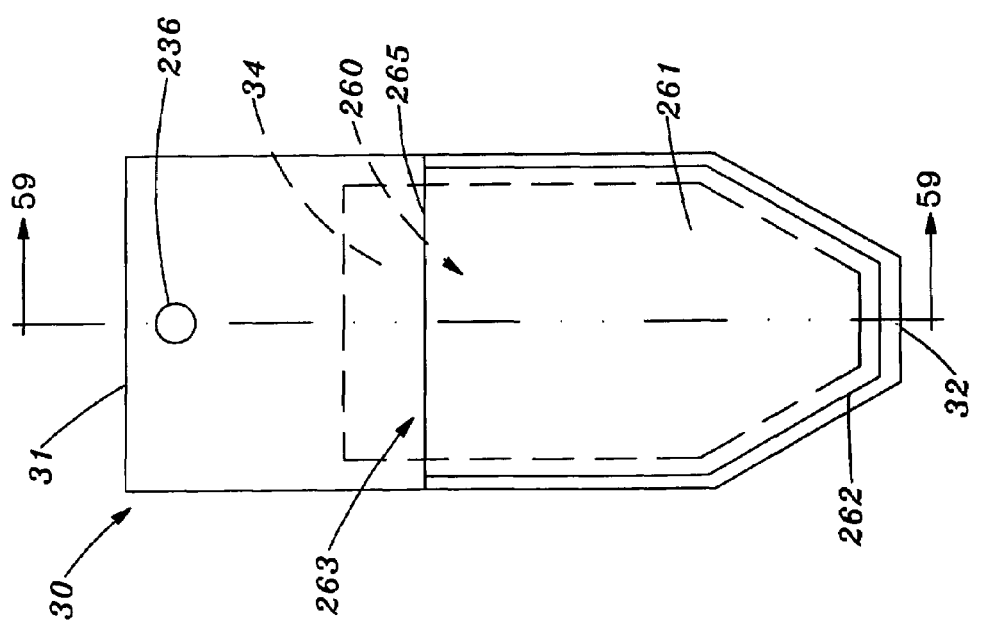
Fig. 59
Fig. 58

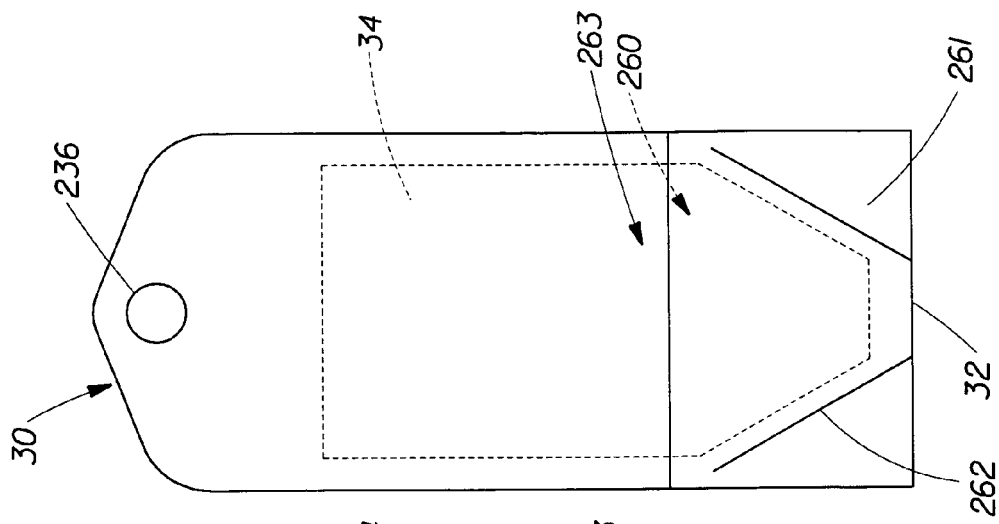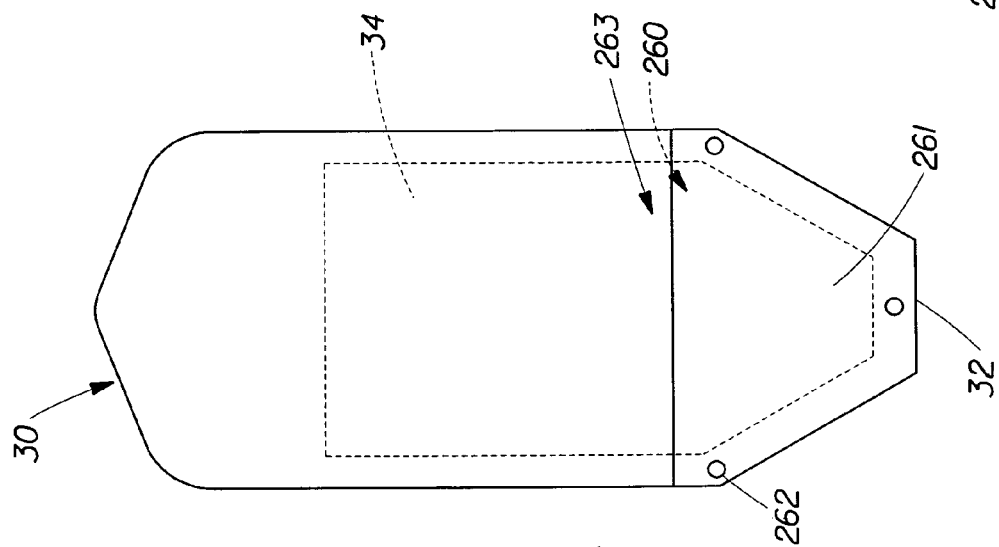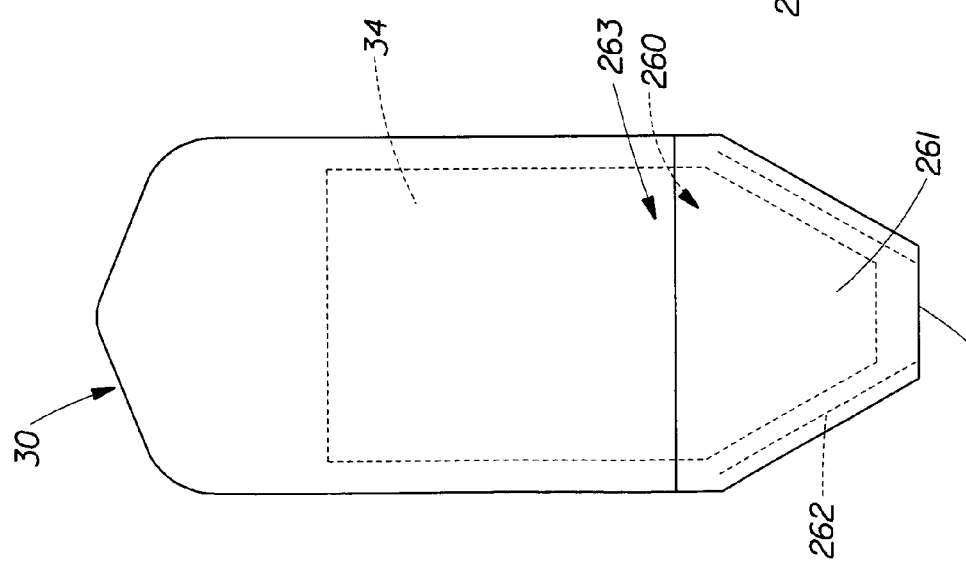

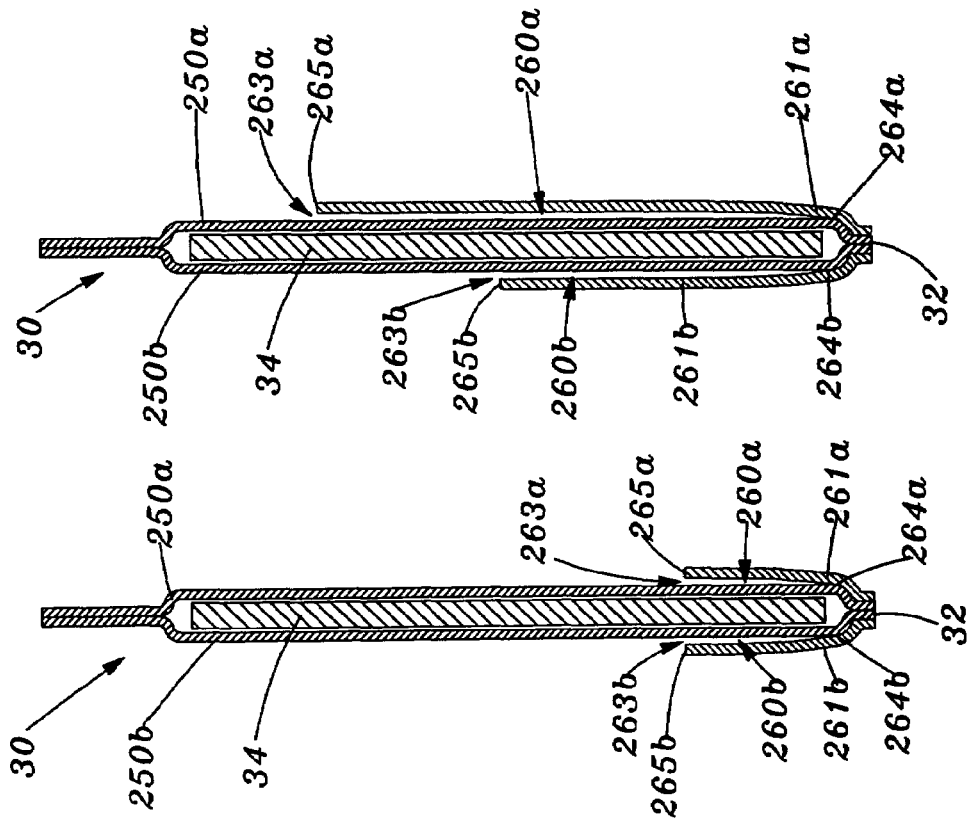
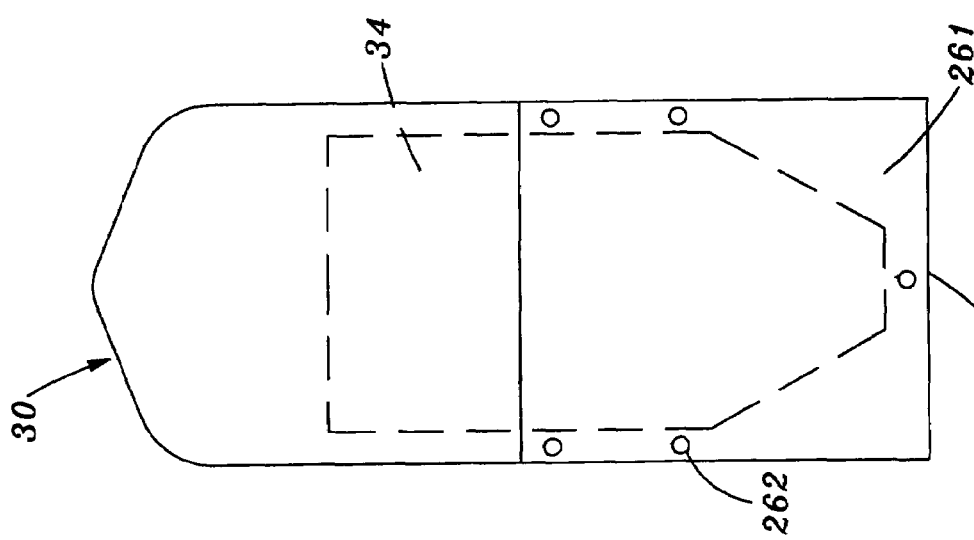
Fig. 65
Fig. 64
Fig. 63

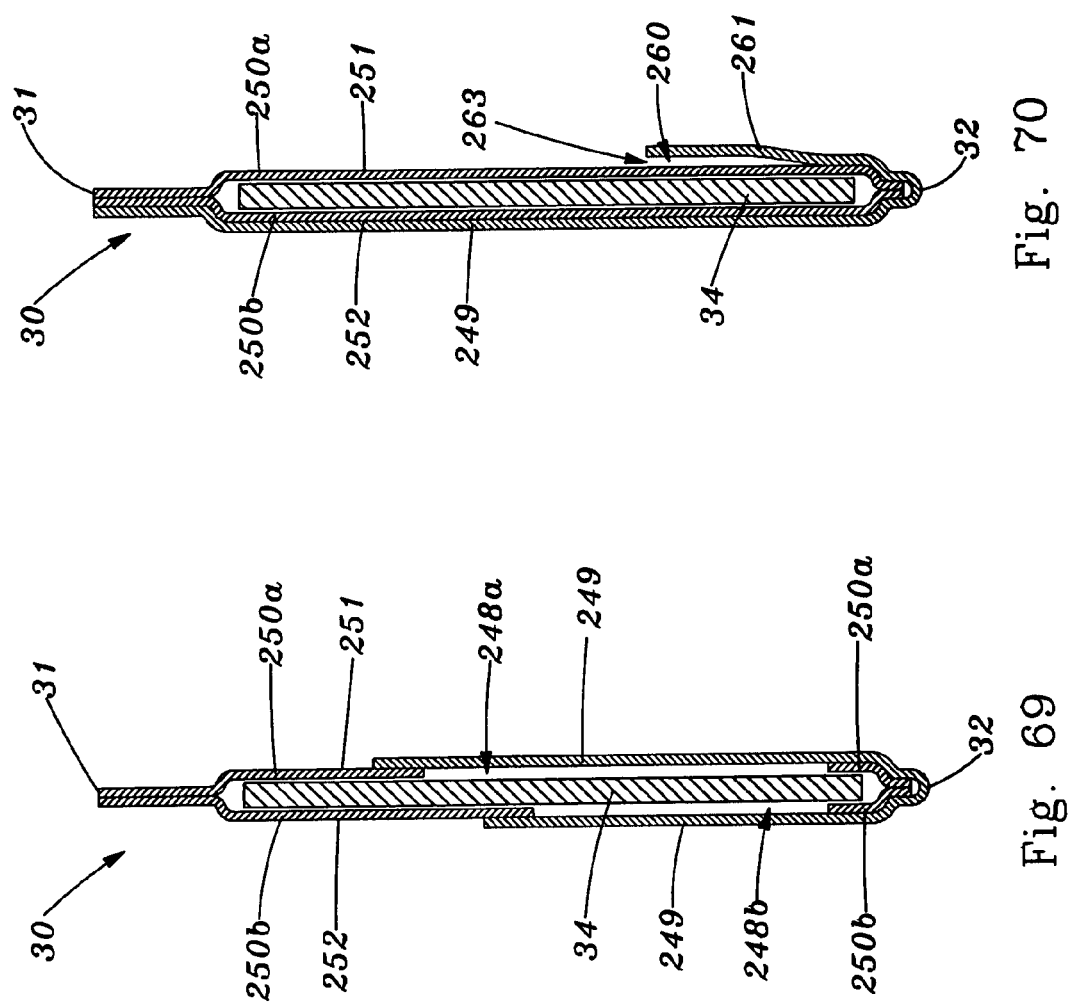

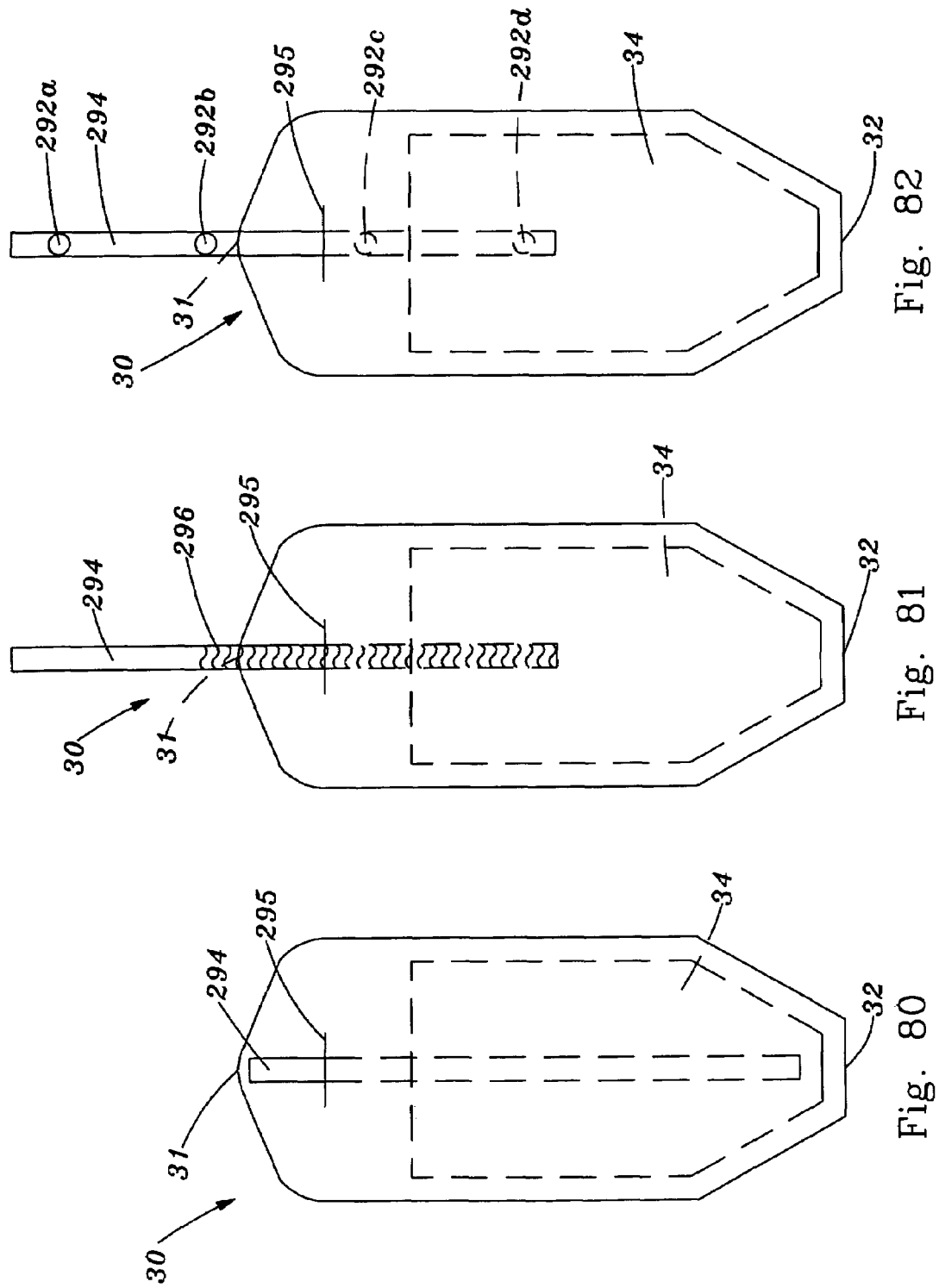

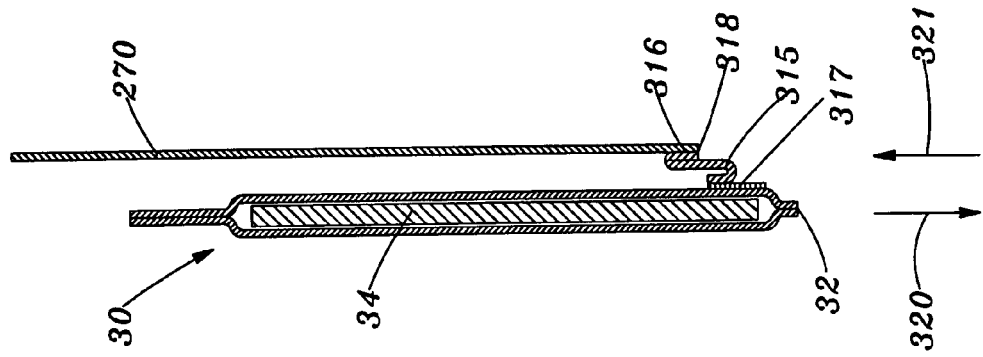
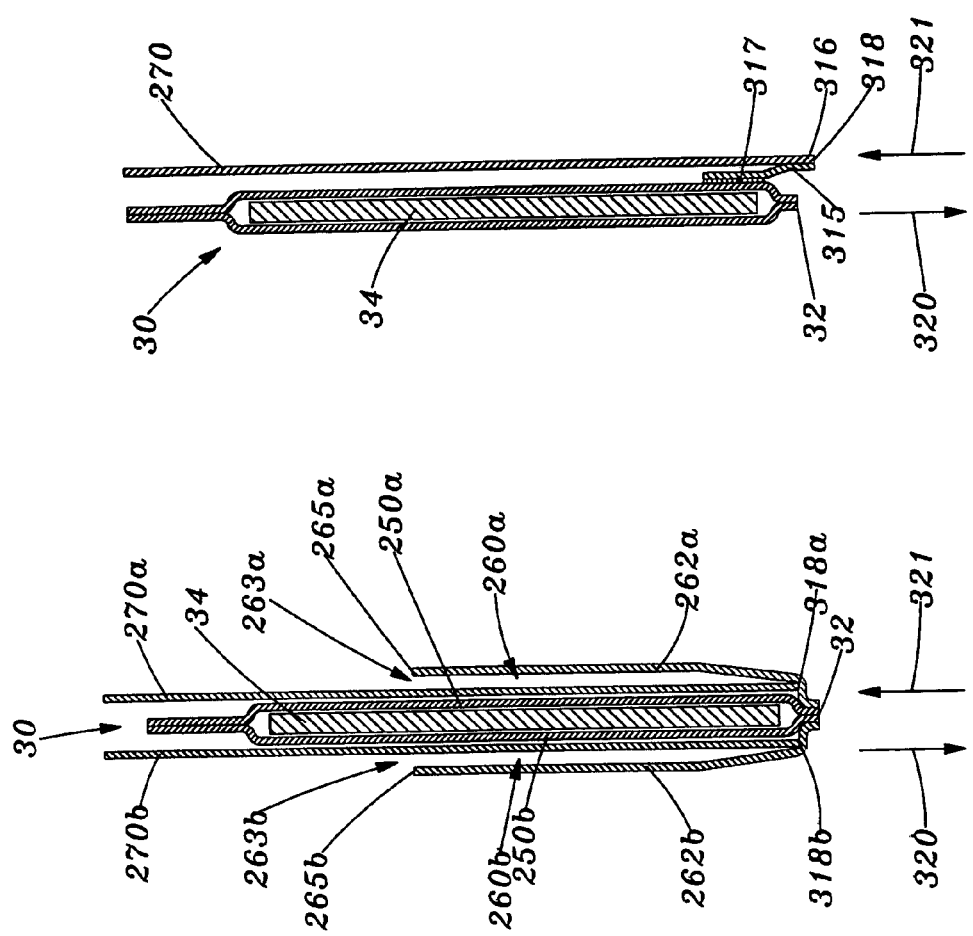

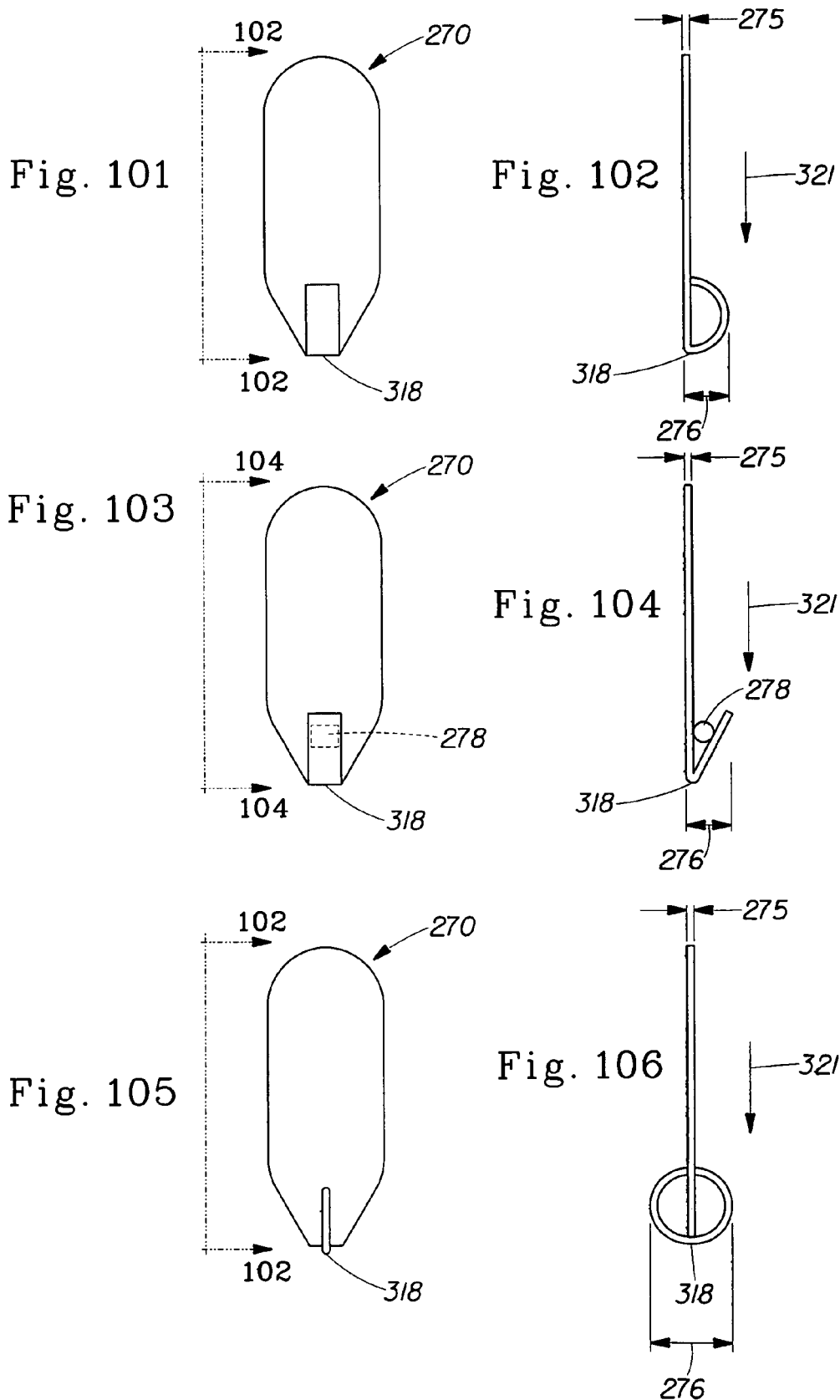

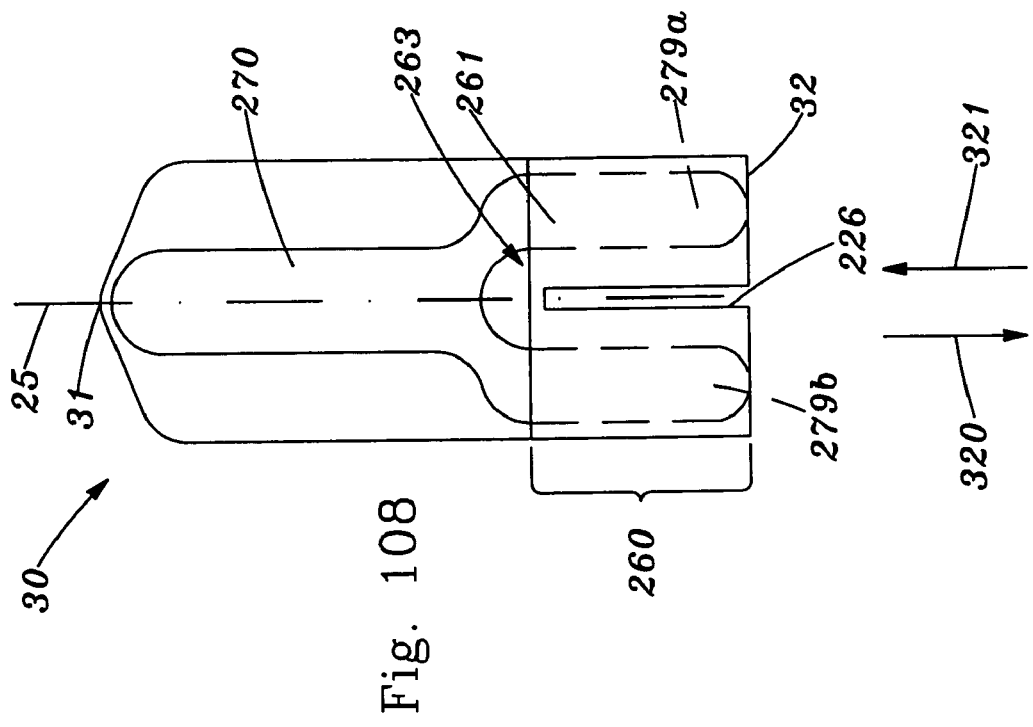
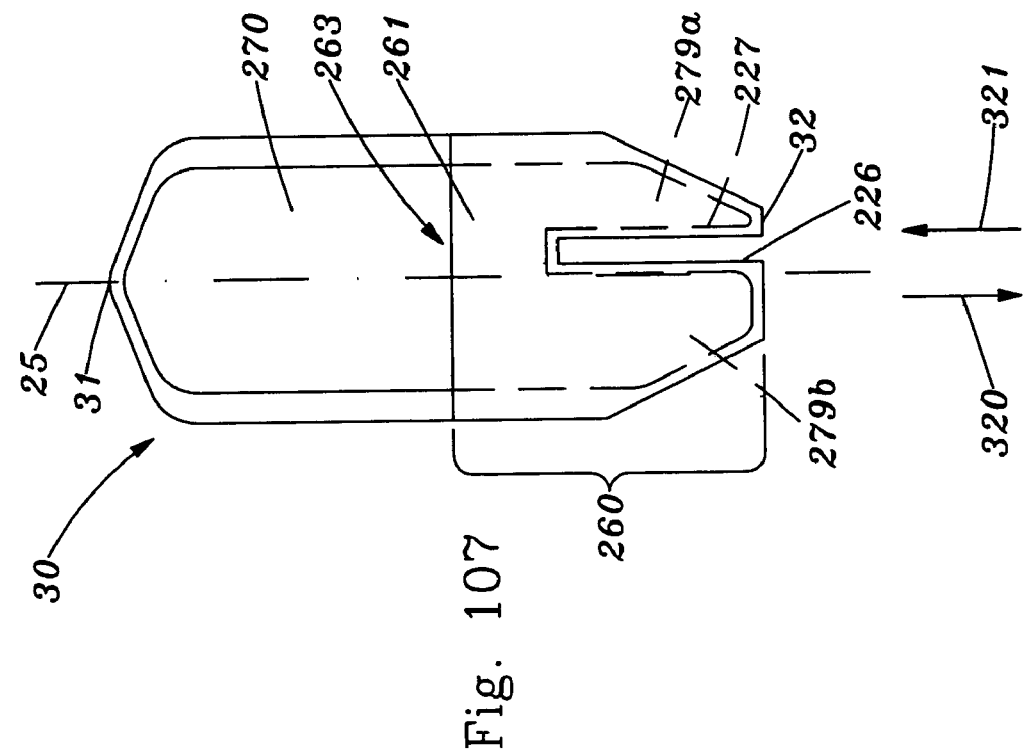

DISPOSABLE ABSORBENT ARTICLES WITH REPLACEABLE ABSORBENT CORE COMPONENTS HAVING REGIONS OF PERMEABILITY AND IMPERMEABILITY ON SAME SURFACE

CROSS-REFERENCE TO RELATED APPLICATIONS

This application is a continuation-in-part of commonly assigned U.S. application Ser. No. 09/911,108, filed on Jul. 23, 2001 now U.S. Pat. No. 6,932,800 in the name of LaVon et al., confirmation number 4986, which is a continuation-in-part of application Ser. No. 09/431,322, filed on Nov. 2, 1999, now abandoned, which was a continuation of application Ser. No. 08/825,071, filed on Mar. 27, 1997, now U.S. Pat. No. 6,015,935, and is a continuation-in-part of commonly assigned U.S. application Ser. No. 08/828,005, filed on Mar. 27, 1997 now U.S. Pat. No. 6,989,005 in the name of LaVon et al., confirmation number 4421, all of which are hereby incorporated in their entirety herein by reference.

FIELD OF THE INVENTION

This invention relates to disposable absorbent articles, such as disposable diapers and particularly to disposable absorbent articles having multi-piece absorbent cores in which some absorbent core components are non-removable and other absorbent core components are removable and replaceable.

BACKGROUND OF THE INVENTION

Disposable absorbent articles such as disposable diapers, incontinence pads, training pants, and catamenial napkins generally include an absorbent core for receiving and holding bodily exudates. The absorbent core typically includes a fibrous web, which can be a nonwoven, airlaid web of natural or synthetic fibers, or combinations thereof. Fibrous webs used in such absorbent articles also often include certain absorbent gelling materials usually referred to as "hydrogels," "superabsorbent" or "hydrocolloid" materials to store large quantities of the discharged bodily liquids. These materials absorb through capillary or osmotic forces, or a combination of both.

Many absorbent articles such as catamenial pads, adult incontinent products, and diapers are subject to leakage due to an inability to absorb second and subsequent discharges of liquid even if the first liquid discharge has been effectively absorbed. Leakage due to second and subsequent discharges is especially prevalent during the night, when users commonly experience multiple discharges before the absorbent article is changed. One reason for the inability of many absorbent articles to adequately handle multiple discharges of liquid is the inability of the absorbent core to transport discharged liquid away from the region of discharge once the absorbent capacity of that region has been reached. Thus, the overall performance of the absorbent article is limited by the inability to transport the liquid to the farthest reaches of the absorbent core.

An alternative absorbent material capable of providing capillary liquid transport is open-celled polymeric foam. Appropriately made open-celled polymeric foams provide features of capillary liquid acquisition, transport, and storage required for use in high performance absorbent cores for absorbent articles such as diapers. Shaped or contoured absorbent cores made from such open-celled foam materials having particularly desirable liquid transport characteristics are disclosed in U.S. Pat. No. 5,147,345 issued to Young et al. on Sep. 15, 1992. The Young et al. '345 absorbent core includes both a liquid acquisition/distribution member and a liquid storage/redistribution member. The liquid acquisition/distribution member is positioned within the absorbent article in such a way as to receive or contact aqueous bodily liquid which has been discharged into the absorbent article by the wearer of the article. The liquid storage/redistribution member, in turn, is positioned within the article to be in capillary liquid communication with the liquid acquisition/distribution member.

Absorbent cores providing the desirable absorbent characteristics of the Young et al. '345 patent in an exemplary multi-piece configuration are disclosed in U.S. Pat. No. 5,906,602 issued to Weber et al. on May 25, 1999, which describes shaped absorbent cores having a front panel and a back panel in capillary liquid communication with a center section. The center section includes material generally suitable for liquid acquisition/distribution, while the front and back panels include material generally suitable for liquid storage/redistribution.

Despite the advances in absorbent articles and in liquid handling absorbent core materials, absorbent articles having multiple absorbent core components as well as those having unitary absorbent cores are generally designed for single use wear. Once the storage/redistribution member is saturated with bodily discharges, such as urine, the entire absorbent article is generally discarded and replaced. Often parts of the absorbent article are still usable, and except for being unitary with the absorbent core, these parts could be used further. In addition to the added cost and waste associated with discarding reusable materials, it is often inconvenient to remove and replace the entire absorbent article when absorbent core components are saturated.

Absorbent articles having removable absorbent inserts and thereby being potentially usable for more than a single use are known in the art. For example, U.S. Pat. No. 4,597,761 to Buell, issued Jul. 1, 1986, discloses a disposable absorbent insert for use inside an over-garment such as a conventional reusable diaper, or a disposable diaper. Once the absorbent insert becomes saturated it may be removed and discarded. The absorbent article may then be reused with a fresh absorbent insert. However, because the absorbent insert is removable only from the body side of the article, the absorbent article must be removed from the wearer in order to remove the insert. Therefore, the removal of the absorbent insert is often inconvenient and time consuming.

Accordingly, it would be desirable to provide an absorbent article having a replaceable absorbent core component wherein the absorbent core component can be replaced without having to remove the absorbent article from the wearer.

Additionally, it would be desirable to provide an absorbent article having a replaceable absorbent core component and an apertured backsheet, allowing a saturated component of the absorbent core to be removed through the backsheet aperture, thereby exposing an unsaturated component and allowing for prolonged use of the reusable portions of the absorbent article.

Furthermore, it would be desirable to provide an absorbent article having a replaceable absorbent core component disposed between a topsheet and a backsheet, configured such that access to the replaceable absorbent core component is gained by separating the topsheet and the backsheet in a predetermined area to form an opening.

SUMMARY OF THE INVENTION

The present invention provides a disposable absorbent article adapted to be worn about a lower torso of a human body, including a chassis forming a waist opening and a pair of leg openings and having longitudinally opposed waist end edges, longitudinally opposed waist regions, and a crotch region longitudinally intermediate of the waist regions, a non-removable absorbent core component disposed in the crotch region, and a replaceable absorbent core component disposed in capillary liquid communication with the non-removable absorbent core component.

BRIEF DESCRIPTION OF THE DRAWINGS

While the specification concludes with claims particularly pointing out and distinctly claiming the present invention, it is believed that the present invention will be better understood from the following description in conjunction with the accompanying Drawing Figures, in which like reference numerals identify like elements, and wherein:

FIG. 37 is a partial section view showing a folded extensible covering layer in an unextended state;

FIG. 38 is a partial section view showing the folded extensible covering layer of FIG. 37 in an extended state;

FIG. 39 is a plan view showing a replaceable absorbent core component having a pull tab at its outer end;

FIG. 40 is a plan view showing another replaceable absorbent core component having a pull ring at its outer end;

FIG. 53 is a partial section view showing a replaceable absorbent core component of FIG. 52 in an improper orientation of its wearer-facing and garment-facing surfaces and a proper orientation of its inner and outer ends;

FIG. 54 is a partial section view showing the replaceable absorbent core component of FIG. 52 in an improper orientation of both its inner and outer ends and its wearer-facing and garment-facing surfaces;

FIG. 55 is a partial section view showing the replaceable absorbent core component of FIG. 52 in an improper orientation of its inner and outer ends and a proper orientation of its wearer-facing and garment-facing surfaces;

FIG. 58 is a plan view showing a replaceable absorbent core component having a relatively deep insertion pocket on its outer surface;

FIG. 59 is a partial section view showing the replaceable absorbent core component of FIG. 58;

FIG. 60 is a plan view showing a replaceable absorbent core component having intermittent linear bonds attaching an insertion pocket to its outer surface;

FIG. 61 is a plan view showing a replaceable absorbent core component having spot bonds attaching an insertion pocket to its outer surface;

FIG. 62 is a plan view showing a replaceable absorbent core component having continuous linear bonds attaching an insertion pocket to its outer surface;

FIG. 63 is a plan view showing a replaceable absorbent core component having a rectangular inner end and an insertion pocket on its outer surface;

FIG. 64 is a partial section view showing a replaceable absorbent core component having two relatively shallow insertion pockets on its two major surfaces;

FIG. 65 is a partial section view showing a replaceable absorbent core component having two relatively deep insertion pockets on its two major surfaces;

FIG. 69 is a partial section view showing a replaceable absorbent core component having a covering sheet wrapping over its inner end;

FIG. 70 is a partial section view showing a replaceable absorbent core component having a covering sheet wrapping over its inner end and forming an insertion pocket;

FIG. 80 is a plan view showing a replaceable absorbent core component having a "dipstick" type liquid presence indicator in its fully inserted position;

FIG. 81 is a plan view showing the "dipstick" type liquid presence indicator of FIG. 80 in its partially withdrawn position;

FIG. 82 is a plan view showing a replaceable absorbent core component having a series of visible liquid presence indication means on a "dipstick" type liquid presence indicator;

FIG. 93 is a partial section view showing a replaceable absorbent core component having two insertion tools disposed in two insertion pockets on its two major surfaces;

FIG. 94 is a partial section view showing a replaceable absorbent core component having an insertion tool joined to it through an intermediate member in its configuration for insertion;

FIG. 95 is a partial section view showing the replaceable absorbent core component of FIG. 94 having the insertion tool joined to it through the intermediate member in its partially detached configuration during withdrawal of the insertion tool;

FIG. 101 is a plan view showing an insertion tool having a relatively thicker inner end portion;

FIG. 102 is an edge view showing the insertion tool of FIG. 101;

FIG. 103 is a plan view showing another insertion tool having a relatively thicker inner end portion;

FIG. 104 is an edge view showing the insertion tool of FIG. 103;

FIG. 105 is a plan view showing another insertion tool having a relatively thicker inner end portion;

FIG. 106 is an edge view showing the insertion tool of FIG. 105;

FIG. 107 is a plan view showing a replaceable absorbent core component and an insertion tool having a longitudinal slot; and FIG. 108 is a plan view showing a replaceable absorbent core component having a longitudinal slot and an insertion tool having two finger-like sections.

DETAILED DESCRIPTION OF THE INVENTION

Figure 1:
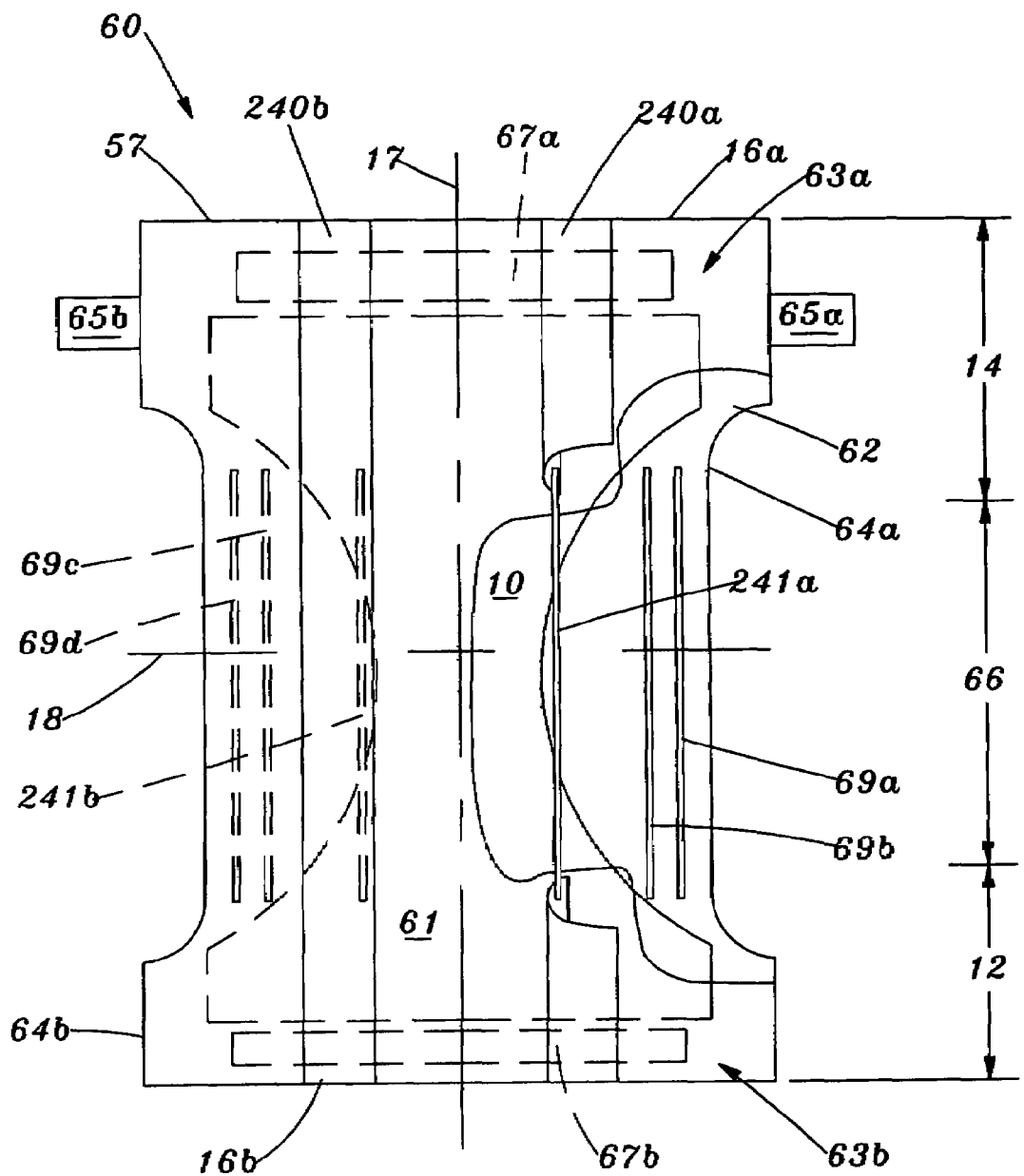
FIG. 1 is a plan view of an exemplary diaper of the present invention in its flat-out, uncontracted state, i.e., with all elastic induced contraction pulled out, with portions of the structure being cut away to more clearly show the construction of the diaper, and with the portion of the diaper that contacts the wearer facing the viewer.

The disclosures of all patents, patent applications, and any patents which issue thereon, as well as any corresponding published foreign patent applications, and all publications listed and/or referenced hereafter in this description, are hereby incorporated herein by reference. It is expressly not admitted, however, that any of the documents or any combination of the documents incorporated herein by reference teaches or discloses the present invention.

LIST OF U.S. PATENT REFERENCES

U.S. Pat. No. 3,848,594 to Buell, issued Nov. 19, 1974
U.S. Pat. No. 3,860,003 to Buell, issued Jan. 14, 1975
U.S. Pat. No. 4,062,817 to Westerman, issued Dec. 13, 1977
U.S. Pat. No. 4,076,663 to Masuda et al., issued Feb. 28, 1978
U.S. Pat. No. 4,081,301 to Buell, issued Mar. 28, 1978
U.S. Pat. No. 4,260,443 to Lindsay et al., issued Apr. 7, 1981
U.S. Pat. No. 4,467,012 to Pedersen et al., issued Aug. 21, 1984
U.S. Pat. No. 4,515,595 to Kievit et al., issued May 7, 1985
U.S. Pat. No. 4,625,001 to Tsubakimoto et al., issued Nov. 25, 1986
U.S. Pat. No. 4,654,039 to Brandt et al., issued Mar. 31, 1987 (reissued Apr. 19, 1988 as Re. 32,649)
U.S. Pat. No. 4,666,983 to Tsubakimoto et al., issued May 19, 1987
U.S. Pat. No. 4,681,580 to Reising et al., issued Jul. 21, 1987
U.S. Pat. No. 4,695,278 to Lawson, issued Sep. 22, 1987
U.S. Pat. No. 4,715,918 to Lang, issued Dec. 29, 1987
U.S. Pat. No. 4,773,903 to Weisman et al., issued Sep. 27, 1988
U.S. Pat. No. 4,795,454 to Dragoo, issued Jan. 3, 1989
U.S. Pat. No. 4,808,178 to Aziz et al., issued Feb. 28, 1989
U.S. Pat. No. 4,816,025 to Foreman, issued Mar. 28, 1989
U.S. Pat. No. 4,822,453 to Dean et al., issued Apr. 18, 1989
U.S. Pat. No. 4,851,069 to Packard et al., issued Jul. 25, 1989
U.S. Pat. No. 4,888,093 to Dean et al., issued Dec. 19, 1989
U.S. Pat. No. 4,892,536 to DesMarais et al., issued Jan. 9, 1990
U.S. Pat. No. 4,898,642 to Moore et al., issued Feb. 6, 1990
U.S. Pat. No. 4,923,454, to Seymour et al., issued May 8, 1990
U.S. Pat. No. 4,950,264 to Osborn, issued Aug. 21, 1990
U.S. Pat. No. 4,988,344 to Reising et al., issued Jan. 29, 1991
U.S. Pat. No. 4,988,345 to Reising, issued Jan. 29, 1991
U.S. Pat. No. 4,990,147 to Freeland, issued Feb. 5, 1991
U.S. Pat. No. 4,994,037 to Bernardin, issued Feb. 19, 1991
U.S. Pat. No. 5,009,650 to Bernardin, issued Apr. 23, 1991
U.S. Pat. No. 5,009,653 to Osborn, issued Apr. 23, 1991
U.S. Pat. No. 5,037,416 to Allen et al., issued Aug. 6, 1991
U.S. Pat. No. 5,061,259 to Goldman et. al, issued Oct. 29, 1991
U.S. Pat. No. 5,102,597 to Roe et al., issued Apr. 7, 1992
U.S. Pat. No. 5,128,082 to Makoui, issued Jul. 7, 1992
U.S. Pat. No. 5,137,537 to Herron et al., issued Aug. 11, 1992
U.S. Pat. No. 5,143,679 to Weber et al., issued Sep. 1, 1992
U.S. Pat. No. 5,147,345 to Young et al., issued Sep. 15, 1992
U.S. Pat. No. 5,149,335 to Kellenberger et al., issued Sep. 22, 1992
U.S. Pat. No. 5,151,092 to Buell et al., issued Sep. 29, 1992
U.S. Pat. No. 5,156,793 to Buell et al., issued Oct. 20, 1992

U.S. Pat. No. 5,167,897 to Weber et al., issued Dec. 1, 1992
U.S. Pat. No. 5,176,668 to Bernardin, issued Jan. 5, 1993
U.S. Pat. No. 5,217,445 to Young et al., issued Jun. 8, 1993
U.S. Pat. No. 5,221,274 to Buell et al., issued Jun. 22, 1993
U.S. Pat. No. 5,260,345 to DesMarais et al., issued Nov. 9, 1993
U.S. Pat. No. 5,268,224 to DesMarais et al., issued Dec. 7, 1993
U.S. Pat. No. 5,269,775 to Freeland et al., issued Dec. 14, 1993
U.S. Pat. No. 5,324,561 to Rezai et al., issued Jun. 28, 1994
U.S. Pat. No. 5,358,500 to LaVon et al., issued Oct. 25, 1994
U.S. Pat. No. 5,387,207 to Dyer et al., issued Feb. 7, 1995
U.S. Pat. No. 5,531,728 to Lash, issued Jul. 2, 1996
U.S. Pat. No. 5,549,589 to Horney et al., issued Aug. 27, 1996
U.S. Pat. No. 5,550,167 to Des Marais et al., issued Aug. 27, 1996
U.S. Pat. No. 5,554,145 to Roe et al., issued Sep. 10, 1996
U.S. Pat. No. 5,562,646 to Goldman et al., issued Oct. 8, 1996
U.S. Pat. No. 5,563,179 to Stone et al., issued Oct. 18, 1996
U.S. Pat. No. 5,569,234 to Buell et al., issued Oct. 29, 1996
U.S. Pat. No. 5,571,096 to Dobrin et al., issued Nov. 5, 1996
U.S. Pat. No. 5,817,081 to LaVon et al., issued Oct. 6, 1998
U.S. Pat. No. 5,599,335 to Goldman et al., issued Feb. 4, 1997
U.S. Pat. No. 5,650,222 to DesMarais et al., issued Jul. 22, 1997
U.S. Pat. No. 5,800,416 to Seger et al., issued Sep. 1, 1998
U.S. Pat. No. 5,843,055 to Seger et al., issued Dec. 1, 1998
U.S. Pat. No. 5,865,823 to Curro, issued Feb. 2, 1999
U.S. Pat. No. 5,897,545 to Kline et al., issued Apr. 27, 1999
U.S. Pat. No. 5,906,602 to Weber et al., issued May 25, 1999
U.S. Pat. No. 6,004,306 to Robles et al., issued Dec. 21, 1999
U.S. Pat. No. 6,120,487 to Ashton., issued Oct. 19, 2000
U.S. Pat. No. 6,187,696 to Lim et al., issued Feb. 13, 2001
U.S. Pat. No. 6,251,097 to Kline et al., issued Jun. 26, 2001
U.S. Pat. No. 6,432,098 to Kline et al., issued Aug. 13, 2002

DEFINITIONS

The following definitions of terms may be useful for understanding the disclosure of the present invention.

Absorbent article: A device that absorbs and contains bodily exudates by means of an absorbent core, and, more specifically, a device which is placed against or in proximity to the body of a wearer to absorb and contain the various exudates discharged from the body. An exemplary embodiment of an absorbent article of the present invention is the disposable absorbent article, diaper 60, as shown in the drawing figures. It should be understood, however, that the present invention is also applicable to other absorbent articles such as incontinence briefs, incontinence undergarments, diaper holders and liners, training pants, pull-on diapers, and the like.

Absorbent core: An element of an absorbent article containing a material or a combination of materials suitable for absorbing, distributing, and storing aqueous liquids such as bodily exudates.

Absorbent core component: A structural constituent of an absorbent core, e.g., a piece of an absorbent core, such as one of multiple pieces in a multi-piece absorbent core.

Absorbent layer: A term referring to a discrete, identifiable sheet-like or web-like element of an absorbent core structure which may remain detached and relatively movable with respect to another such element or may be bonded or joined so as to remain permanently associated with another such element. Each absorbent layer may itself include a laminate or combination of several sheets or webs of similar or diverse compositions.

Absorbent member: A functional constituent of an absorbent core, e.g., a liquid acquisition member, a liquid acquisition/distribution member, or a liquid storage/redistribution member formed of a material or materials having particular liquid handling characteristics suitable for the specific function.

Absorbent insert: A device adapted for insertion into an absorbent article and to serve as an absorbent core component when so inserted. A replaceable absorbent core component is an absorbent insert, the latter term being especially descriptive when referring to the device alone.

Chassis: A foundational constituent of an absorbent article upon which the remainder of the structure of the article is built up or overlaid, e.g., in a diaper, the structural elements that give the diaper the form of briefs or short pants when configured for wearing, such as a backsheet, a topsheet, or a combination of a topsheet and a backsheet.

Diaper: An absorbent article generally worn by infants and incontinent persons about the lower torso of the wearer.

Disposable: A term used to describe absorbent articles that are not intended to be laundered or otherwise restored or reused as an absorbent article after use, i.e., that are intended to be discarded after a single use and, preferably, to be recycled, composted or otherwise disposed of in an environmentally compatible manner. Note that, as described in this disclosure, a single use of a chassis and a non-removable core component may correspond to several uses and replacements of replaceable core components.

Capillary liquid communication: The flow of a liquid from one absorbent element to another absorbent element by capillary transport. Also, a term used to describe a structural disposition of absorbent elements in which the flow of a liquid from one of the absorbent elements to the other occurs through capillary transport of the liquid, generally requiring either the direct face-to-face contact of the absorbent elements with each other, the direct face-to-face contact of each of the absorbent elements with a hydrophilic intermediate layer providing capillary conduction of the liquid from one absorbent element to the other, or the protrusion of the fibers of a fibrous absorbent element through a porous and/or permeable intermediate layer into contact with the other absorbent element.

Join, joined, joining: Terms encompassing configurations wherein an element is directly secured to another element by affixing the element directly to the other element, as well as configurations wherein the element is indirectly secured to the other element by affixing the element to an intermediate member or members which in turn is or are affixed to the other element.

Major surface: A term used to describe the surfaces of greatest extent of a generally planar or sheet-like structural element and to distinguish these surfaces from the minor surfaces of the end edges and the side edges, i.e., in an element having a length, a width, and a thickness, the thickness being the smallest of the three dimensions, the major surfaces are those defined by the length and the width and thus having the greatest extent.

Replaceable: A term used to describe a component of an absorbent article that can be replaced, that is, a component that can be removed and for which a like component can be substituted in place of the removed component, e.g., a replaceable absorbent core component or absorbent insert.

Stratum, stratified: Terms referring herein to overlying or superimposed regions within a given layer or structure which have identifiably diverse compositions, densities, or other material properties such that the layer or structure is non-homogeneous through a cross section from one surface to an opposing surface.

Wearer-facing layer: The elements of the chassis that form the inner surface of the absorbent article, such as the topsheet, the leg cuffs, and the side panels, etc., when such elements are present.

Garment-facing layer: The elements of the chassis that form the outer surface of the absorbent article, such as the backsheet, the side panels, the waist fasteners, and the like, when such elements are present.

OVERALL DESCRIPTION

As described below in detail, the present invention relates to absorbent articles suitable for absorbing and retaining aqueous bodily liquids. These absorbent articles of the present invention generally include a backsheet formed of a substantially liquid impervious material and an absorbent core disposed adjacent to the backsheet. The absorbent core includes at least one removable core component disposed in capillary liquid communication with at least one non-removable core component. The removable core component may be inserted into the absorbent article prior to the application of the absorbent article to the wearer or while the absorbent article is being worn. When the removable core component or a member of it is removed, a replacement absorbent core component or member may be inserted in place of the removed component or member.

In some exemplary embodiments, the absorbent article may include a plurality of absorbent core components, including a front panel and a rear panel in capillary liquid communication with a center section. Each of the absorbent core components may include multiple absorbent layers. Upon saturation with bodily discharges, removable components or absorbent layers of the absorbent core may be removed from the absorbent article. New, unsaturated absorbent core components or absorbent layers may then be positioned in place of the removed saturated core components or absorbent layers.

In some exemplary embodiments, the removable core component is disposed adjacent to the body-facing surface of the backsheet and is accessible through an aperture in the backsheet. In other exemplary embodiments, the removable core component is disposed adjacent to the garment-facing surface of the backsheet and is contained in a pocket formed by a piece of sheet material affixed to the outer surface of the backsheet.

In some exemplary embodiments, the absorbent article includes a liquid pervious topsheet and a substantially liquid impervious backsheet joined to the topsheet about the periphery of the absorbent article. In a predetermined area of the periphery, the topsheet and the backsheet may be separated to form an opening providing access to a removable core component disposed between the topsheet and the backsheet and for the insertion of a replacement core component.

In these exemplary embodiments, the center absorbent core component preferably has suitable liquid acquisition and/or acquisition/distribution characteristics, while the front and rear absorbent core panels or components preferably have suitable storage/redistribution characteristics.

Exemplary Diaper Embodiment

Figure 2:
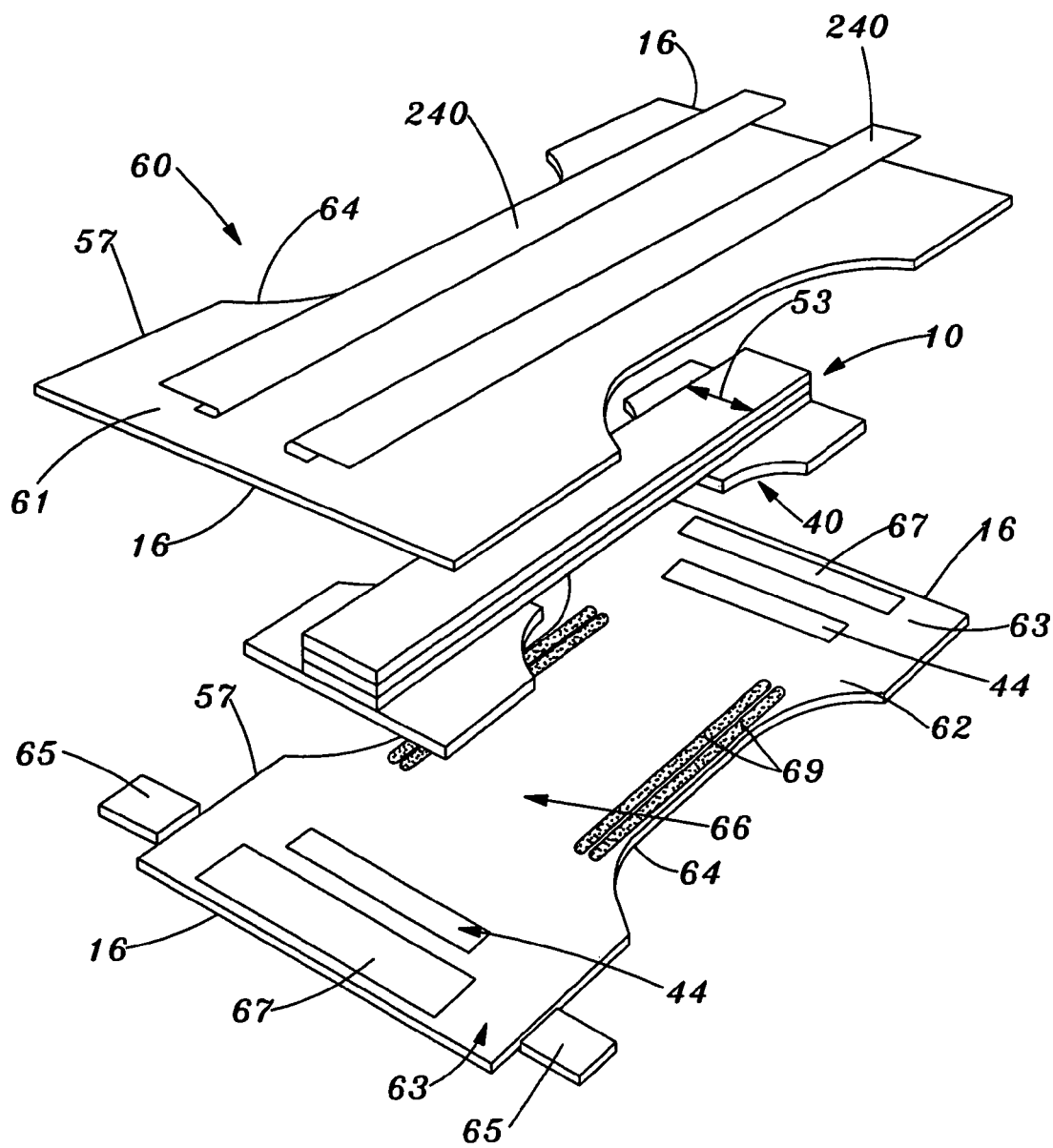
FIG. 2 is an exploded perspective view depicting an exemplary absorbent article, with the portion of the article that contacts the wearer facing upward.

FIG. 1 is a plan view of an exemplary embodiment of an absorbent article of the present invention and shows exemplary diaper 60 in its flat-out, uncontracted state, i.e., with all elastic induced contraction pulled out, with portions of the structure being cut away to more clearly show the construction of the diaper, and with the portion of the diaper which contacts the wearer facing the viewer. FIG. 2 also shows an exemplary diaper 60 in an exploded perspective view, with the portion that contacts the wearer on top. In these exemplary embodiments, the diaper is shown to have a periphery 57 defined by the outer edges of the diaper, with the longitudinal edges being designated 64 and the waist end edges being designated 16. The diaper additionally has a lateral centerline which is designated 18 and a longitudinal centerline which is designated 17. The front waist region 12 and the back waist region 14 extend, respectively, from the waist end edges 16 toward the lateral centerline 18 a distance from about ¼ to about ⅓ the length of the diaper. The waist regions form those portions of the diaper which, when worn, encircle the waist of the wearer. The crotch region 66 is that portion of the diaper between the waist regions, and forms that portion of the diaper which, when worn, is positioned between the legs of the wearer and covers the lower torso of the wearer.

Figure 3:
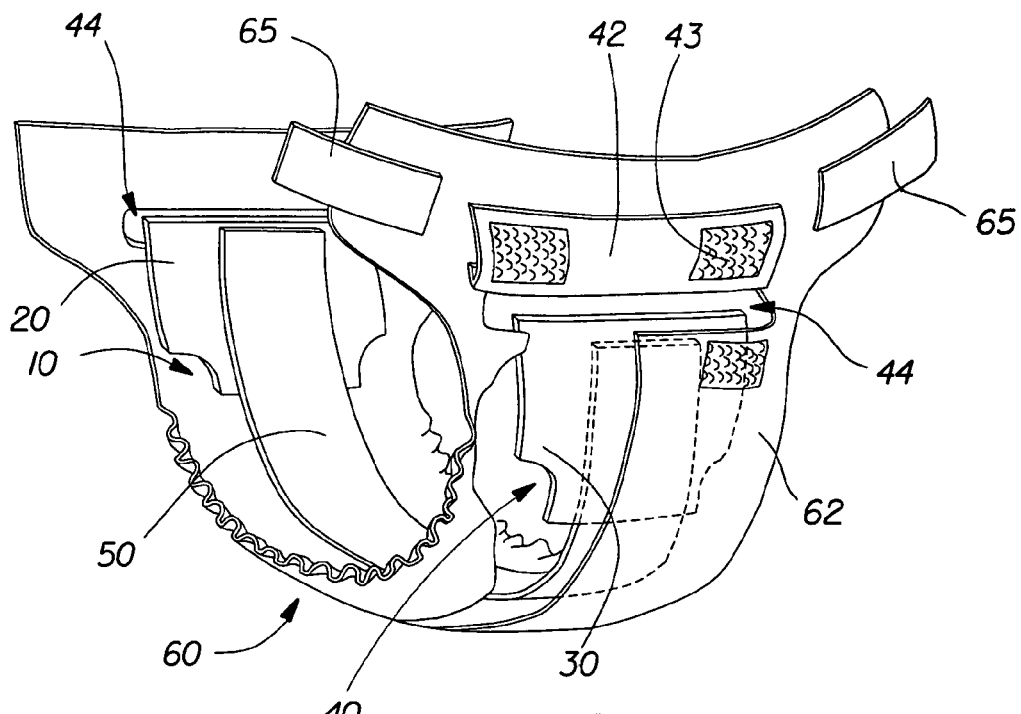
FIG. 3 is a perspective, partially segmented illustration of an exemplary diaper embodiment of an absorbent article according to the present invention.
Figure 4:
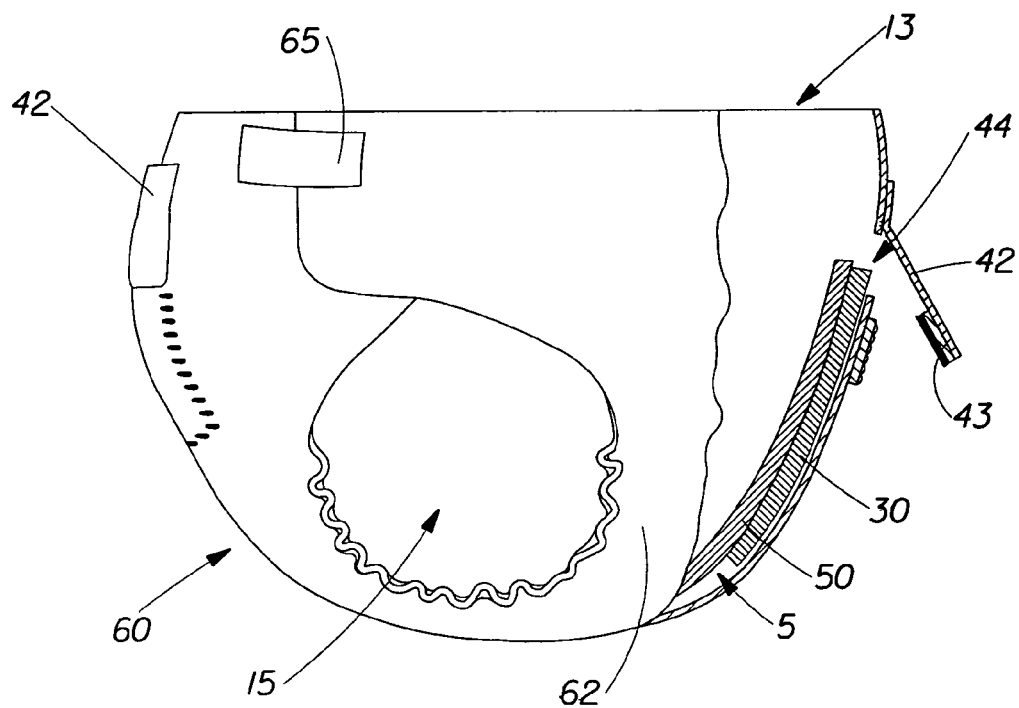
FIG. 4 is a side view, showing in partial cross-section, the exemplary absorbent article of FIG. 3.

Another exemplary disposable diaper 60 embodiment of an absorbent article of the present invention is shown in partially segmented perspective view in FIG. 3 and in a side view, partial cross-section in FIG. 4. The multi-piece absorbent core 10 including multiple absorbent core components, such as the center section 50, the front panel 20, and the back panel 30, is more fully illustrated and described below. The multi-piece absorbent core is also described in the Weber et al. '602 patent.

A multi-piece absorbent core having discrete components provides several benefits. First, the core exhibits desirable aesthetics and fit when used in an absorbent article of the present invention due to the use of discontinuous absorbent layers or panels of absorbent material. For example, the center section may include separate absorbent layers, allowing the center section to bend and buckle somewhat independently from adjacent absorbent layers and the front and rear panels and thereby provide better fit and comfort in the crotch area than is typically achieved with one-piece absorbent cores.

A second advantage provided by a multi-piece absorbent core is the ability to independently vary selected characteristics of the absorbent core components and members. The characteristics that may be varied include the acquisition rates, distribution rates, storage capacities and rates, interfacial liquid transfer rates and efficiencies, thickness, functionality, and the shape or configuration of the absorbent layers or panels. For example, in an exemplary embodiment of an absorbent article of the present invention, three absorbent layers may form the center section, with the absorbent layer closest to the body of the wearer having relatively greater acquisition characteristics than the remaining two outer absorbent layers having relatively greater acquisition/distribution characteristics. In this configuration, bodily discharges such as urine are quickly acquired by the body-side absorbent layer serving as an acquisition member and then desorbed into the adjacent absorbent layers serving as acquisition/distribution members for distribution to the front and back panels, which preferably have greater storage/redistribution characteristics.

A third benefit resulting from the use of a multi-piece absorbent core in an absorbent article of the present invention is the capability of removing and/or replacing components of the absorbent core to regenerate the storage/redistribution capacity of the absorbent core. The provision of access to the removable absorbent core components, for example, to the back panel, allows the removal and/or replacement of those absorbent core components. In this disclosure, all description of the back panels, their removal and replacement, and access to them for their removal and replacement, is generally applicable to the front panels and vice versa, in various exemplary embodiments.

By replacing absorbent core components, particularly absorbent core components that are primarily suited for storage/redistribution, the use of the absorbent article, such as the disposable diaper, may be prolonged while continuing to draw moisture away from the wearer's skin. As storage/redistribution absorbent core members in, e.g., the front panel and the back panel, become saturated, they may become substantially less effective at absorbing moisture from acquisition/distribution members in the center section. Consequently, the center section becomes more saturated, thereby hindering its ability to absorb as much moisture away from the wearer's skin. However, once an absorbent core component such as the back panel is replaced, the absorbent suction of that absorbent core component is regenerated, and it once again becomes capable of absorbing moisture from the acquisition/distribution member of the center section. Therefore, the disposable diaper may be worn longer, and regeneration of the absorbent core may be made without removal of the diaper from the wearer.

It should be understood that the absorbent core described herein may also be useful for other absorbent articles such as incontinent briefs, incontinent pads, training pants, and the like, and that the present invention is not limited to the particular type or configuration of diaper shown in the drawing figures.

In the incorporated references, the entire absorbent core is typically non-removably disposed in the absorbent article. However, as described throughout this disclosure, specific components of the multi-piece absorbent core are removable and replaceable in absorbent articles of the present invention. For instance, the front panel 20 and/or the back panel 30 may be removable and replaceable, while another component, such as the center section 50, may be non-removably disposed in any of the previously known configurations and thereby be made non-removable from the absorbent article. Thus, absorbent articles of the present invention have both non-removable absorbent core components and absorbent core components that are removable and replaceable.

As described in the incorporated references, components of the absorbent core may be made non-removable from the chassis by being secured, attached, affixed, and/or sandwiched to or in the chassis. For example, as described in the Buell '003 patent, an absorbent core component can be rendered immobile by, for example, bonding the backsheet and the absorbent core component together, bonding the absorbent core component to a topsheet and the topsheet to the backsheet, or tightly sandwiching the absorbent core component between a topsheet and the backsheet. Also, as described in the Lawson '278 patent, an absorbent core component may be superimposed on the backsheet and attached thereto by attachment means such as those well known in the art. For example, the absorbent core component may be secured to the backsheet by a uniform continuous layer of adhesive, a patterned layer of adhesive, or an array of separate lines or spots of adhesive. In some exemplary embodiments, an absorbent core component may be affixed in the crotch area of the chassis, as described in the DesMarais et al. '345 patent. Similarly, as described in the Osborn '264 patent, an absorbent core component may be attached over the core's upper or lower major surfaces, respectively, to adjacent members such as the topsheet and the backsheet by any of the means well known in the art, such as by spray-gluing or lines or spots of adhesive. In fact, such attachment may facilitate the integrity and recoverability of the absorbent materials while in use so as to maintain an optimum degree of absorbency.

In some exemplary embodiments of the present invention, a non-removable absorbent core component, such as the center section, may be joined to the chassis in a portion of the crotch region by affixing the non-removable core component to the topsheet or the backsheet or to both the topsheet and the backsheet. For example, the non-removable core component may be joined at the crotch point to the chassis. The end portions of the non-removable core component, i.e., the portions extending from the crotch region toward the front and back waist regions, may remain unattached to the chassis and thereby be free to "float" within the absorbent article. Alternatively, the front portion of the non-removable core component may be affixed to the chassis and only the rear portion may be allowed to float. This floating core configuration allows the unattached portion of the non-removable core component to slide relative to the backsheet and or the topsheet when the absorbent article is applied to the wearer. The floating core configuration also allows the unattached portion of the non-removable core component to slide in response to the contraction of the chassis caused by the elastics in the leg cuff regions of the absorbent article. Allowing a portion of the non-removable core component to slide relative to the chassis may avoid the folding and wrinkling of the non-removable core component that typically occurs in absorbent articles having the entire non-removable core component affixed to the distorted and/or contracted chassis.

The Absorbent Article Chassis

As described throughout this disclosure, the liquid absorbent core can be utilized in disposable absorbent products which are capable of absorbing significant quantities of bodily liquids, such as urine, perspiration, menses, and water in bodily wastes. These disposable absorbent articles may be prepared in the form of disposable diapers, adult incontinence briefs, training pants, and the like. Such form-fitting articles will generally include a flexible substrate fashioned into a chassis in the form of briefs or shorts when configured for wearing. A flexible substrate which forms the chassis of such a form-fitting article may include cloth or paper or other kinds of nonwoven substrate or formed films and may be elasticized or otherwise extensible. The chassis is the foundational element upon which the remainder of the structure of the article is built up or overlaid.

Because the designs of the chassis and the absorbent core are interrelated, the absorbent core is included in the following description in order to make the structural relationship between the two clear. A more detailed description of the absorbent core, itself, may be found in the next section of this disclosure.

In the exemplary embodiments shown in FIG. 1 and FIG. 2, the diaper has a substantially liquid impervious backsheet 62. On top of this backsheet is disposed an absorbent core 10 which may include one or more discrete absorbent layers and may include a superabsorbent material in one or more of the absorbent layers. On top of this absorbent core and joined to the backsheet is a fluid pervious topsheet 61. The topsheet is the element of the article that is placed next to the skin of the wearer. Additional structural features such as elastic members and fastening means for securing the diaper in place upon a wearer, such as tape tab fasteners, may also be included, as will be described below.

In these exemplary embodiments, the topsheet and the backsheet are coextensive and have length and width dimensions generally larger than those of the absorbent core. The topsheet is joined with and superimposed on the backsheet, thereby forming the chassis. While the topsheet, the backsheet, and the absorbent core can be assembled in a variety of well known configurations, an exemplary diaper configuration is described generally in the Buell '003 patent. Alternative exemplary configurations for disposable diapers herein are also disclosed in the Aziz et al. '178 patent; the Lawson '278 patent; and the Foreman '025 patent.

The backsheet is typically made of a material substantially impervious to liquids and is preferably manufactured from a thin plastic film, although other flexible liquid impervious materials may also be used. The backsheet prevents the exudates absorbed and contained in the absorbent core from wetting articles, such as bed sheets and undergarments, which contact the diaper. An exemplary backsheet may be made of polyethylene film having a thickness from about 0.013 mm (0.5 mil) to about 0.051 mm (2.0 mils), although other flexible liquid impervious materials can be used. As used herein, the term "flexible" refers to materials which are compliant and which will readily conform to the general shape and contour of the wearer's body. A suitable polyethylene film is manufactured by Monsanto Chemical Corporation and marketed in the trade as Film No. 8020. The backsheet may be embossed and/or matte finished to provide a more clothlike appearance.

At least a portion of the backsheet may be subjected to mechanical stretching to make it elongatable or drawable in order to provide a "zero strain" stretch laminate for, for example, forming elastic side panels. Suitable equipment and processes for such mechanical stretching and for the formation of such a zero strain stretch laminate are described in the Weber et al. '679 patent, the Buell et al. '793 patent, and the Weber et al. '897 patent.

Further, the backsheet may be "breathable," permitting vapors to escape from the absorbent core while still preventing exudates from passing through the backsheet. It is contemplated that a backsheet that is highly breathable but substantially impervious to liquid may be desirable for certain absorbent articles. Such breathable composite materials are described in greater detail in the Lim et al. '696 patent, in PCT Application No. WO 95/16746 in the name of Cardinal et al., published on Jun. 22, 1995, and in the Curro '823 patent. Other breathable backsheets including nonwoven webs and apertured formed films are described in the Dobrin et al. '096 patent.

The size of the backsheet is dictated by the size of the absorbent core and the exact diaper design selected. In an exemplary embodiment, the backsheet has a modified hourglass-shape extending beyond the absorbent core a minimum distance of at least about 1.3 centimeters to at least about 2.5 centimeters (about 0.5 to about 1.0 inch) around the entire diaper periphery.

The topsheet is compliant, soft feeling, and non-irritating to the wearer's skin. Further, at least a portion of the topsheet is liquid pervious permitting bodily liquids to readily penetrate through its thickness. A suitable topsheet can be manufactured from a wide range of materials such as woven and nonwoven materials; polymeric materials such as apertured formed thermoplastic films, apertured plastic films, and hydroformed thermoplastic films; porous foams; reticulated foams; reticulated thermoplastic films; and thermoplastic scrims. Suitable woven and nonwoven materials can include natural fibers, e.g., wood or cotton fibers, synthetic fibers, e.g., polymeric fibers such as polyester, polypropylene, or polyethylene fibers, or a combination of natural and synthetic fibers. Preferably, the topsheet is made of a hydrophobic material to isolate the wearer's skin from liquids in the absorbent core. Like the backsheet, at least a portion of the topsheet may be subjected to mechanical stretching to make it elongatable or drawable, in order to provide a "zero strain" stretch laminate for, for example, forming elastic side panels.

A number of manufacturing techniques may be used to manufacture the topsheet. For example, the topsheet can be formed of woven, nonwoven, spunbonded, carded, or like materials. In nonwoven topsheets, the fibers are typically bound together by a thermal binding procedure or by a polymeric binder such as polyacrylate. This sheet is substantially porous and permits a liquid to readily pass through it into the underlying absorbent core. The topsheet material will preferably have no affinity for holding aqueous bodily liquids in the area of contact between the topsheet and the wearer's skin.

High loft nonwoven topsheets and apertured formed film topsheets may be used in absorbent articles of the present invention. In some exemplary embodiments, apertured formed films may be preferred for the topsheet because they are pervious to bodily liquids and yet nonabsorbent, and they have a reduced tendency to allow liquids to pass through in a direction away from the absorbent core and thereby rewet the wearer's skin. Thus, the surface of the formed film that is in contact with the body remains dry, thereby reducing bodily soiling and creating a more comfortable feel for the wearer. The body-facing surface of the formed film topsheet can be hydrophilic, thereby helping bodily liquids transfer through the topsheet faster and diminishing the likelihood that liquid will flow off the topsheet rather than flowing into and being absorbed by the absorbent core.

The topsheet may have an elasticated aperture adapted to permit feces to pass through in a direction away from the wearer and be unattached in a portion of the crotch region and a portion of the rear of the chassis. The topsheet may be fully or partially elasticized or may be foreshortened to provide a void space between the topsheet and the non-removable core component. Exemplary structures including elasticized or foreshortened topsheets are described in more detail in the DesMarais et al. '536 patent, in the Freeland '147 patent, in the Allen et al. '416 patent, and in the Freeland et al. '775 patent.

The topsheet and the backsheet are joined together in any suitable manner. As used herein, the term "joined" encompasses configurations wherein the topsheet is directly joined to the backsheet by affixing the topsheet directly to the backsheet, and configurations wherein the topsheet is indirectly joined to the backsheet by affixing the topsheet to intermediate members which in turn are affixed to the backsheet. In an exemplary embodiment, the topsheet and the backsheet are affixed directly to each other in the absorbent article's periphery by attachment means (not shown) such as an adhesive or any other attachment means known in the art. For example, a uniform continuous layer of adhesive, a patterned layer of adhesive, or an array of separate lines or spots of adhesive can be used to affix the topsheet to the backsheet. The topsheet may also be adhered to the absorbent core.

Furthermore, it is contemplated that a suitable absorbent core structure without a topsheet could be used to provide desirable results, such as comfort and absorbency, as well as simplicity in manufacturing and material cost savings. For example, the body-side surface of the absorbent core could be made of liquid pervious, soft, compliant, non-irritating materials, thereby making a separate topsheet unnecessary. Such an absorbent core could be used in combination with a backsheet to provide the desired comfort and absorbency in an absorbent article.

Fastening means, such as tape tab fasteners 65, are typically disposed in the waistband region 63 of the diaper for holding the diaper on the wearer. The waistband region is generally considered to be that portion of the diaper extending from the waist end edge of the diaper to about the laterally extending margin of the absorbent core. The tape tab fasteners depicted are representative, only, and the fastening means can be any of those well known in the art, such as the fastening tape disclosed in the Buell '594 patent, mechanical fasteners, hook and loop fasteners, zippers, buttons, and the like. These tape tab fasteners or other diaper fastening means are typically applied near the corners of the diaper.

The absorbent article may have an "open" chassis configuration, as shown in FIG. 1, in which the chassis is adapted to be fastened together about the lower torso of a wearer by the fastening means. Suitable non-limiting examples of an open chassis include the disposable diaper embodiments described in the Buell '092 patent and in the LaVon et al. '500 patent.

An open chassis may be at least partially pre-fastened prior to its application onto the wearer. For example, articles capable of being pre-fastened and then applied in a pull-on fashion include those described in the Kline et al. '097 patent and in the Kline et al. '098 patent. In certain embodiments, the article may require a subsequent fastening step to adjust the size of, or the tension in, the waist circumference of the article once the article has been applied over the wearer's lower torso. For example, articles having such two-step fastening/tensioning systems include those described in currently pending U.S. application Ser. No. 09/994,191 for An Absorbent Article Fastening Device, filed Nov. 26, 2001 in the name of Magee et al.

Alternatively, the absorbent article may have a "closed" chassis configuration, such as that of a pull-on pant-type diaper or training pant, in which the chassis is adapted to be pulled on over the legs and lower torso of the wearer without any additional fastening steps. Suitable non-limiting examples of a closed system include the disposable diapers and training pants described in the Buell '234 patent and in the Ashton '487 patent.

In both open and closed chassis configurations, it is desirable for the absorbent article to have extensible side panels 210 and preferably elastically extensible side panels to maximize the ease of insertion and removal of the replaceable core component. Suitable non-limiting examples of disposable absorbent articles having extensible side panels are described in the Buell et al. '092 patent, in the Buell et al. '274 patent, in the Roe et al. '145 patent, in the LaVon et al. '500 patent, in the Kline et al. '545 patent, and in the Robles et al. '306 patent.

Leg elastic members 69 may be disposed adjacent to the periphery of the diaper, preferably along each longitudinal edge 64 to form an elastically contractible leg cuff or side flap, so that the elastic members tend to draw and hold the diaper against the legs of the wearer. The leg elastic members may extend along a portion of the length of the diaper. Alternatively, the leg elastic members can extend the entire length of the diaper, or any other length suitable to provide an elastically contractible line. The length of the leg elastic members is dictated by the diaper design.

A barrier leg cuff 240 including a barrier leg cuff elastic member 241 may be disposed adjacent to each longitudinal edge 64 or between the longitudinal edge and the longitudinal centerline 17 of the diaper. Suitable barrier leg cuff materials and structures are described in the Lawson '278 patent, in the Young et al. '345 patent, in the DesMarais et al. '345 patent, in the Dyer et al., '207 patent, in the Foreman '025 patent, and in the Aziz et al. '178 patent.

Additionally, waist elastic members 67 can be disposed adjacent to either the front, the back, or both of the waistband regions of the diaper to provide a waistband as well as or rather than leg cuffs. While the waistband can comprise a separate element affixed to the body of the disposable diaper, it more often is an extension of other elements of the disposable diaper, such as the backsheet or the topsheet or both the backsheet and the topsheet. Disposable diapers are normally constructed so as to have two waistbands: a front and a rear.

A suitable waistband is disclosed in the Kievit et al. '595 patent. In one exemplary embodiment illustrated in the Kievit et al. '595 patent, elastic waist elements extend across essentially the entire lateral width of the disposable diaper. While this construction may be preferred in some exemplary embodiments, similar waistbands may be useful in designs wherein the elastic waist elements extend across only a portion of the lateral width of the diaper. Preferably, the elastic waist elements extend across a major portion of the lateral width of the disposable diaper.

The elastic members are secured to the diaper in an elastically contractible condition so that in a normally unrestrained configuration, the elastic members effectively contract or gather portions of the diaper. The elastic members can be secured in an elastically contractible condition in at least two ways. For example, the elastic members can be stretched and secured while the diaper is in an uncontracted condition. Alternatively, the diaper can be contracted, for example, by pleating, and the elastic members can be secured and connected to the diaper while the elastic members are in their unrelaxed or unstretched condition. A method and apparatus suitable for manufacturing a disposable diaper having elastically contractible elastic members is described in the Buell '301 patent.

In use, an open chassis version of the diaper is applied to a wearer by positioning one waistband region under the wearer's back, and drawing the remainder of the diaper between the wearer's legs so that the other waistband region is positioned across the front of the wearer. The tape-tab or other fasteners are then secured, preferably to outwardly facing areas of the diaper, as shown in FIG. 4, for example. As can be seen in FIG. 4, the chassis forms a waist opening 13 and leg openings 15 when configured for wearing.

The Absorbent Core

In use, the disposable diapers or other absorbent articles of the present invention tend to more quickly and efficiently distribute and store liquids and to remain dry due to the high absorbent capacity of the absorbent core components. Disposable diapers incorporating the absorbent core components of the present invention can also be thinner and more flexible.

Figure 5:
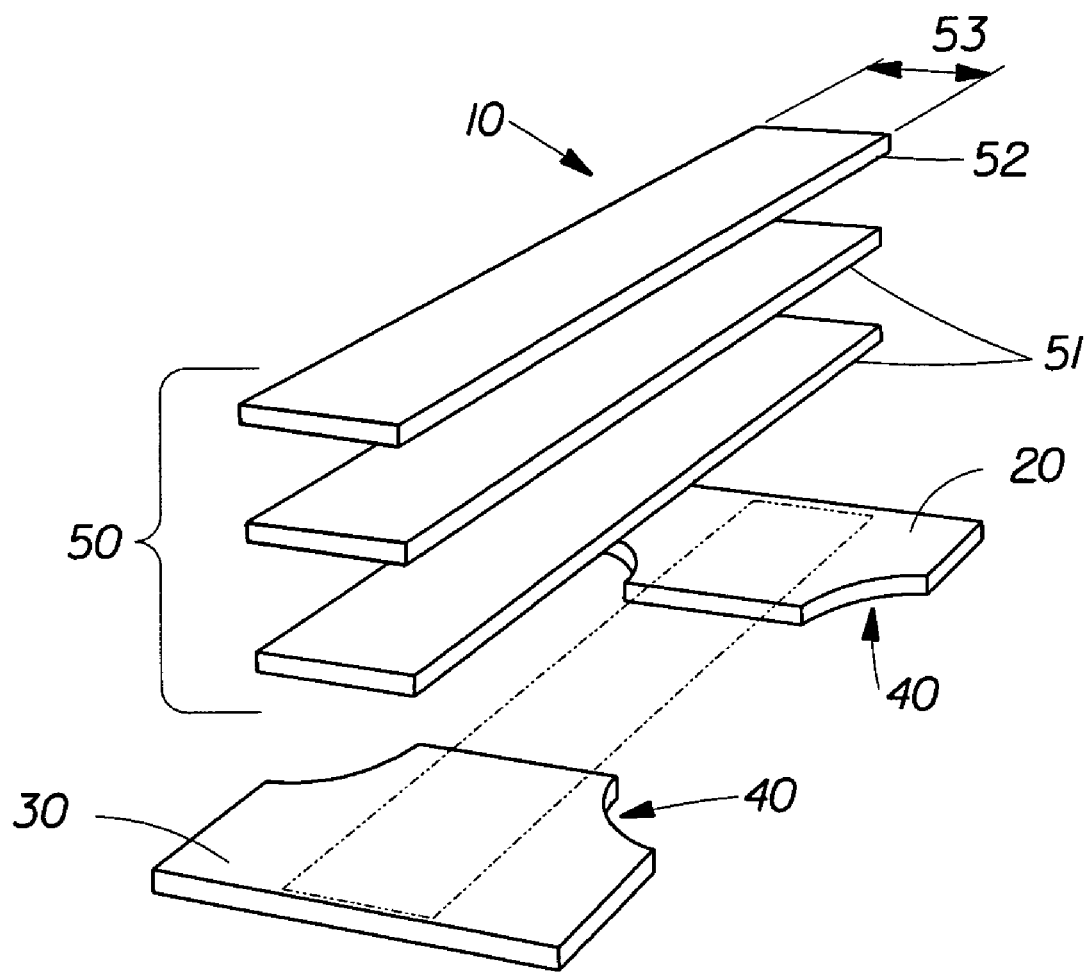
FIG. 5 is an exploded perspective view depicting the relationship between the elements of an exemplary absorbent core of the present invention, with the portion of the core that faces the wearer facing upward.
Figure 6:
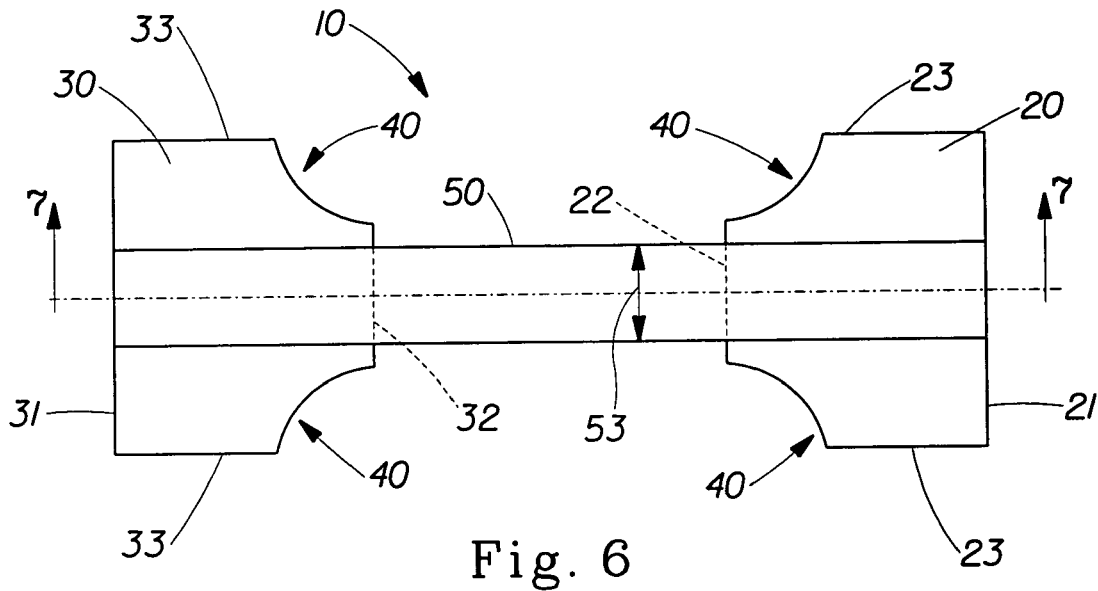
FIG. 6 shows a top plan view of an exemplary absorbent core useful in an absorbent article according to the present invention.

FIG. 5 shows an exploded perspective view depicting the elements of an exemplary embodiment of a shaped absorbent core 10 such as may be used in an absorbent article according to the present invention, for example, in a disposable diaper. FIG. 6 shows a top plan view of such a shaped absorbent core 10.

As depicted in FIG. 5 and FIG. 6, the absorbent core 10 includes a front panel 20 and a back panel 30, both made of absorbent material, preferably material suitable for liquid storage/redistribution. The front panel has an outer front end 21, an inner front end 22, and a pair of sides 23. Similarly, the back panel has an outer back end 31, an inner back end 32, and a pair of sides 33. In this exemplary embodiment, the front and back panels, together with the center section 50, generally form an elongated hourglass shape suitable for use in a disposable diaper or similar absorbent article.

Since the center section 50 and the front panel 20 and the back panel 30 are discrete absorbent core components, the center section 50 may be non-removable, while the front panel 20 or the back panel 30, or both, may be removable from the diaper 60. Thus, when the front panel 20 or the back panel 30 becomes saturated with bodily discharges, such as urine, it can be removed and replaced with a fresh panel for continued use of the absorbent article.

The center section may be generally rectilinear. The term "generally rectilinear" refers to the center section having a generally constant width along its length. In general, however, the center section may have a varying width along its length. The center section may extend from about the outer front end 21 of the front panel, to about the outer back end 31 of the back panel, as shown in FIG. 6. In use, however, the center section need only be in capillary liquid communication with the front and back panels, such as by overlapping in a layered relationship, and may not extend to the outer front end or the outer back end.

In an exemplary embodiment, the width 53 of the center section is suitable for comfortably fitting within the crotch area of the wearer when the absorbent core is incorporated into an absorbent article, such as a disposable diaper. The length of the generally rectilinear center section may be varied to provide a suitable fit for various wearer sizes.

In a generally flat, unfolded state, the front panel and the back panel are disposed such that the inner front end 22 of the front panel is opposed to and spaced from the inner back end 32 of the back panel as shown in FIG. 5 and FIG. 6. The distance between the front and back panels may be varied as necessary. In general, the distance will increase as the crotch length increases with the size of the absorbent article. The front panel generally lies in the front waist region, with the outer front end 21 being generally near the front waist end edge and the inner front end 22 lying in the crotch region. Similarly, the back panel lies in the back waist region, with the outer back end 31 being generally near the back waist end edge and the inner back end 32 lying in the crotch region. In some exemplary embodiments, the back panel 30 is longer than the front panel 20. Such a configuration lends itself to a better fit when the absorbent core is used in a disposable diaper.

As shown in FIG. 2, FIG. 3, FIG. 5, and FIG. 6, the front panel 20 may have cut-out areas 40 at the intersection of the sides 23 and the inner front end 22 and the back panel 30 may have cut-out areas 40 at the intersection of the sides 33 and the inner back end 32. The cut-out areas, or notched portions, join the sides and the inner ends such that the resulting widths of the inner ends 22 and 32 are narrower than those of the outer ends 21 and 31, respectively and, as shown in the figures, approach the width 53 of the center section, which is suitable for comfortably fitting within the crotch area of the wearer when the absorbent core is incorporated into an absorbent article, as stated above. The term "notched" refers to a shape in which, instead of a side and an end meeting generally at a right angle, some amount of material is removed from the corner to produce an additional edge portion joining the side and the end. The additional edge portion of the cut-out areas may be generally straight, but in an exemplary embodiment it is generally arcuate, as depicted in FIG. 6. It is also contemplated that the cut-out areas may have generally straight sides, with the limiting example resulting in a back panel or a front panel being substantially trapezoidal in shape.

It is important for understanding the present invention to note that, unlike the front panel and the back panel of the absorbent core of the present invention, an absorbent core component that extends from one waist region through the crotch region to the opposing waist region of an absorbent article typically presents several disadvantages relative to its potential use as a replaceable core component. Fundamentally, any such core component must both fit comfortably in the relatively narrow crotch of the wearer and provide a useful amount of absorbent capacity, both in the crotch region and in the waist regions. The hourglass shape of many absorbent cores in absorbent articles known in the art represents a compromise between the requirements of making the crotch portion of the core narrow enough to fit comfortably, yet wide enough to provide sufficient absorbent capacity in the crotch region to accept gushes of urine, and making the waist region portions of the core large enough to provide sufficient overall absorbent capacity. The removal or the insertion of such an absorbent core component extending through the crotch region while the absorbent article is being worn would be relatively difficult and/or impractical, because either the removal or the insertion would necessitate passing an entire relatively wide waist region portion of the absorbent core component directly through the relatively narrow crotch of the wearer. Specifically, the removal would require either pulling one relatively wide waist region portion of the core component through the wearer's relatively narrow crotch toward the opposing waist region without tearing or otherwise disassembling the core component, or reaching into both the front and the back of the waist opening to both push and pull the core component through the wearer's crotch. The insertion would require both forcing a relatively wide waist region portion of the core component through the wearer's relatively narrow crotch, either by pushing it through the crotch or by both pulling and pushing it through the crotch, and then spreading that waist region portion of the core component in order to dispose it properly in the waist region of the absorbent article. It is clear that the performance of such a removal or, especially, of such an insertion, would be highly uncomfortable for the wearer and that the likelihood of its successful completion, i.e., the likelihood of its completion without tearing or otherwise damaging the absorbent core component or the chassis of the absorbent article, would be low.

It is also important to note that if, in an attempt to facilitate the removal and/or the insertion of such an absorbent core component extending through the crotch region, an oversized absorbent article is applied to a wearer or an absorbent article is applied relatively loosely onto the torso of a wearer, the likely results are the undesirable leakage of bodily liquids from the poorly fitted leg openings and the sagging or sliding of the absorbent article toward the knees of the wearer. The occurrence of either of these problems would clearly negate the very benefits of containment of bodily liquids that the absorbent article is intended to provide. Similarly, if an absorbent article is applied properly but then must be loosened in order to facilitate the removal and/or the insertion of such an absorbent core component, not only is the same unacceptable leakage likely to occur, but the proper fit of the absorbent article on the torso of the wearer is likely to be difficult to restore. In addition, such loosening, manipulation of the absorbent core component through the wearer's crotch, and restoration of the fit by tightening the absorbent article, is very likely to be annoying to the wearer and, therefore, difficult for the caregiver to accomplish. Hence, the removable absorbent core components and absorbent inserts known in the art that extend from one waist region through the crotch region to the opposing waist region are typically intended to be removed only when the absorbent article has been opened and/or removed from the body of the wearer, rather than while the absorbent article is being worn. In the few instances where such a removable absorbent core component is asserted to be removable while the article is being worn, no assertion is made of the impractical contention that a like replacement core component can be inserted.

In particular, it is preferred that the front panel or the back panel of the absorbent core of the present invention extend from the respective waist region into the crotch region no farther than the crotch point of the absorbent article. Thus, the front panel and the back panel are particularly well suited for use as replaceable core components. Because each of these panels extends only from a waist region into the crotch region, but not through the crotch region to the opposing waist region, it can be removed and replaced without the necessity of passing any portion of the panel, the fingers or hand of the caregiver, or an insertion tool through the wearer's crotch. Nevertheless, because the inner end of each of these panels can be shaped to fit comfortably into the crotch area of the wearer's body, as described above, the inner end can be optimally positioned for the absorption of liquid from the center section, i.e., from the non-removable core component that extends through the wearer's crotch and thus can serve to transport liquid from the front waist region to the back panel or from the back waist region to the front panel.

Figure 12:
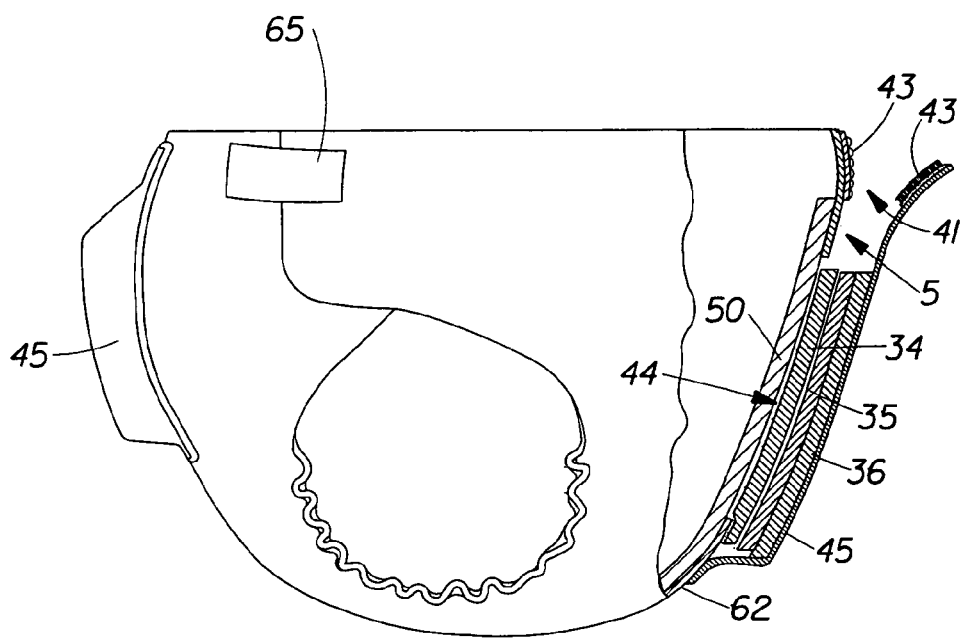
FIG. 12 is a side view, showing in partial cross-section, another alternative exemplary absorbent article.

The center section may include multiple layers of absorbent material, each having individual liquid acquisition, acquisition/distribution or storage/redistribution characteristics, as well as individual shape, width, length and thickness characteristics. The number and placement of absorbent layers of the center section may be varied to achieve desired characteristics such as thinness, softness, flexibility, or beneficial liquid acquisition, distribution, and storage rates. For example, the layers of the center section need not extend from one waist region through the crotch to the opposing waist region. In particular, the center section may include an absorbent layer extending from one waist region into the crotch region, where it ends, and another absorbent layer extending from the opposing waist region into and ending in the crotch region. The number of absorbent layers of the front and back panels may also be varied to achieve desired characteristics such as beneficial liquid acquisition and distribution rates, as well as capacity and storage rates, and wearer comfort. For example, in FIG. 3, the absorbent core is shown with the center section 50 and the front and back panels 20 and 30 each having a single absorbent layer. However, the center section has three absorbent layers in the exemplary embodiments shown in FIG. 2 and FIG. 5, with two absorbent layers designated 51 and one absorbent layer designated 52. Also, the back panel is shown in FIG. 12 as a core component made up of back panel absorbent layers 34, 35, and 36.

Figure 7:
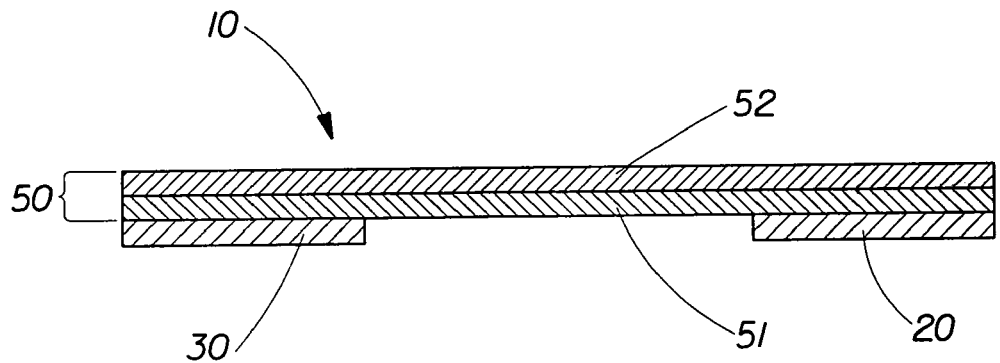
FIG. 7 is a sectional view of an exemplary absorbent core similar to that shown in FIG. 6, taken along line 7-7, with the portion of the core that faces the wearer oriented upward.

In the exemplary embodiment shown in cross section in FIG. 7 and corresponding to the general top view of FIG. 6, one upper absorbent layer 52 and one lower absorbent layer 51 are both placed over front and back panels 20 and 30, resulting in a thin, flexible absorbent core. The term "over" refers to the surface of the absorbent core of the invention corresponding to the wearer's body when used in an absorbent article such as a disposable diaper, i.e., the body-facing surface. It is noted, however, that FIG. 7 is representative of only one exemplary embodiment and it may be beneficial to place the absorbent layers 51 or 52 under the front and back panels 20 and 30. The term "under" refers to the surface of the absorbent core of the invention corresponding to the garment side when used in an absorbent article such as a catamenial pad or disposable diaper, i.e., the garment-facing surface. It should also be understood that the term "upper" refers to the absorbent layer of the absorbent core which is nearest to and faces the article topsheet; conversely, the term "lower" refers to the absorbent layer of the absorbent core which is nearest to and faces the article backsheet.

Figure 8:
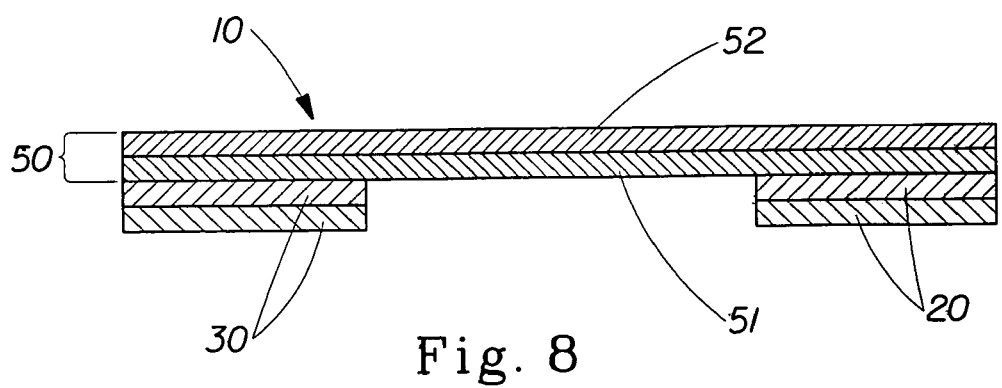
FIG. 8 shows a sectional view of another alternative exemplary absorbent core, with the portion of the core that faces the wearer oriented upward.
Figure 9:
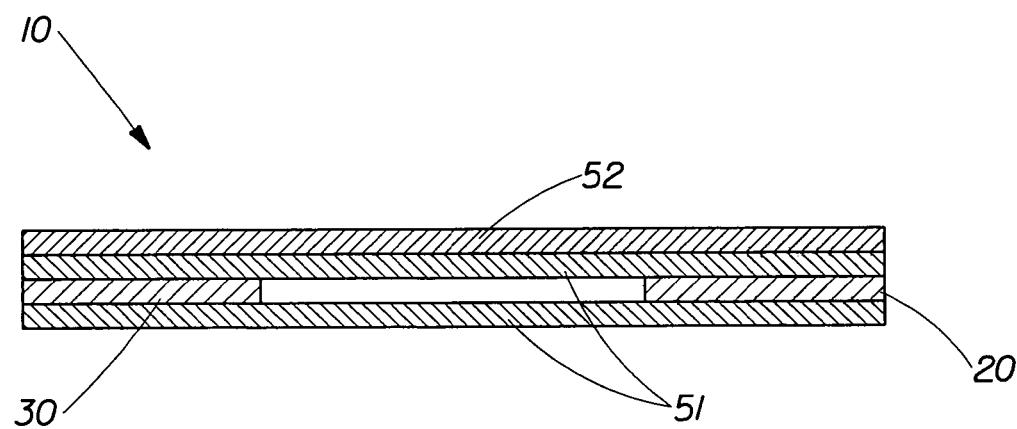
FIG. 9 shows a section view of another alternative exemplary absorbent core, with the portion of the core that faces the wearer oriented upward.
Figure 10:
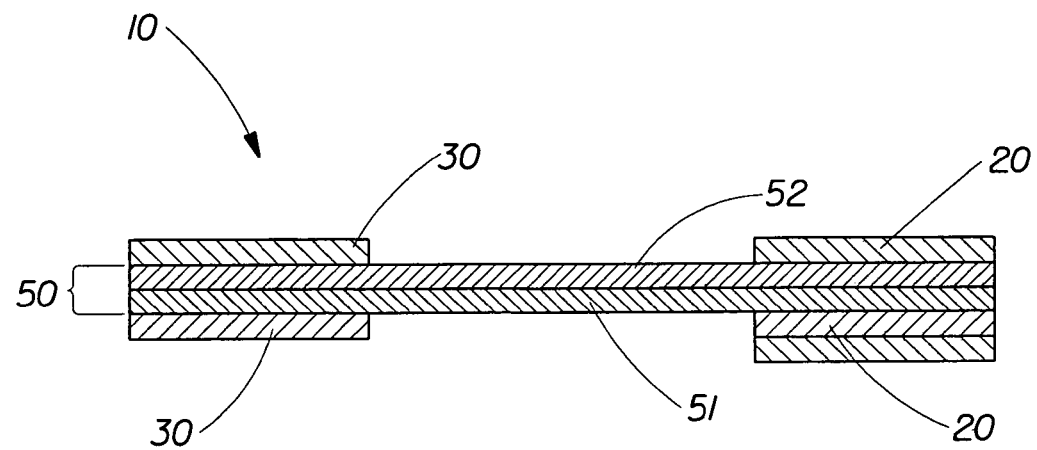
FIG. 10 shows a section view of another alternative exemplary absorbent core, with the portion of the core that faces the wearer oriented upward.

Other arrangements of the absorbent layers of the center section and the front and back panels are also possible. For example, FIG. 8 shows in cross-section an additional exemplary embodiment corresponding to the general top view of FIG. 5, in which two absorbent layers of front and back panels 20 and 30 are placed under the center section 50. As shown in the Weber et al. '602 patent and in FIG. 9, an alternative embodiment may have a center section 50 having two absorbent layers 51, one placed over front and back panels 20 and 30, and one placed under the front and back panels, thereby sandwiching the front and back panels between absorbent layers of the center section. As another example, as shown in the Weber et al. '602 patent and in FIG. 10, the front and back panels 20 and 30 may have two absorbent layers, with one absorbent layer placed over the center section 50 and one absorbent layer placed under the center section 50, thereby sandwiching the ends of the center section between absorbent layers of the front and back panels.

As shown in FIG. 7, the uppermost absorbent layer 52 is generally on the side corresponding to the body side of an absorbent article, such as a disposable diaper. Therefore, the uppermost absorbent layer 52 is generally in capillary liquid communication with topsheet 61 of the disposable diaper, thereby acting to quickly acquire and partition bodily exudates away from the wearer's body to the generally more absorptive lower absorbent layers 51 and to the front and back panels 20 and 30. Adhesive bonding of the uppermost absorbent layer 52 to the topsheet 61 may enhance the capillary liquid communication by providing interfacial bonding and preventing topsheet separation from impeding liquid flow.

The Absorbent Core Materials

The components or members of the absorbent core may include laminates or combinations of several sheets or webs of the requisite types of materials. In general, each absorbent core component or member may be made of any absorbent material or combination of materials having enough structural integrity to be handled as a discrete unit.

For example, in order for a non-removable core component, such as the center section, to function properly in use, it is preferable to maintain the structural integrity of the component in order to maintain its ability to transport liquid from the front of the absorbent article to the rear of the absorbent article and/or from the crotch region of the absorbent article to the waist regions. If an absorbent layer of the non-removable core component is torn or fractured, the liquid transport and capillary liquid communication with the replaceable core component can be interrupted. Therefore, it is preferred that, when dry, the absorbent layer or layers of the non-removable core component have a tensile strength to break of greater than about 200 grams force and, more preferably, greater than about 400 grams force and, most preferably, greater than about 1000 grams force. It is also preferred that, when completely wetted, the absorbent layer or layers of the non-removable core component have a tensile strength to break of greater than about 100 grams force and, more preferably, greater than about 200 grams force and, most preferably, greater than about 400 grams force. The structural integrity can also be achieved by affixing a carrier layer having the required tensile to break characteristics to the non-removable core component or to the absorbent layer along its major surfaces or, alternatively, by wrapping the non-removable core component or the absorbent layer in the carrier layer.

Typical materials known in the art may be used for the absorbent core components and/or members, such as fibrous nonwoven materials, fibrous air-laid materials, fibrous wet-laid web materials, and combinations of fibrous materials having absorbent gelling materials dispersed upon or within the fibrous structure. If necessary, such absorbent core components or members may be formed into a packet having the fibrous materials substantially enveloped by a liquid pervious web that provides the structural integrity for the removal and replacement into the absorbent article. An exemplary form of a non-woven fibrous absorbent structure that may be utilized in the present invention is constructed from hydrophilic chemically stiffened cellulosic fibers, as taught in the Lash '728 patent and the Young et al. '345 patent, as well as in the Seger et al. '416 patent.

Absorbent materials for use as absorbent core components or members may also be foam-based. For example, a component of the absorbent core may include a foam material in the form of a sheet or a plurality of foam pieces or particles, which may be adhesively bonded together or which may simply be constrained into an unbonded aggregate held together by an overwrapping of envelope tissue or by means of the topsheet and backsheet of the absorbent article. Particularly suitable absorbent foams for absorbent articles such as diapers have been made from High Internal Phase Emulsions, hereafter referred to as "HIPE". See, for example, the DesMarais et al. '345 patent, the DesMarais et al. '224 patent, and the Stone et al. '179 patent.

The absorbent core of the absorbent articles described herein can also include a combination of conventional elements or materials and one or more foam absorbent structures. For example, the absorbent articles may utilize an absorbent core which includes a combination, e.g., an airlaid mixture, of particles or pieces of the foam absorbent structures and conventional absorbent materials such as wood pulp or other cellulosic fibers and/or particles or fibers of polymeric gelling agents.

Besides acquiring bodily liquids rapidly, the absorbent acquisition member of the present invention should give up this liquid efficiently to the liquid acquisition/distribution or storage/redistribution members. This liquid transfer function of the acquisition member is of particular importance because the acquisition member must have sufficient capillary suction to substantially drain the liquid from the topsheet and yet not exhibit excessive liquid retention, which would make it difficult for the underlying absorbent layer to desorb the acquisition member.

In particular, the liquid acquisition member should have a suitable capillary desorption pressure relative to the absorption pressure of other absorbent core members, especially those intended for liquid storage. If the liquid acquisition member of the absorbent article holds the acquired liquid too tenaciously, this will inhibit the ability of these other members to partition liquid away and can cause the acquisition member to remain so heavily loaded with liquid that the absorbent article is more susceptible to leaking.

This principle, according to which the relationship of the capillary absorption pressure of one absorbent element and the capillary desorption pressure of another absorbent element defines the liquid flow, liquid transfer, and capillary liquid communication characteristics of the absorbent article, is that of a capillary cascade. For example, the wearer-facing layer of the absorbent article, e.g., a topsheet, is liquid pervious and has particular capillary absorption and desorption pressures. The capillary desorption pressure of this topsheet is preferably less than the capillary absorption pressure of the non-removable core component and, specifically, less than the capillary absorption pressure of the uppermost absorbent layer of the non-removable core component, with which the topsheet will be in contact. It is also preferred that the capillary absorption pressure of an intermediate or lowermost absorbent layer of the non-removable core component is greater than the capillary desorption pressure of the topsheet.

In addition, it is preferred that the absorption pressure of a lower absorbent layer of the non-removable component be greater than the capillary desorption pressure of the uppermost absorbent layer of the non-removable core component. Furthermore, it is preferable that the capillary absorption pressure of the storage/redistribution member of the replaceable core component be greater than the capillary desorption pressure of the absorbent layer of the non-removable core component in contact with the replaceable core component.

In addition to having to overcome the capillary desorption pressure of an adjacent absorbent structure, an absorbent layer must overcome the difference in vertical height between a source of liquid and the portion of the absorbent layer to which it is desired to move the liquid by capillary transport. The magnitude of this vertical head may be on the order of 15 cm to 20 cm in some embodiments of the present invention, in which liquid is moved from the lower portion of the crotch region to the upper waist region of an absorbent article worn by a standing wearer, is moved from the front portion to the back panel of an absorbent article worn by a wearer lying in a face-down posture, or is moved from the back portion to the front panel of an absorbent article worn by a wearer lying in a face-up posture.

As an example of a suitable capillary cascade relationship, in some exemplary embodiments, it is preferred that the uppermost absorbent layer of the non-removable core component have a capillary absorption pressure of between 2 cm and 10 cm and a capillary desorption pressure of between 5 cm and 25 cm. A lower absorbent layer of this non-removable core component preferably has a capillary absorption pressure of between 10 cm and 40 cm and a capillary desorption pressure of between 20 cm and 60 cm and is thereby capable of desorbing liquid from the uppermost absorbent layer. For embodiments in which the non-removable core component includes only a single absorbent layer of material or a stratified structure, the capillary absorption pressure of the non-removable core component is preferably between 2 cm and 40 cm and the capillary desorption pressure is between 5 cm and 60 cm.

The liquid acquisition/distribution member may include materials similar to those used in the acquisition member, but preferably having more distributive characteristics. Since discharged aqueous bodily liquid, e.g., urine, is frequently discharged in gushes, the acquisition/distribution member must be able to quickly acquire this liquid and must also transport the liquid by wicking or another mechanism from the point of initial liquid loading to other parts of the acquisition/distribution member for eventual desorption to the adjacent liquid storage/redistribution member. Thus, such materials preferably have a greater degree of distributive capacity than the acquisition member materials, such that bodily exudates may be efficiently transported from the acquisition zone to the storage members of the absorbent core.

In some embodiments, it may be desirable to have a "biased" absorbent core structure, wherein a portion adjacent to one surface is capable of rapidly acquiring a liquid with minimal dispersion, while a portion adjacent to an opposing surface is capable of rapidly dispersing a liquid with lesser acquisition capability. When oriented in an absorbent article such that the "acquisition side" is oriented toward the wearer and the "distribution side" is oriented away from the wearer, a "down and out" functionality is provided, whereby liquid is rapidly acquired into the absorbent core structure with minimal dispersion on its wearer-facing side and is rapidly distributed throughout the portion of the absorbent core structure on its garment-facing side. This functionality allows the maintenance of a clean and dry visible and tactile impression of the absorbent core structure, and hence the absorbent article, while effectively utilizing the absorptive capacity of the regions of the absorbent article oriented away from the wearer.

In order to provide the above-described functionality in some exemplary embodiments, compositions for the absorbent core may be selected such that the acquisition side of the absorbent layer is comparatively free of small, high surface area fibers which provide good distributive and storage characteristics but less than optimal acquisition characteristics and such that the distributive side of the absorbent layer has a comparatively higher proportion of such small, high surface area fibers so as to provide greater distribution characteristics. In some embodiments, the acquisition area may have both a relatively lower average density and lower average basis weight per unit area than the distribution area to establish the preferred capillarity force gradient between them. Also, in foam absorbent core structures, cell sizes and hole sizes are parameters that can impact a number of important mechanical and performance features of the foams, including their fluid wicking properties and the capillary pressure that is developed within the foam structure, as described in the Stone '179 patent.

Optionally, a liquid pervious sheet, e.g., a tissue sheet, or a scrim layer is positioned between the acquisition/distribution member and the storage/redistribution member to maintain the physical integrity of the acquisition/distribution member during processing and/or use. This liquid pervious sheet can envelop all or part of the acquisition/distribution member, or simply be positioned as described above, without necessarily enveloping the acquisition/distribution member. In embodiments in which the center section of the absorbent core includes the acquisition and acquisition/distribution members and is placed over or under a replaceable absorbent core component or absorbent insert including the storage/redistribution member, such as a back panel, a single such liquid pervious sheet may suffice. Alternatively, in embodiments in which absorbent layers of the center section sandwich the replaceable absorbent core component or absorbent insert, two or more such liquid pervious sheets may be positioned to separate the absorbent layers of the center section and the replaceable core component. These multiple liquid pervious sheets may be described as forming a surface of or lining the openable chassis pocket formed by and between the sandwiching absorbent layers of the center section. Similarly, in embodiments in which absorbent layers of a replaceable absorbent core component or absorbent insert sandwich an end of the center section, two or more such liquid pervious sheets may be positioned to separate the absorbent layers of the center section and the replaceable core component. In the latter embodiment, the multiple liquid pervious sheets may be described as forming a surface of or lining the two-part openable chassis pocket into which the replaceable absorbent core component or absorbent insert is inserted and which is formed by and between the topsheet and the center section and by and between the center section and the backsheet, respectively.

An absorbent core suitable for use with the present invention includes at least one absorbent core component including a liquid storage/redistribution member and may include two such components, e.g., in the form of front and back panels. Each absorbent core component having a liquid storage/redistribution member acts to store bodily exudates away from the wearer's body, so as to leave the wearer with a feeling of dryness and to prevent leakage. The absorbent core component having the liquid storage/redistribution member is maintained in capillary liquid communication with the acquisition and/or acquisition/distribution member(s), such that urine or other aqueous bodily liquid can be desorbed from the acquisition and/or acquisition/distribution member(s) and be absorbed by the liquid storage/redistribution member.

The storage/redistribution member may include a member or members having primarily liquid storage characteristics. Such a storage member may have limited transport and wicking capabilities but high storage or retention capacity, and rely upon a liquid distribution member to distribute incoming liquid over a larger area of the storage/redistribution member.

In order for a replaceable core component such as the back panel to function well within the context of the present invention, an absorbent layer of the replaceable core component preferably has an absorption pressure that is sufficient to desorb liquid from an acquisition/distribution member of a non-removable absorbent core component such as the center section, i.e., the absorption pressure of the absorbent layer of the replaceable core component is preferably greater than the desorption pressure of the acquisition/distribution member. Therefore, the absorbent layer of the replaceable core component preferably has an absorption pressure of between 25 cm and 80 cm. An exemplary material capable of providing absorption pressures within the specified range is a collapsed polymeric foam material comprising a hydrophilic, flexible, nonionic polymeric foam structure of interconnected open cells, which foam material, upon contact with body temperature liquid, expands and absorbs the liquid. An important parameter of these foams is their glass transition temperature. The glass transition temperature represents the midpoint of the transition between the glassy and rubbery states of the polymer. Foams that have a higher glass transition temperature than the temperature of use can be very strong but will also be very rigid and potentially prone to fracture. When such foams are collapsible, but have been stored in the collapsed state for prolonged periods, they also typically take a long time to recover to the expanded state when wetted with aqueous fluids colder than the glass transition temperature of the polymer. Such a foam may have a capillary suction specific surface area per gram in the range from about 0.7 to about 8 $m^2/g$ or, preferably, from about 1 to about 7 $m^2/g$, and most preferably from about 1.5 to about 6 $m^2/g$. Such a foam will preferably have a number average cell size of about 50 microns or less and typically in the range of from about 5 to about 50 microns. More preferably, the number average cell size will be in the range from about 5 to about 40 microns and, most preferably, from about 5 to about 35 microns.

The absorbent articles of the present invention are preferably constructed such that when liquid is deposited in the article, the liquid is quickly absorbed and transported from the non-removable core component to the replaceable core component. In order to minimize the bulk of the absorbent article and to maximize the benefits of skin health and dryness, it is preferable that the non-removable core component have a liquid storage capacity that is low relative to the total capacity of the absorbent core, i.e., relative to the total of the summed capacities of the non-removable and replaceable core components. Furthermore, it is desirable to remove the majority of the liquid deposited in the article by removing the replaceable core component and replacing it with a fresh dry component. Therefore, it is preferred that the liquid absorptive capacity of the replaceable core component be significantly greater than the liquid absorptive capacity of the non-removable core component. The liquid absorptive capacity of the replaceable core component is preferably at least about 1.5 times as great as the liquid absorptive capacity of the non-removable core component, more preferably at least about 2 times as great, and most preferably at least about 4 times as great as the liquid absorptive capacity of the non-removable core component.

The replaceable core component may include an absorbent layer including an acquisition material, which may be the same material as the uppermost absorbent layer of the non-removable core component. This acquisition material may form a portion of the outer surface of the replaceable core component or, alternatively, the acquisition material may be disposed under another layer of liquid pervious material. The absorbent layer of the replaceable core component including the acquisition material may be disposed in capillary liquid communication with the topsheet or in capillary liquid communication with a portion of the non-removable core component.

In some embodiments, the replaceable core component may include an absorbent layer including a distribution material, which may be the same material as that in an intermediate or a lower absorbent layer of the non-removable core component. This distribution material may form a portion of the outer surface of the replaceable core component or, alternatively, the distribution material may be disposed under another layer of liquid pervious material. The distribution material may be disposed adjacent to either the wearer-facing surface of the replaceable core component or the garment-facing surface of the replaceable core component, or both. Furthermore, the distribution material may be in capillary liquid communication with the topsheet or in capillary liquid communication with a portion of the non-removable core component.

The replaceable core component may include multiple absorbent layers or pieces, including at least a liquid storage member and/or a liquid storage/redistribution member. The replaceable core component may also have one or more layers forming a packet to partially or completely contain the absorbent layer or layers. The packet layers may include liquid pervious materials, liquid impervious materials, or combinations thereof, and at least a portion of one of the packet layers forming the outer surface of the replaceable core component must have a liquid pervious region. In some embodiments, an outer surface of the replaceable core component may be formed by an acquisition member, a distribution member, or an acquisition/distribution member disposed in such a way as to contain the absorbent layer or layers in which the liquid storage member and/or the liquid storage/redistribution member is included. Also, in some embodiments, these additional absorbent members may be disposed between the packet layers forming the outer surface of the replaceable core component and the storage or storage/redistribution member.

In summary, the absorbent core 10 includes a plurality of discrete components, each component having distinct liquid acquisition, acquisition/distribution, or storage/redistribution characteristics. So long as each of the acquisition, acquisition/distribution, and storage/redistribution members is in capillary liquid communication with an adjacent member or members, the absorbent core components may be positioned relative to one another in a wide variety of configurations. There is no particular criticality with respect to the positional relationship of the acquisition/distribution member and the liquid storage/redistribution member within the absorbent core so long as these members are in effective capillary liquid communication with each other and so long as each member is capable of effectively holding and/or transporting the amount of aqueous bodily liquid that is expected to be discharged into the absorbent article. It should be noted that the various structures of absorbent articles according to the present invention may or may not be generally planar in nature, and may be shaped or profiled in any desired configuration.

The Structure Allowing Removal and Replacement of Core Components

52 As shown in FIG. 2, FIG. 3, and FIG. 4, the backsheet 62 of some exemplary embodiments of an absorbent article of the present invention may have an aperture 44 in the general proximity of the front panel 20 or rear panel 30, or both.

As shown in FIG. 4, the aperture 44 provides access into what may be described as an openable chassis pocket 5, with a removable absorbent core component, for example, the back panel 30, being disposed inside the openable chassis pocket when the diaper is being worn, and being removable from and replaceable into the openable chassis pocket through the aperture. For example, after the removal of a saturated back panel, a fresh, unused absorbent core component may be reinserted through the aperture. A flap 42 may be provided to cover the aperture. The material used for the backsheet may be used for the flap as well. When the disposable diaper is being worn, the flap may be secured over the aperture by suitable fasteners 43, such as VELCRO strips or adhesive strips (not shown). For example, FIG. 4 shows the flap in the closed position over the aperture adjacent to the front panel 20 (shown in FIG. 3). More preferably, the flap is sealed with releasable adhesive, thereby providing for liquid impermeability when closed, but allowing for multiple openings and closings.

In the exemplary embodiment shown in FIG. 3 and FIG. 4, the back panel 30 is disposed under the center section, as in the description of FIG. 7, above, and the openable chassis pocket 5 is formed by and between the center section 50 and the backsheet 62. In other exemplary embodiments, in which the center section and the removable core component or components are arranged differently, the openable chassis pocket may be formed by and between different components and layers. For example, in an embodiment in which the back panel is disposed above the center section, the openable chassis pocket may be formed by and between a topsheet and the center section. Similarly, when the back panel is sandwiched between absorbent layers of the center section, as in FIG. 9, the openable chassis pocket may be formed by and between the sandwiching absorbent layers of the center section. Also, when the center section is sandwiched between absorbent layers of the back panel, as in FIG. 10, the openable chassis pocket may be formed in two parts, by and between the topsheet and the center section and by and between the center section and the backsheet, respectively.

In general, the front panel, the back panel, and the corresponding apertures and flaps are substantially similar, but need not be. In an alternative exemplary embodiment, it may be desired to include only one aperture and flap, for example, for access to the back panel, without providing a similar aperture for access to the front panel.

Figure 11:
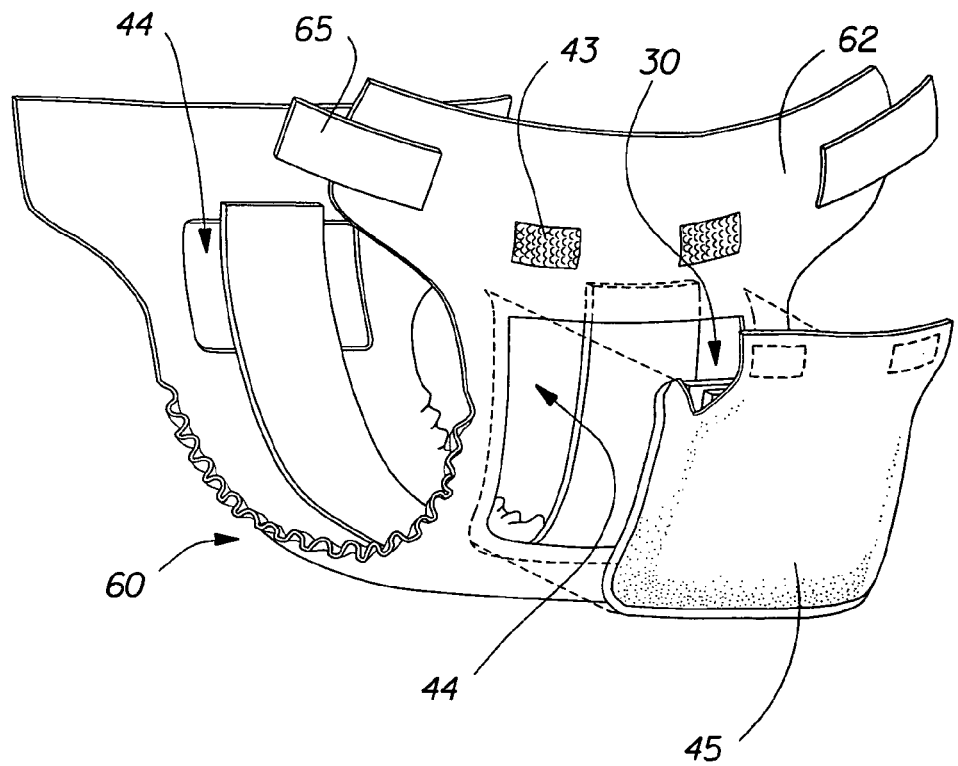
FIG. 11 is an exploded, perspective, partially segmented illustration of an alternative exemplary absorbent article according to the present invention.

Alternatively, as shown in FIG. 11 and FIG. 12, a backsheet pocket sheet 45 may be affixed on the garment-facing surface of the backsheet adjacent to the aperture 44 to form an openable chassis pocket 5 between the backsheet pocket sheet and the backsheet. In these embodiments, a removable and replaceable core component, such as back panel 30, may be disposed outside, relative to the aperture, and a core component that remains in the absorbent article, i.e., a non-removable core component, such as center section 50, may be disposed inside, relative to the aperture, such that the aperture allows capillary liquid communication between the replaceable core component and the non-removable core component.

The openable chassis pocket 5 formed by the backsheet pocket sheet 45 may have its openable end 41 longitudinally nearest the adjacent waist end edge. The openable chassis pocket may be reclosable and may be resealable, and is preferably positioned so that the back panel is urged into capillary liquid communication with the center section. The backsheet pocket sheet is preferably resilient and pliable, and forms a substantially liquid impervious barrier over the aperture, functionally becoming an extension of the backsheet when the openable chassis pocket is closed.

The back panel is shown in FIG. 12 as a core component made up of individual back panel absorbent layers 34, 35, and 36. In such an embodiment, as one back panel absorbent layer, e.g., the uppermost back panel absorbent layer 34, becomes saturated with bodily discharge it may be removed, thereby exposing an adjacent prepositioned back panel absorbent layer, e.g., the adjacent back panel absorbent layer 35.

Figure 13:
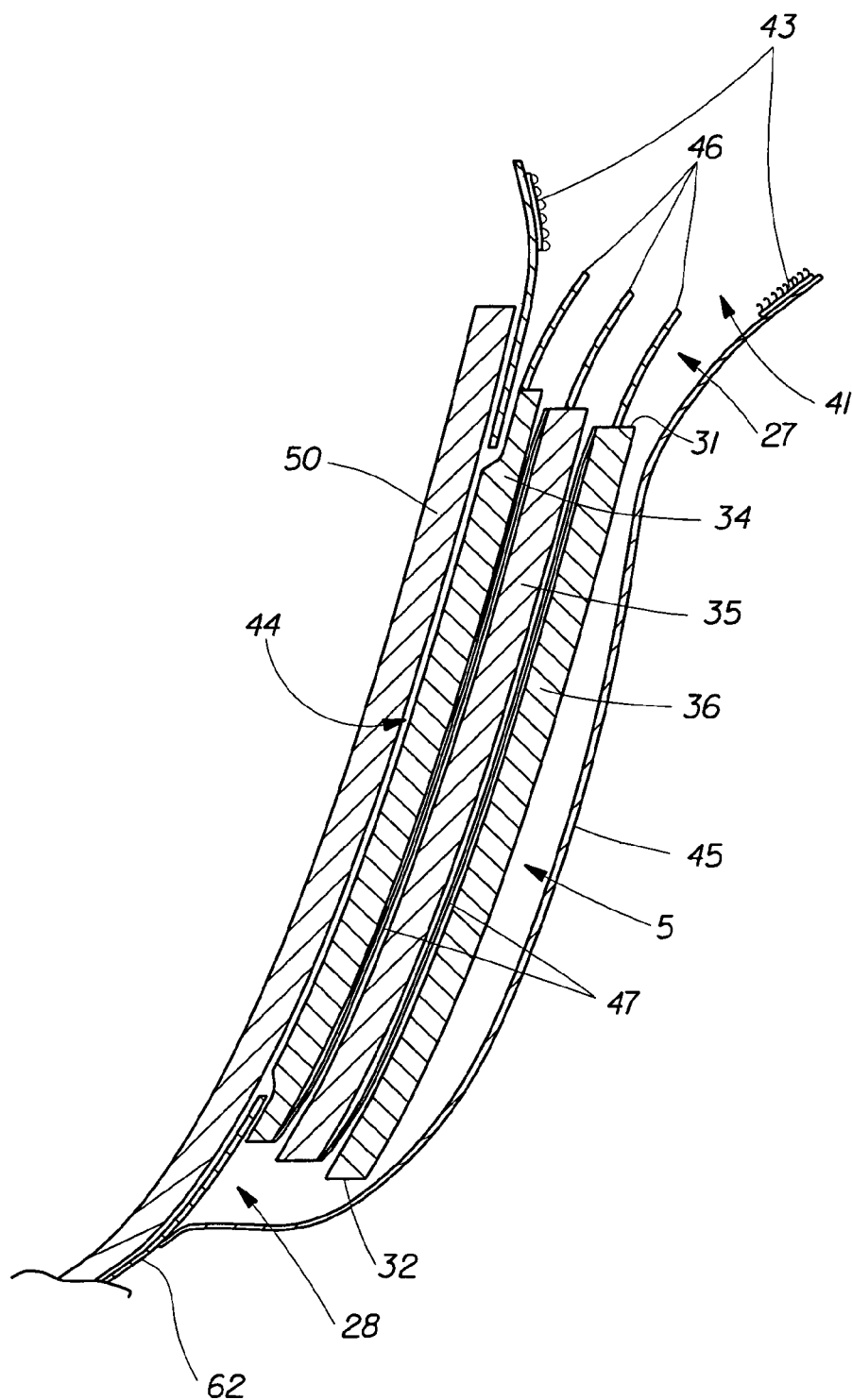
FIG. 13 is a cross-section illustration of a portion of an exemplary absorbent article having an opening through the backsheet.

FIG. 13 shows an exemplary embodiment of the arrangement of the back panel 30, again showing representative back panel absorbent layers 34, 35, and 36 in a layered relationship adjacent to the aperture 44 and in capillary liquid communication with the center section 50. Removal of the back panel absorbent layers through the openable end 41 of the openable chassis pocket 5 may be facilitated by the use of pull tabs 46, which may be of any type known in the art, such as a strip of plastic film adhered to each back panel absorbent layer.

Additionally, the back panel absorbent layers may be separated from one another by a liquid impervious blocking layer 47 so that adjacent back panel absorbent layers are not in capillary liquid communication with each other. The blocking layer 47 may be any liquid impervious polymer film, such as film suitable for use as a liquid impervious backsheet. As one back panel absorbent layer becomes saturated by absorption of liquid from the center section 50, it may be removed, thereby exposing a substantially dry, fresh adjacent back panel absorbent layer for additional absorption from the center section 50. In this manner, the absorbent article may be refreshed or regenerated for a prolonged period of time without the necessity of its removal from the wearer.

Figure 14:
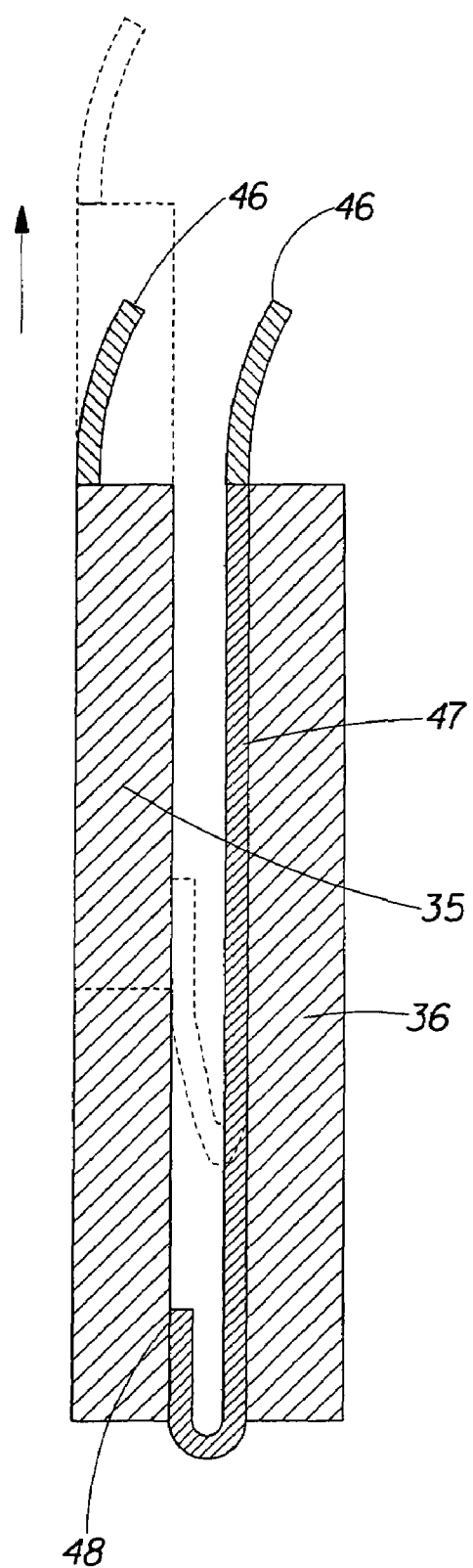
FIG. 14 is a cross-section detail of an exemplary configuration of removable and replaceable absorbent core layers.

FIG. 14 shows an exemplary arrangement of the back panel absorbent layers 35 and 36 in a layered relationship with the liquid impervious blocking layer 47 disposed to form a liquid impervious layer between them. A portion of the blocking layer is preferably affixed, for example at an attachment point 48, to the back panel absorbent layer being removed. As this back panel absorbent layer 35 is removed, the blocking layer 47 is removed as well, thereby leaving the adjacent back panel absorbent layer 36 in position to be urged into capillary liquid communication with the center section 50.

Figure 15:
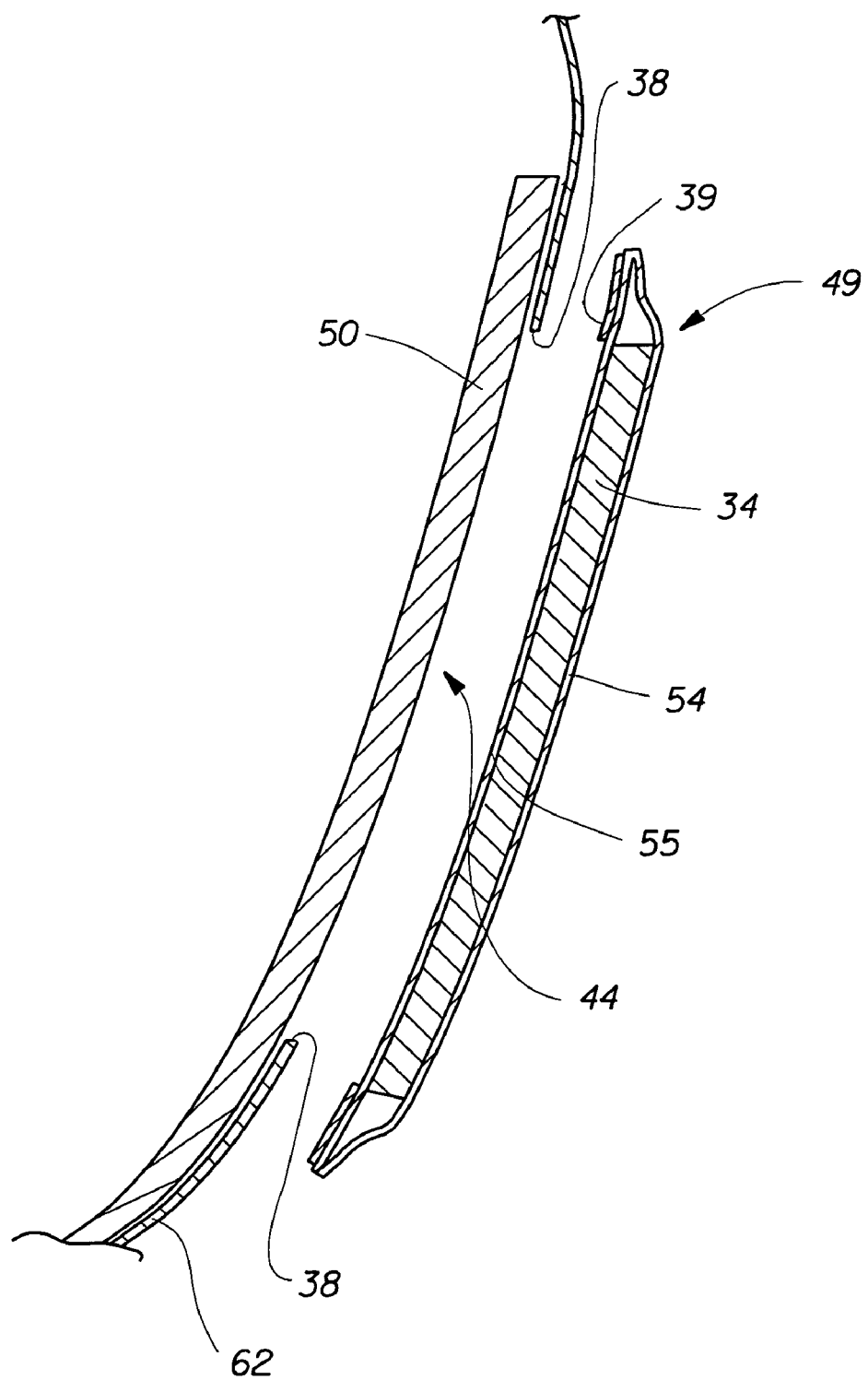
FIG. 15 is a cross-section detail of an alternative exemplary configuration of a removable and replaceable absorbent core component.

An alternative exemplary embodiment of the back panel 30 of an absorbent article of the present invention is shown in cross-section in FIG. 15, in which a back panel envelope 49 is shown in position to be attached to the backsheet 62. The back panel envelope is shown as containing a single back panel absorbent layer 34 enveloped between a substantially liquid impervious layer 54 and a substantially liquid pervious layer 55, and may be releasably affixed, for example, by a suitable releasable adhesive 39 known in the art, adjacent to the perimeter 38 of the aperture 44. When such a releasably affixed back panel envelope becomes saturated due to the absorption of liquid from the center section 50, it may be removed and replaced with a fresh, dry back panel envelope 49.

Figure 16:
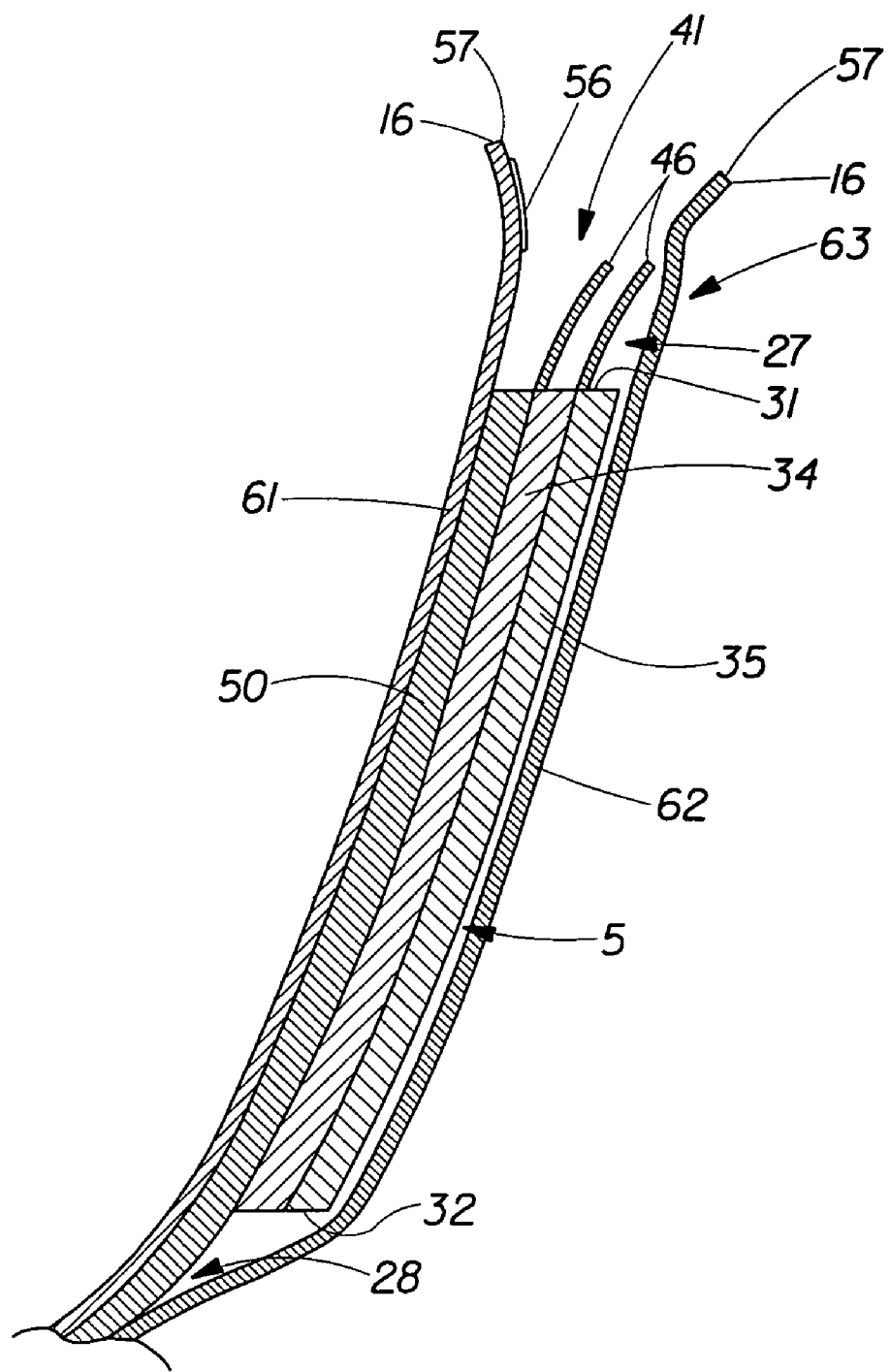
FIG. 16 is a cross-section depiction of an additional alternative exemplary configuration of removable and replaceable absorbent core layers.

In another alternative exemplary embodiment of an absorbent article of the present invention shown in cross-section in FIG. 16, the openable end 41 of the openable chassis pocket 5 may be formed along a predetermined area of the periphery 57, such as along the waist end edge 16, either in the front, in the back, or both, where the topsheet 61 and the backsheet 62 are separable to provide access to the removable absorbent core component, e.g., the back panel absorbent layers 34 and 35. The openable end formed by the separation of the topsheet and the backsheet allows the removal and replacement of the removable absorbent core components and may be resealable to provide a substantial degree of liquid impermeability when closed. The openable end may be made resealable, for example, with a suitable releasable and resealable adhesive 56 known in the art.

As can be seen in FIG. 13 and in FIG. 16, the openable chassis pocket 5 generally has an outer end 27 and an inner end 28 corresponding to the outer end 31 and the inner end 32, respectively, of the back panel 30. In the exemplary embodiments shown in FIG. 13 and FIG. 16, the outer end 27 of the openable chassis pocket coincides with its openable end 41. The inner end of the openable chassis pocket may be formed in several ways. For example, as shown in FIG. 13, the inner end may be formed at the area of attachment of the backsheet pocket sheet 45 to the backsheet. As described above, the backsheet, the topsheet, and the non-removable absorbent core component may be secured, attached, or affixed to each other in a variety of configurations. Thus, as another example of the formation of the inner end of the openable chassis pocket, an area of attachment of the non-removable absorbent core component to the chassis, e.g., to the backsheet, the topsheet, or both, in the crotch region may form the inner end of the openable chassis pocket.

Figure 17:
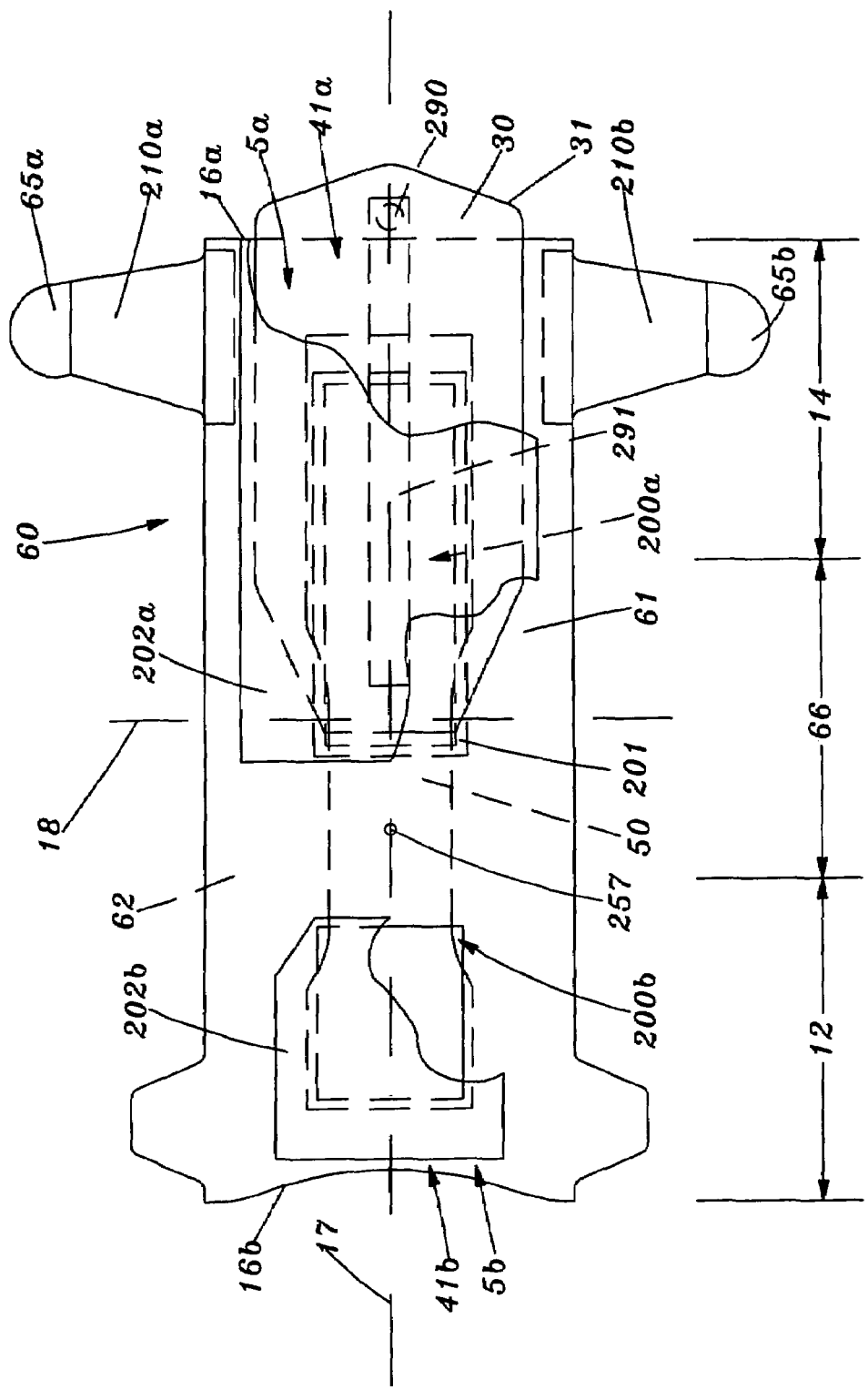
FIG. 17 is a plan view of another exemplary diaper of the present invention in its flat-out, uncontracted state, i.e., with all elastic induced contraction pulled out, with portions of the structure being cut away to more clearly show the construction of the diaper, and with the portion of the diaper that contacts the wearer facing the viewer, showing an apertured topsheet.
Figure 18:
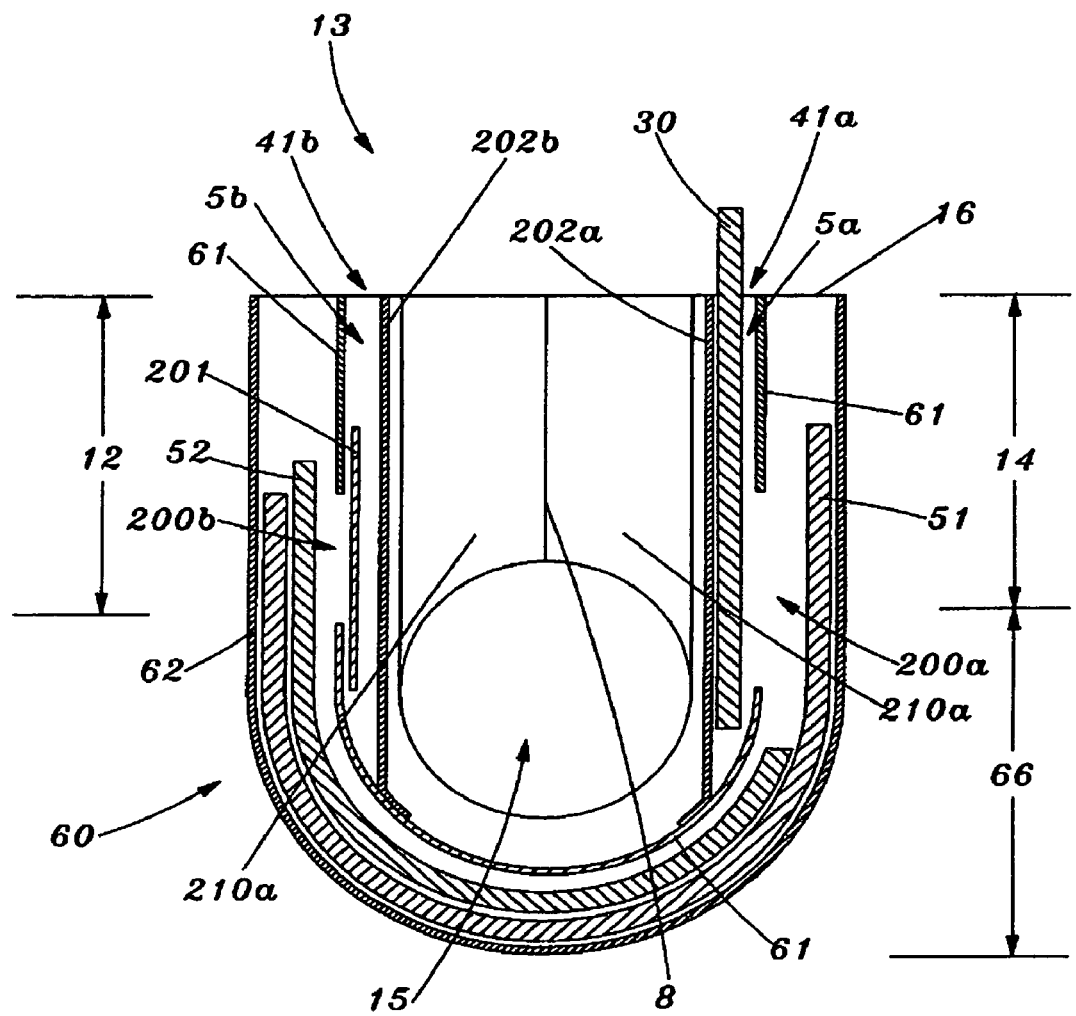
FIG. 18 is a cross-section view of an exemplary pants-type diaper having an apertured topsheet.

In alternative embodiments, as shown in FIG. 17 and FIG. 18, a topsheet pocket sheet 202 may be affixed on the wearer-facing surface of the topsheet 61 to form an openable chassis pocket 5 between the topsheet pocket sheet and the topsheet. The openable chassis pocket 5 formed by the topsheet pocket sheet 202 may have its openable end 41 adjacent to the nearest waist end edge 16. The openable chassis pocket may be reclosable and may be resealable, and is preferably positioned so that an inserted back panel is urged into capillary liquid communication with the center section. The topsheet pocket sheet is preferably resilient, pliable, and liquid pervious and may be formed of the same material as the topsheet.

As is also shown in FIG. 17 and in FIG. 18, in some exemplary embodiments having such an openable chassis pocket 5 formed by a topsheet pocket sheet 202, the topsheet 61 may have a topsheet aperture 200 allowing face-to-face contact and capillary liquid communication between a replaceable absorbent core component disposed in the openable chassis pocket, such as the back panel 30, and a non-removable absorbent core component, such as the center section 50, disposed adjacent to an opposing surface of the topsheet. Such a topsheet aperture may have an area of approximately 1 cm$^2$ or greater, and a smaller of its length and width dimensions may be approximately 5 mm or greater. Such a topsheet aperture may have a generally rectangular shape, a generally circular shape, or any other geometric shape having a ratio of smallest dimension to greatest dimension of from 1:1 to approximately 1:100, including all intermediate ratios. In some exemplary embodiments, such a topsheet aperture may be covered with a layer of a permanently hydrophilic fibrous material. This topsheet aperture covering layer 201 may be formed of fibers that are naturally hydrophilic or of fibers that have been treated to make them permanently hydrophilic in the sheet structure. Alternatively, the topsheet aperture may be covered with a mesh having openings sufficiently large to allow the direct face-to-face contact of the absorbent layers disposed on either side of the topsheet. Suitable non-limiting examples of materials that can be used to cover the topsheet aperture include a permanently hydrophilic non-woven available from SciMAT Limited of Swindon, U.K. under product code 900/20, a mesh material such as a 100% nylon netting available from WYLA, Inc. of New York, N.Y., U.S.A. under product designation RT80, and a tissue such as a cellulose tissue available from Georgia-Pacific Corporation of Atlanta, Ga., U.S.A. under the designation of 65588. Another suitable material for use as the topsheet aperture covering layer comprises a bonded structure of curly cellulosic fibers, which may also include high surface area fibers as described herein.

As described in the chassis description, an elastic waistband 67 may be disposed in the waistband region 63 between the waist end edge 16 and the adjacent end of the absorbent core, as shown in FIG. 1 and in FIG. 2. When such an elastic waistband is disposed adjacent to an opening formed by the separation of the topsheet and the backsheet along a waist end edge, the waistband may serve to make the opening elastically openable and self-closing. For example, such an elastic waistband, formed as either a separate element affixed to the backsheet or as an extension of the backsheet in the waistband region, may exert a contractive force tending to draw the waist end edge of the backsheet at the periphery toward the topsheet, thus tending to close the openable end of the openable chassis pocket when it is released.

As another example, an elastic waistband, formed as either a separate element affixed to the topsheet or as an extension of the topsheet in the waistband region, may exert a contractive force tending to hold the waist end edge of the topsheet against the body of the wearer at all times, including when the waist end edge of the backsheet is pulled away from the topsheet to form the opening and thereby gain access into the openable chassis pocket. In addition, as described above in the chassis description, a flexible substrate forming the chassis, such as the backsheet and the topsheet, may be elasticized or otherwise extensible. Thus, the superposed or layered portions of both the topsheet and the backsheet in the openable area along the waist end edge may be elastically contractible, either by means of a waistband or otherwise. In such an embodiment, when the backsheet is pulled away for access into the openable chassis pocket, the waist end edge of the topsheet may be held elastically against the body of the wearer, thereby facilitating the access, and the opening may also be self-closing by means of the elastic contraction of the waist end edge of the backsheet when it is released.

Figure 19:
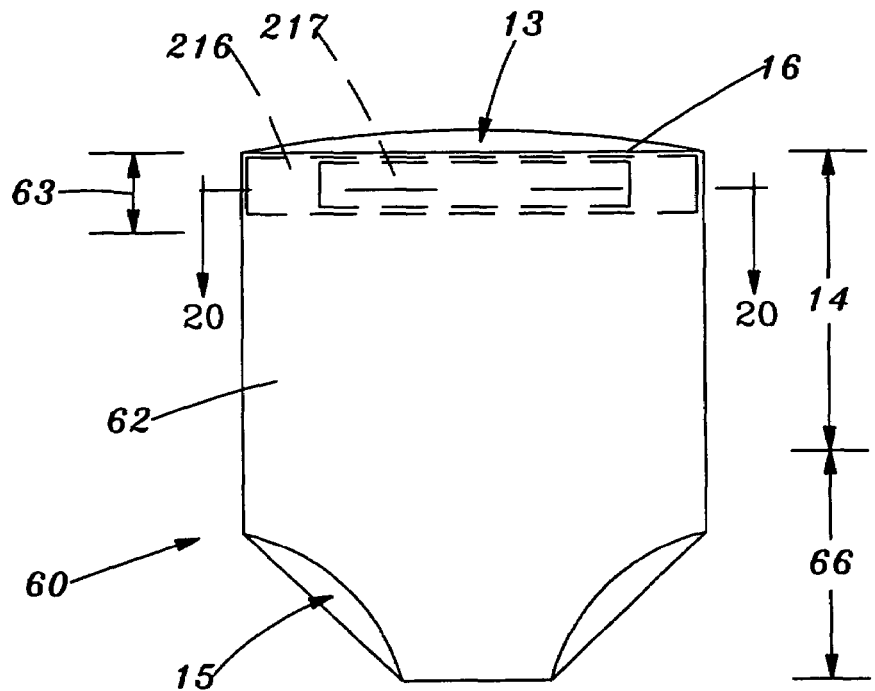
FIG. 19 is a back view of a diaper embodiment having two layered waistbands.
Figure 20:
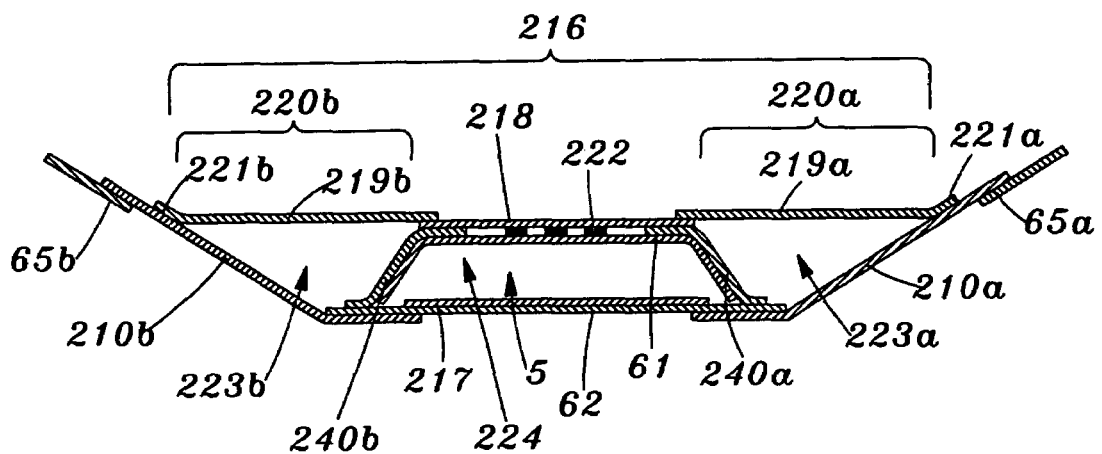
FIG. 20 is a section view of the embodiment of FIG. 19.

In some exemplary embodiments, two elastically extensible waistbands may be disposed in a layered configuration in a waist region of the chassis and may be separable for access into the openable chassis pocket formed between the topsheet and the backsheet, as shown in FIG. 19 and in FIG. 20. In such an embodiment, a first extensible waistband 216 may be disposed on the wearer-facing surface of, and attached to, the wearer-facing layer of the chassis formed by, for example, the topsheet 61, the side panels 210, and/or the barrier leg cuffs 240, when these elements are present. A second extensible waistband 217 may be attached to the garment-facing layer of the chassis formed by, for example, the backsheet 62. The first extensible waistband may have an extensible portion 218 and a non-extensible portion 219 and may also have a free portion 220 that is not attached to the wearer-facing layer of the chassis, i.e., that is free to move independently of the wearer-facing layer of the chassis. The extensible portion 218 may be attached to the wearer-facing layer of the chassis by intermittent bonds 222, such as those described in the Kievit et al. '595 patent. The first extensible waistband may have two laterally opposing ends 221 joined to the chassis. For a closed configuration, such as the pull-on style pant shown in FIG. 18, the opposing ends 221 are preferably joined to the chassis at or near the laterally opposed side seams 8. For an open configuration, such as the taped diaper shown in FIG. 17 or another chassis having laterally opposed side fasteners, the opposing ends 221 may be attached to the wearer-facing layer at or near the laterally opposed side fasteners, such as tape tab fasteners 65.

In such an embodiment, as can be seen in FIG. 20, this layered dual extensible waistband structure forms three openings when the second extensible waistband and the garment-facing layer of the chassis are separated from the first extensible waistband and the wearer-facing layer of the chassis for access into the openable chassis pocket. Each of two laterally opposed substantially triangular openings 223 is formed by the non-extensible portion 219 of the first extensible waistband 216, the adjacent side panel 210, and the adjacent connecting leg of the triangle formed by the topsheet 61 and/or the barrier leg cuff 240. Between these triangular openings 223, a quadrangular opening 224 is formed by the topsheet 61, the second extensible waistband 217 and the adjacent portion of the backsheet 62 on which it is disposed, and the laterally opposed connecting legs of the trapezoid formed by the topsheet 61 and/or the laterally opposed barrier leg cuffs 240. The centrally located quadrangular opening 224 forms the openable end 41 of the openable chassis pocket 5, which is formed and bounded by the same four elements as the quadrangular opening. In particular embodiments, such as that shown in FIG. 20, the quadrangular opening may have a trapezoidal shape, while in other embodiments, it may have a substantially rectangular shape.

By forming these three openings when separated, this layered dual extensible waistband structure provides several advantages. For example, this waistband structure allows the first extensible waistband and the wearer-facing layer of the chassis to remain in contact with the body of the wearer at all times, including when the second extensible waistband and the garment-facing layer of the chassis are separated from the first extensible waistband and the wearer-facing layer of the chassis for access into the openable chassis pocket. By remaining in contact with the body of the wearer, the first extensible waistband and the wearer-facing layer of the chassis can continue to perform their intended function of helping to support the absorbent article and prevent its slippage downward on the torso of a standing wearer, even during the removal and replacement of the replaceable core component. Also, the centrally located quadrangular opening provides a readily visible "target" for the insertion of a replacement core component, as well as a structurally bounded channel allowing the insertion of the replacement core component only when it is substantially properly laterally aligned with respect to the chassis.

Figure 21:
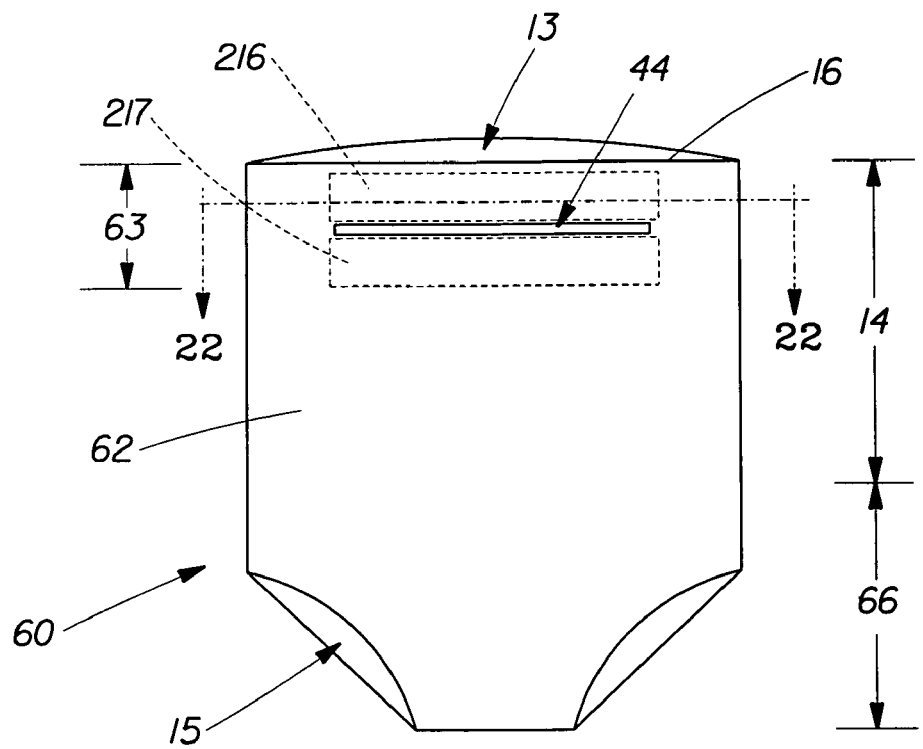
FIG. 21 is a back view of a diaper embodiment having two side-by-side waistbands.
Figure 22:
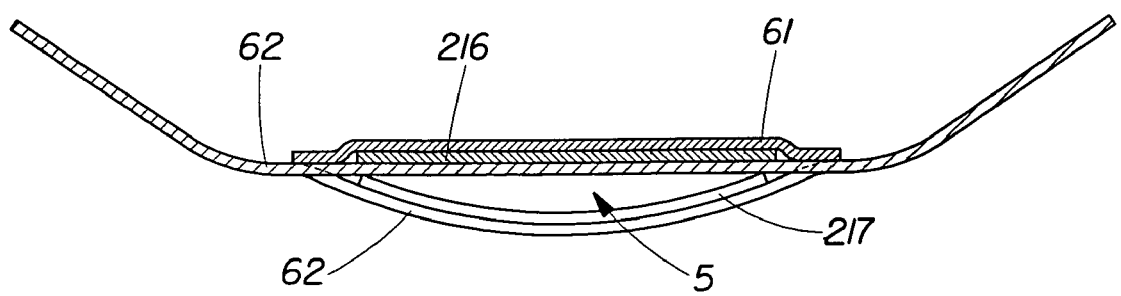
FIG. 22 is a section view of the embodiment of FIG. 21.

In an alternative embodiment, as shown in FIG. 21 and FIG. 22, a first extensible waistband 216 may be sandwiched between and attached to the wearer-facing layer and the garment-facing layer and a second extensible waistband 217 attached to or forming an extension of only the garment-facing layer may be disposed adjacent to the first extensible waistband in a position farther from the adjacent waist end edge 16, i.e., toward the crotch region 66, relative to the first extensible waistband. The garment-facing layer, e.g., the backsheet 62, in such an embodiment may include an aperture 44 between the two extensible waistbands providing access into the openable chassis pocket 5 formed between the wearer-facing layer and the garment-facing layer when the second extensible waistband 217 is separated from the first extensible waistband 216 as shown in FIG. 22. Preferably, at least the second extensible waistband is elastically extensible.

In some embodiments, the portion of the garment-facing layer surrounding the second extensible waistband may also be extensible.

Figure 23:
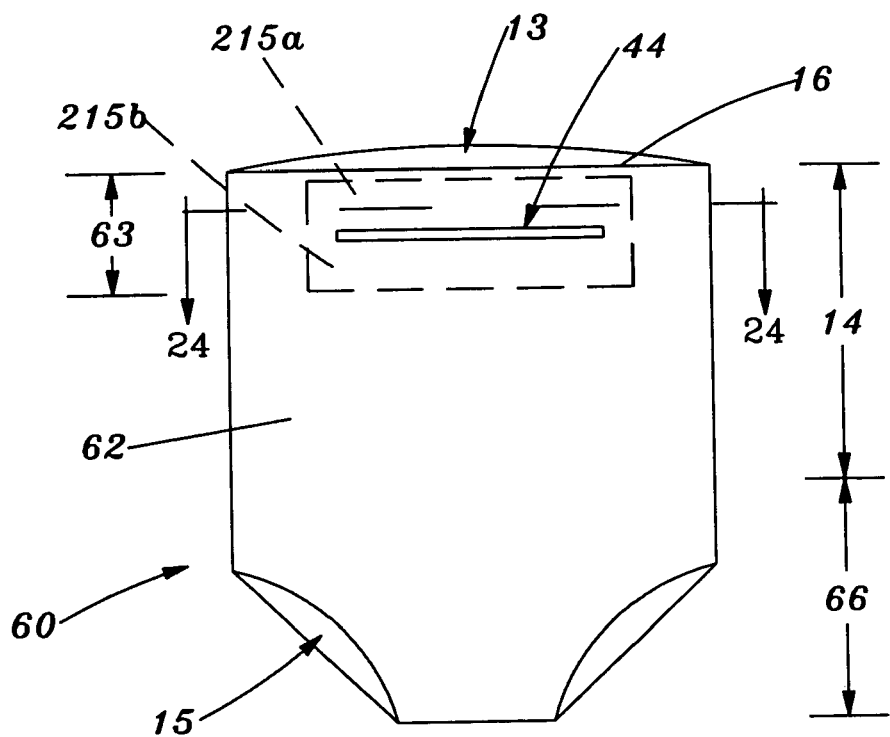
FIG. 23 is a back view of a diaper embodiment having an apertured waistband.
Figure 24:
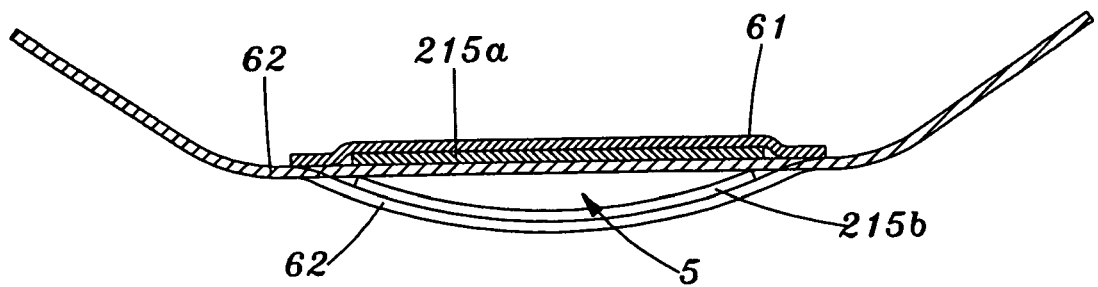
FIG. 24 is a section view of the embodiment of FIG. 23.

In an alternative embodiment shown in FIG. 23 and FIG. 24, an extensible waistband 215 may include a first portion 215a sandwiched between and attached to the wearer-facing layer and the garment-facing layer in a portion of the waistband region adjacent to the waist end edge 16 and a second portion 215b attached to only the garment-facing layer and disposed farther from the adjacent waist end edge, i.e., toward the crotch region 66, relative to the first portion of the extensible waistband. The extensible waistband and the garment-facing layer, e.g., the backsheet 62, in such an embodiment may each include an aperture 44 between the two portions of the extensible waistband providing access into the openable chassis pocket 5 formed between the wearer-facing layer and the garment-facing layer when the second portion 215b is separated from the first portion 215a as shown in FIG. 24. Preferably, the extensible waistband is elastically extensible. In some embodiments, the portion of the garment-facing layer surrounding the extensible waistband may also be extensible.

Figure 25:
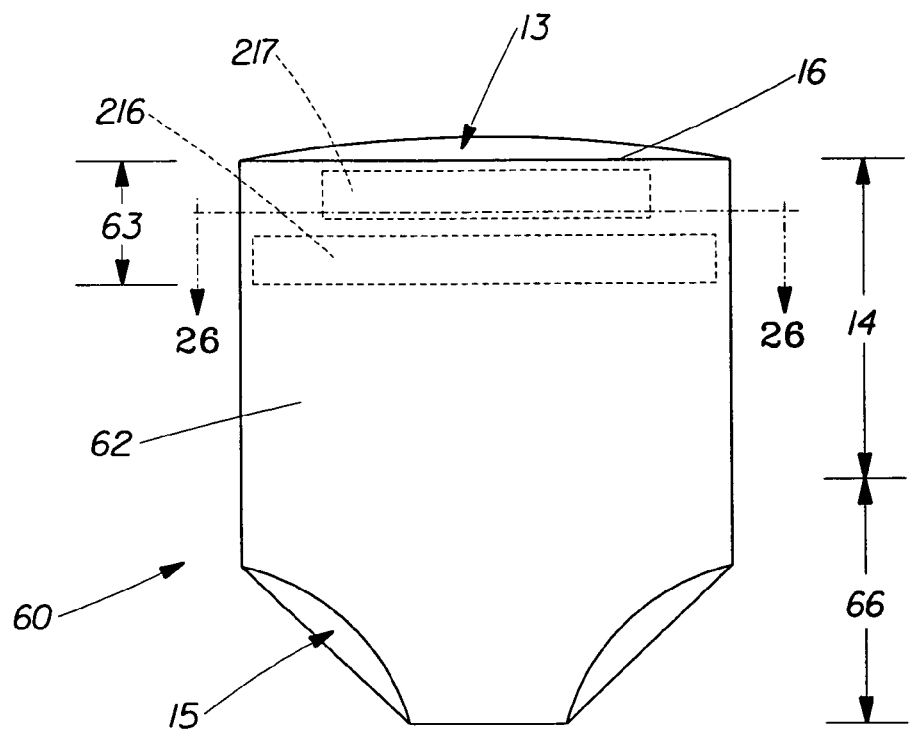
FIG. 25 is a back view of a diaper embodiment having two side-by-side waistbands in different layers.
Figure 26:
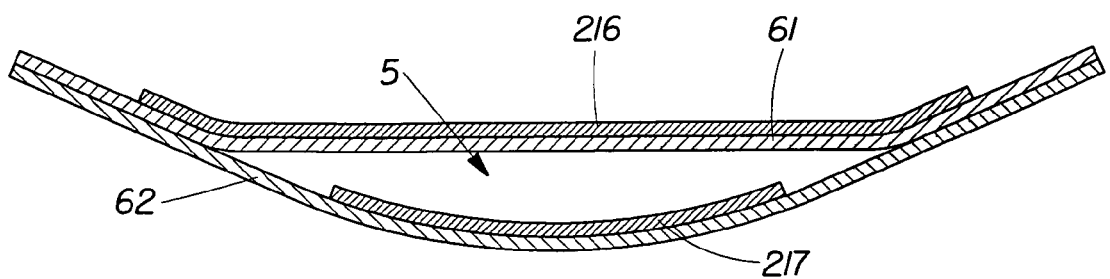
FIG. 26 is a section view of the embodiment of FIG. 25.

In another alternative embodiment shown in FIG. 25 and FIG. 26, a first extensible waistband 216 may be attached to the wearer-facing layer and a second extensible waistband 217 attached to or forming an extension of the garment-facing layer may be disposed adjacent to the first extensible waistband in a position closer to the adjacent waist end edge 16, i.e., farther from the crotch region 66, relative to the first extensible waistband. The wearer-facing layer and the garment-facing layer may be separable in the waistband region 63, providing access into the openable chassis pocket 5 formed between the wearer-facing layer and the garment-facing layer when the second extensible waistband and the garment-facing layer of the chassis are separated from the first extensible waistband and the wearer-facing layer of the chassis. Preferably, at least the second extensible waistband is elastically extensible. In some embodiments, the portion of the garment-facing layer surrounding the second extensible waistband may also be extensible.

Figure 27:
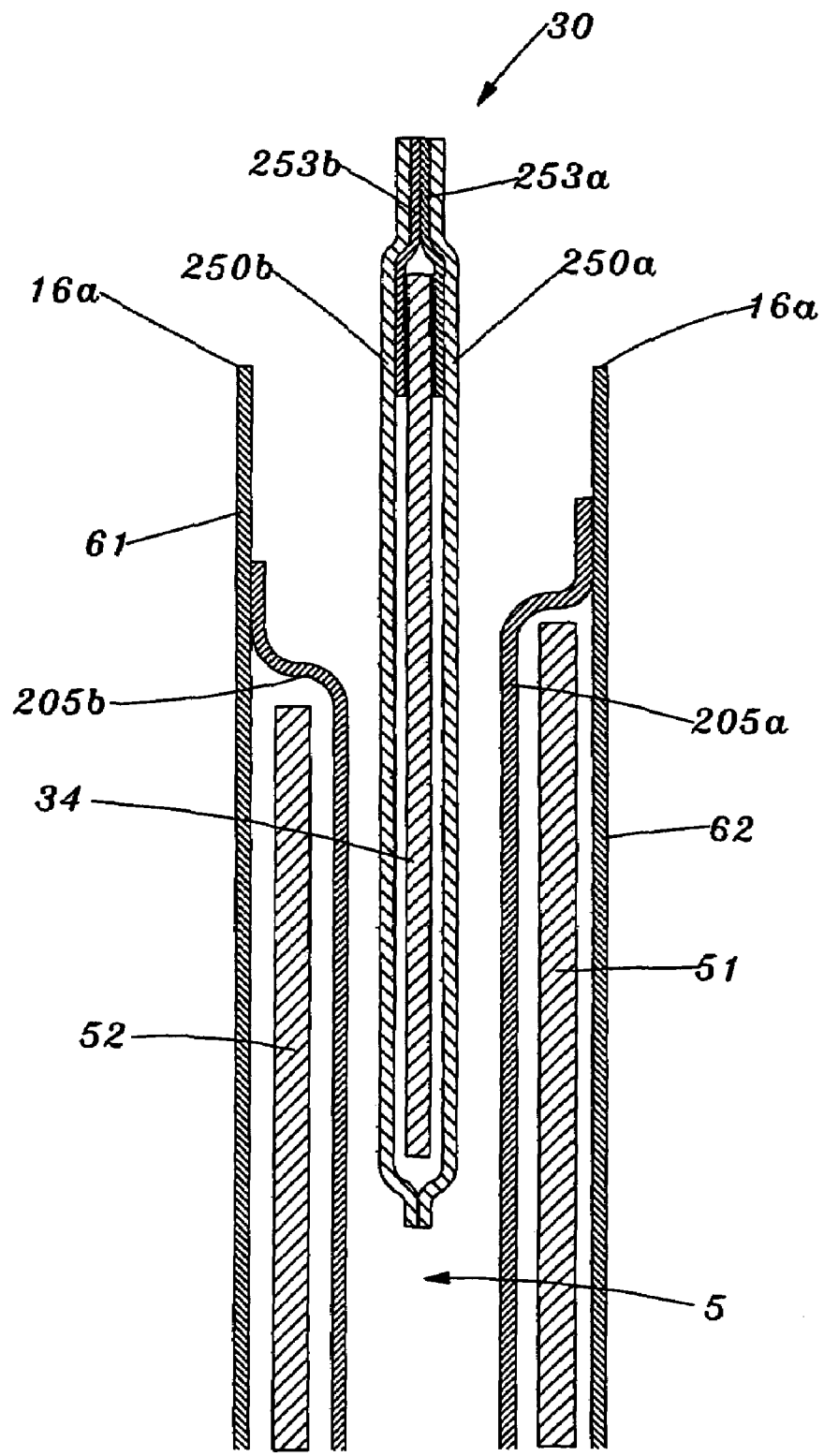
FIG. 27 is a partial section view showing chassis layers and non-removable absorbent core layers in relation to a replaceable absorbent core component.

As shown in FIG. 27, a portion of the non-removable core component, such as the uppermost absorbent layer 52 of the center section, may be disposed between a liquid pervious wearer-facing layer of the chassis, such as the topsheet 61, and another liquid pervious layer 205 of the chassis. One or both of the liquid pervious layers may form a portion of the openable chassis pocket 5 adapted to receive the replaceable absorbent core component, e.g., back panel 30. Preferably, an acquisition member, a distribution member, or an acquisition/distribution member of the non-removable core component is disposed between the liquid pervious layers. In some embodiments, at least one of the liquid pervious layers may be disposed between two members of the non-removable core component.

Alternatively, a portion of the non-removable core component, such as the lowermost absorbent layer 51 of the center section shown in FIG. 27, may be disposed between a liquid pervious layer 205 of the chassis and a liquid impervious layer of the chassis, such as the backsheet 62. One or both of the liquid pervious layer and the liquid impervious layer may form a portion of the openable chassis pocket 5 adapted to receive the replaceable absorbent core component, e.g., back panel 30. Preferably, a distribution or acquisition/distribution member of the non-removable core component is disposed between the liquid pervious and the liquid impervious layers.

In some embodiments, the liquid pervious layer may be disposed between two members of the non-removable core component.

In order to provide additional space within the openable chassis pocket, the surfaces forming the openable chassis pocket, e.g., the topsheet, the backsheet, the barrier leg cuffs, etc., may be formed from extensible materials, preferably elastically extensible materials, to permit the expansion of the pocket. These materials are preferably extensible in at least in the lateral direction and preferably in both the lateral and longitudinal directions. This expansibility of the openable chassis pocket may facilitate the removal and/or the insertion of a replaceable core component and may also be useful in embodiments in which the replaceable core component includes an absorbent layer that expands as it absorbs liquid.

In some exemplary embodiments, the openable chassis pocket and the replaceable core component may be "keyed" to each other, so as to prevent the insertion of the replaceable core component in any orientation other than a predetermined orientation contemplated in the design of the replaceable core component. Thus, the openable chassis pocket may be shaped and the replaceable core component may be correspondingly shaped to fit within the shaped openable chassis pocket.

Figure 28:
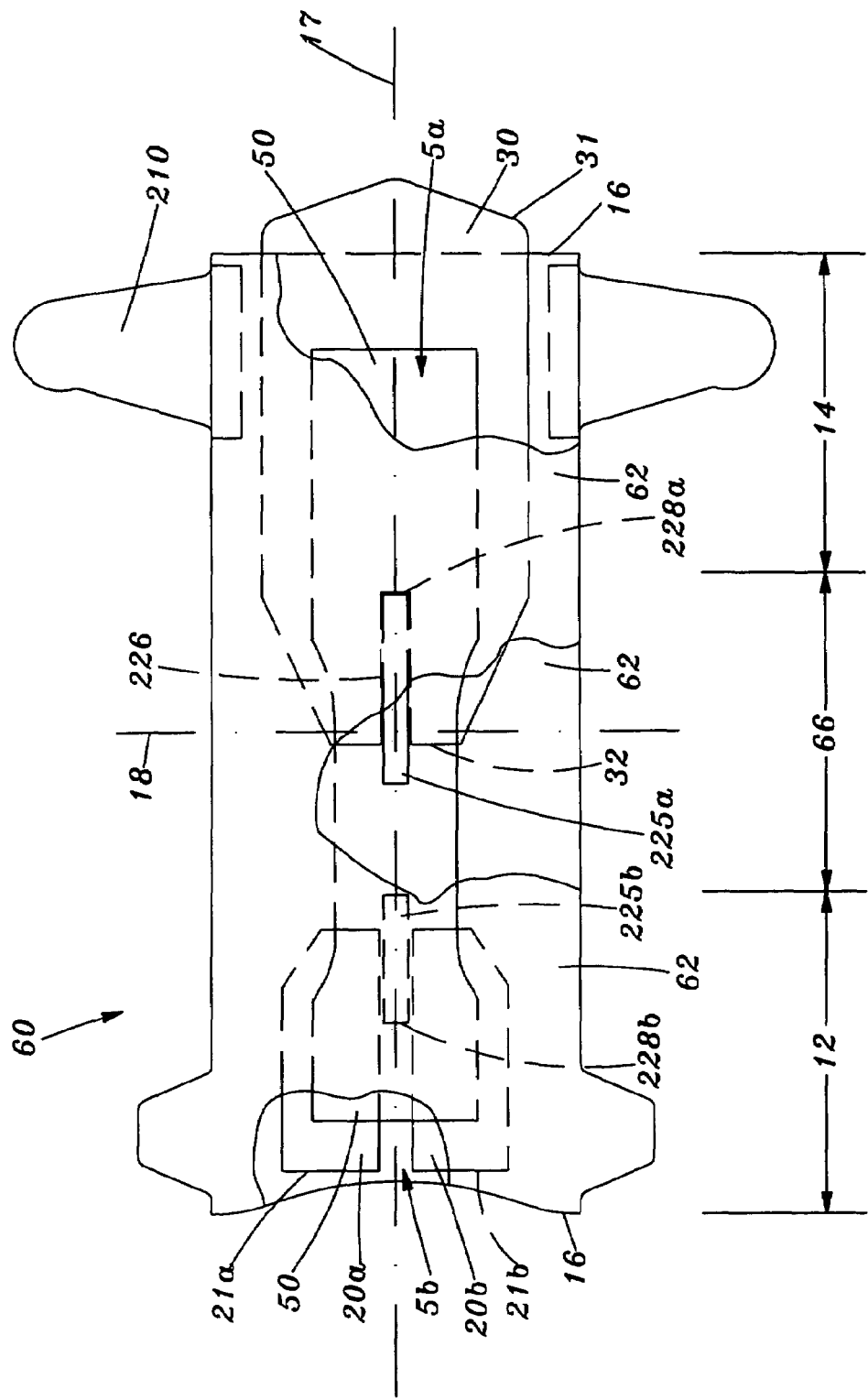
FIG. 28 is a plan view of another exemplary diaper of the present invention in its flat-out, uncontracted state, i.e., with all elastic induced contraction pulled out, with portions of the structure being cut away to more clearly show the construction of the diaper, and with the portion of the diaper that contacts the wearer facing the viewer, showing a chassis pocket having a separator.

For example, in some embodiments as shown in FIG. 28, the openable chassis pocket 5 may include a separator 225 that bifurcates or partitions the pocket into at least two connected branches forming the shaped openable chassis pocket. The separator may be formed by an area of joining of the topsheet and the backsheet or by an area of joining of the topsheet or the backsheet, or both, to the non-removable core component, thereby bifurcating or partitioning the openable chassis pocket. In embodiments having such a bifurcated openable chassis pocket, the replaceable core component, e.g., back panel 30, may include a cooperative structure 226 that permits the insertion of its inner end 32 beyond the outer end 228 of the separator, i.e., to a point farther from the waist end edge than the outer end of the separator. Such a cooperative structure may include a slit, a slot, or a groove formed in the replaceable core component for receiving and/or bypassing the separator. The separator in the openable chassis pocket may be formed along the longitudinal centerline 17 of the chassis and the cooperative structure in the replaceable core component may be formed along the longitudinal centerline 25 of the replaceable core component or, alternatively, either the separator or the cooperative structure, or both, may be offset from the respective longitudinal centerline. Either the symmetric or the offset configuration may serve to ensure that the replaceable core component is inserted in the intended end-to-end orientation, i.e., with its inner end in the crotch region and its outer end in the waist region. Either configuration may also serve to ensure that the replaceable core component is inserted in a predetermined lateral position, is inserted with its liquid pervious surface region in a predetermined longitudinal and/or lateral position, and so on. In addition, an offset configuration may be especially useful because, in order to fit into the asymmetrically bifurcated openable chassis pocket, the replaceable core component must be inserted in both the intended end-to-end orientation and the intended orientation of its predetermined wearer-facing and garment-facing surfaces.

It is noted that more than one shaping element, such as more than one separator, as well as shaping elements other than a separator, are envisioned. Exemplary shaping elements may include a slot into which a corresponding "key" fits in only a predetermined orientation, one or more holes or depressions into which one or more corresponding pins, bosses, or protuberances fits in only a predetermined orientation, a partition within the openable chassis pocket that requires the replaceable core component to be partially inserted and then rotated and/or translated in order for the insertion to be completed, and similar configurations.

In embodiments in which the openable chassis pocket is divided into several separate connected branches or into non-interconnected sections, i.e., divided effectively into separate openable chassis pockets, a corresponding number of replaceable core components may be placed into the sections of the openable chassis pocket in a side-by-side lateral relationship. For example, in some embodiments as shown in FIG. 28, a pair of front panels 20 may be inserted into a bifurcated openable chassis pocket.

Figure 29:
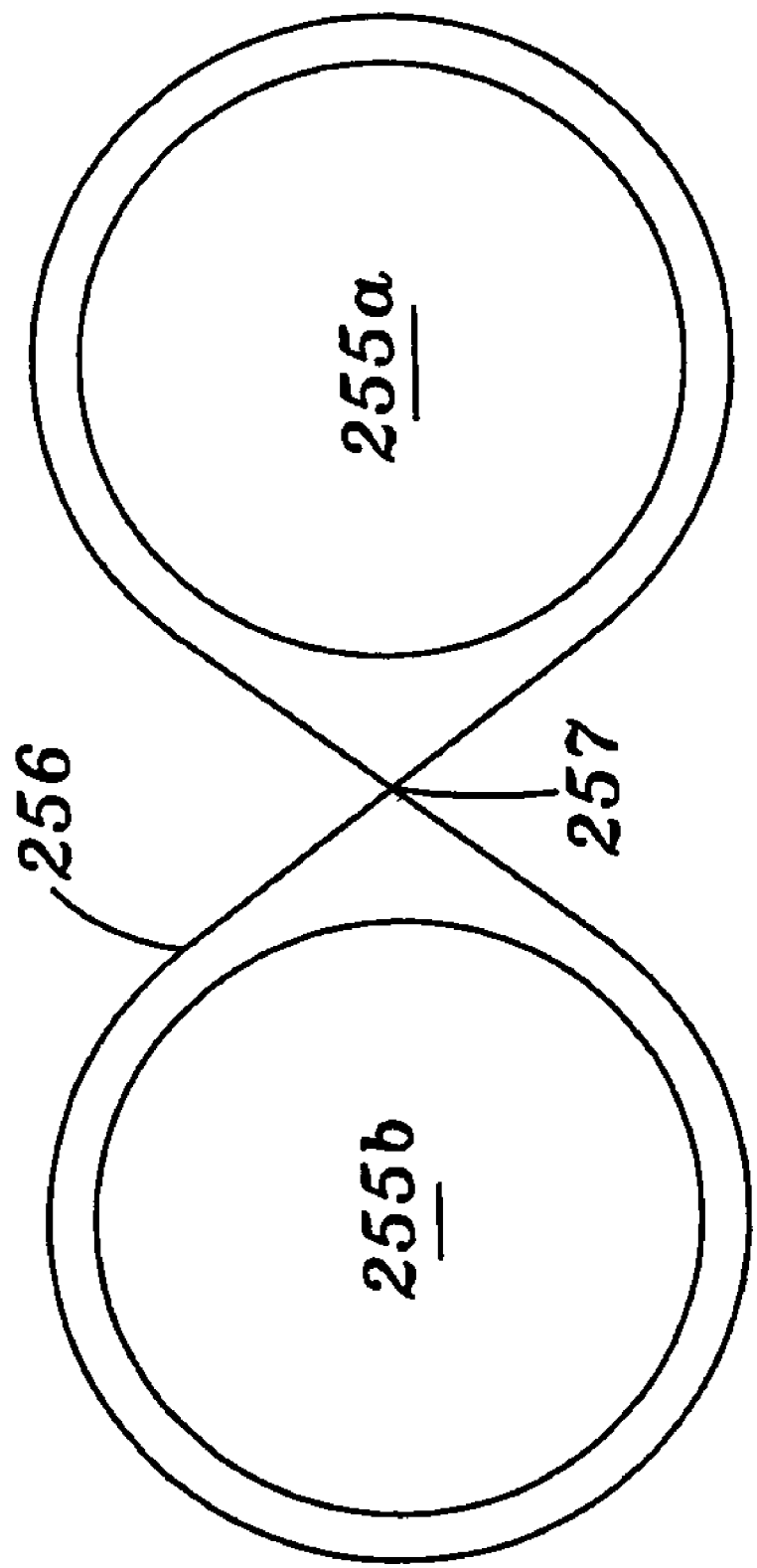
FIG. 29 is simplified plan view illustrating the method of determining the crotch point of an absorbent article.

In some embodiments, the openable chassis pocket may extend from a waist region into the crotch region as far as the crotch point. In particular, it is preferred that the openable chassis pocket extend from the respective waist region into the crotch region no farther than the crotch point of the absorbent article, so as to thereby limit the depth of insertion of a replaceable core component to no farther than the crotch point. The "crotch point" of an absorbent article and of the absorbent article's absorbent core is determined by placing the article on a wearer of the physical size for which the absorbent article is designed and who is in a fully upright standing position with his or her feet a shoulder width apart and then placing an extensible filament 256 around the legs 255 in a figure eight configuration as shown in FIG. 29. The point in the absorbent article and the absorbent core corresponding to the point of intersection 257 of the filament is considered to be the crotch point of the absorbent article and of the absorbent core. It is understood that the crotch point is determined by placing an absorbent article in the intended manner on a standing wearer of the correct size for the article and determining where the crossed filament would contact the absorbent article and/or the absorbent core.

The Replaceable Absorbent Core Component

Figure 30:
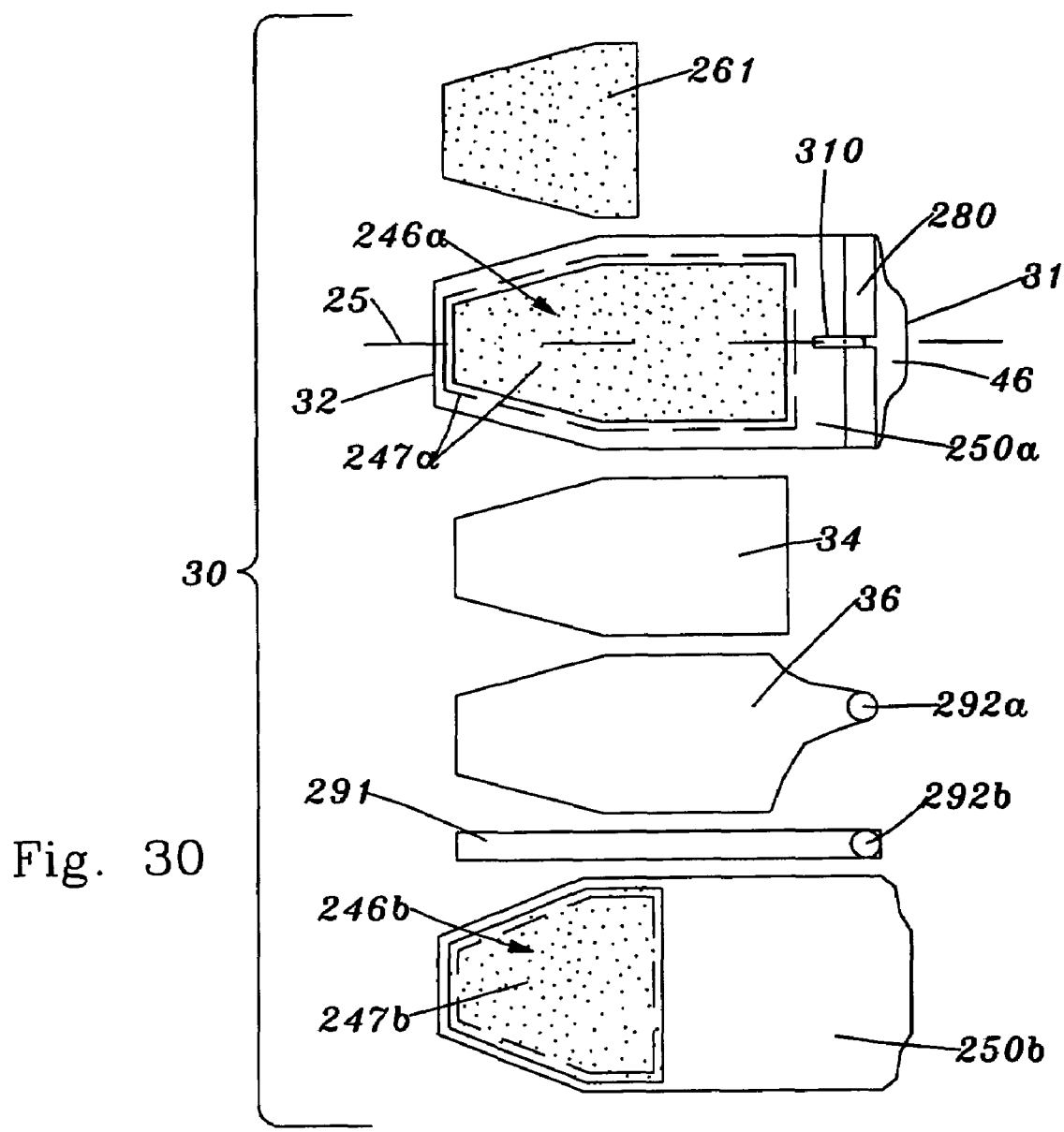
FIG. 30 is an exploded view of the layers of a replaceable absorbent core component.
Figure 31:
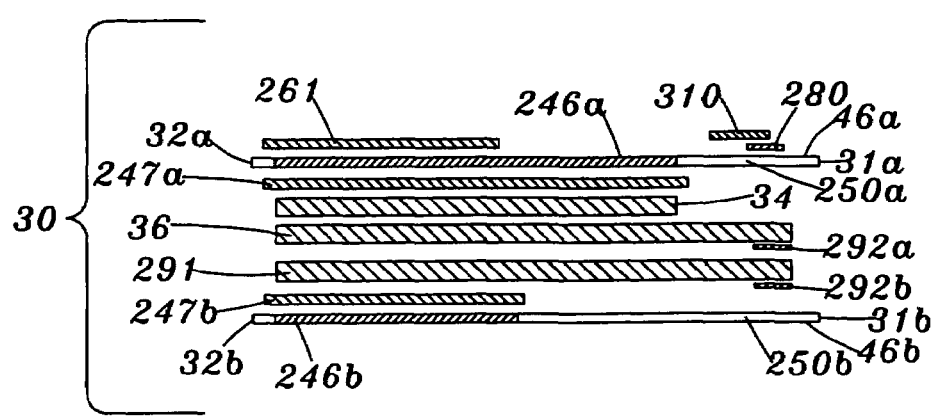
FIG. 31 is a view of the layers of FIG. 30 in a stacked arrangement.

In order for the absorbent layer of the replaceable core component to be in capillary liquid communication with the non-removable core component, at least a portion of one major surface of the replaceable core component must be pervious to liquid. This pervious portion of the major surface may be described as forming a permeable liquid transfer region 246. In exemplary embodiments, at least about 20% of the area of this major surface is liquid pervious. Preferably, at least about 50%, and more preferably, at least about 80%, of this major surface may be liquid pervious. The permeable liquid transfer region may be covered by a liquid pervious sheet 247. Also, the replaceable core component may have permeable liquid transfer regions in both of its major surfaces. For example, in the exemplary embodiment shown in FIG. 30 and FIG. 31, the back panel 30 has the permeable liquid transfer region 246a in its upper major surface formed by the upper packet layer 250a and the permeable liquid transfer region 246b in its lower major surface formed by the lower packet layer 250b.

Except for the permeable liquid transfer region or regions, the major surfaces of the replaceable core component may be liquid impervious. In particular, it may be desirable for the outer end segment or at least the area of the pull tab at the outer end to be liquid impervious in order to prevent the escape or the leakage of liquid from this portion of the replaceable core component. The prevention of leakage from this area may enable a caregiver to avoid contact during the removal of a used replaceable core component with the liquid contained in it. A liquid impervious region may be formed by a liquid impervious layer disposed between the absorbent layer of the replaceable core component and the layer forming the surface, such as by the liquid impervious layer 253 disposed between the absorbent layer 34 of the back panel 30 and the packet layer 250 shown in FIG. 27. Alternatively, the liquid impervious region may be formed by a liquid impervious layer forming the major surface or by the treatment of an otherwise liquid pervious layer to render it liquid impervious in the desired region. For example, in the embodiment shown in FIG. 31, the portions of the packet layers 250 between the permeable liquid transfer regions 246 and the outer end 31 of the back panel 30 may either include a liquid impervious sheet material or be treated to become liquid impervious.

Figure 32:
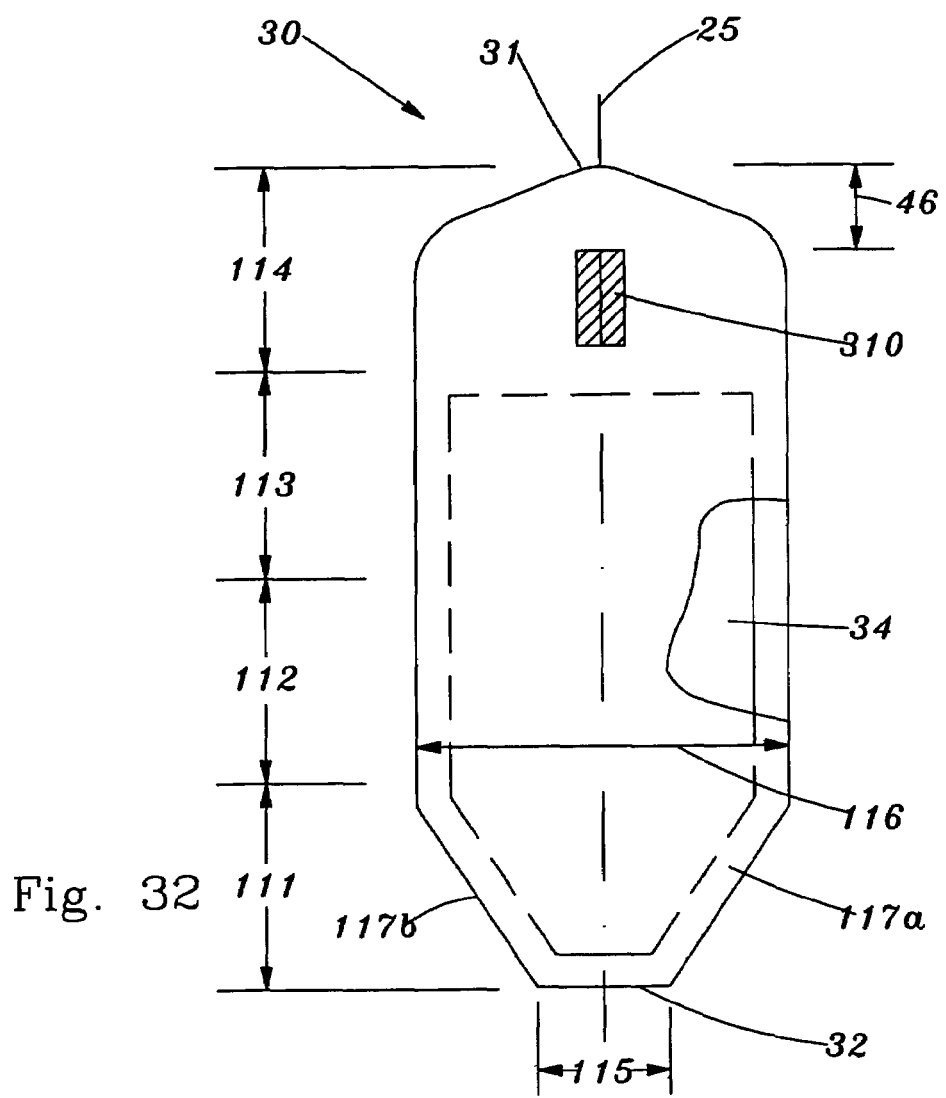
FIG. 32 is a plan view showing a replaceable absorbent core component illustratively divided into four longitudinal segments.

The replaceable core component, e.g., the back panel 30 shown in FIG. 32, has an inner end 32 and an outer end 31 and may be divided longitudinally for descriptive purposes into successive first, second, third, and fourth segments defined by respective quarters of its length. The replaceable core component may have two major surfaces having substantially equal areas and, for descriptive purposes, the area of each of the four longitudinal segments may be expressed as the area of the portion of one of the major surfaces falling within the segment. When so divided, the first segment 111, which is also referred to herein as the inner end segment, includes the inner end and may have an area less than an area of any one of the second, third, and fourth segments. For example, the inner end of the replaceable core component may have a smaller width 115 than the width 116 of the second segment 112 and may have converging sides 117, i.e., the inner end segment may convergingly taper toward the inner end. The fourth segment 114, which is also referred to herein as the outer end segment, includes the outer end and may have an area less than the area of at least one of the second segment or the third segment 113. The areas of the second and third segments may be substantially equal or the second segment may have an area less than that of the third segment. In some embodiments, the four segments may have the following areas. The first segment may have an area of between 10 cm$^2$ and 110 cm$^2$ or, preferably, between 30 cm$^2$ and 70 cm$^2$. The second segment may have an area of between 10 cm$^2$ and 110 cm$^2$ or, preferably, between 30 cm$^2$ and 100 cm$^2$. The fourth segment may have an area of between 10 cm$^2$ and 110 cm$^2$ or, preferably, between 30 cm$^2$ and 100 cm$^2$. The third segment may have an area of between 10 cm$^2$ and 110 cm$^2$ or, preferably, between 30 cm$^2$ and 100 cm$^2$. Based on these areas, the overall surface area of the replaceable core component may be between 40 cm$^2$ and 440 cm$^2$ or, preferably, between 120 cm$^2$ and 370 cm$^2$.

Figure 33:
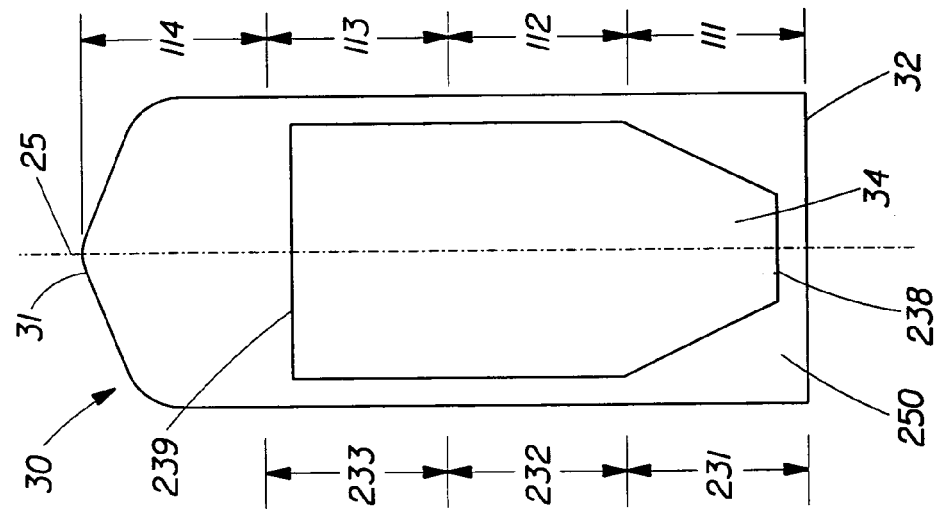
FIG. 33 is a plan view showing an absorbent layer of a replaceable absorbent core component illustratively divided into four longitudinal segments.
Figure 34:
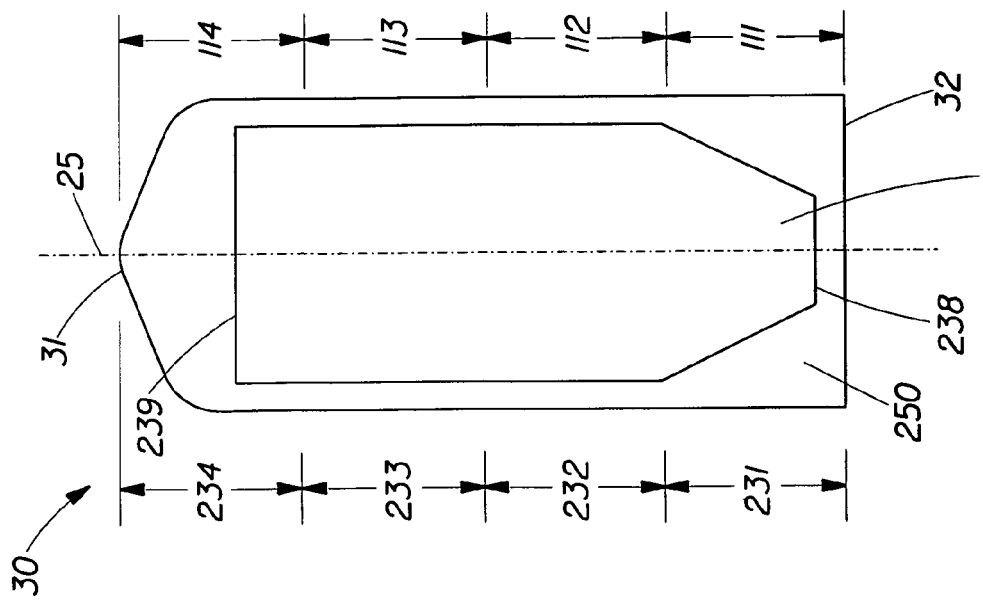
FIG. 34 is a plan view showing another absorbent layer of a replaceable absorbent core component illustratively divided into four longitudinal segments.

Similarly, the absorbent structure of the replaceable core component, e.g., an absorbent layer 34 of back panel 30, has an inner end 238 and an outer end 239 and may be divided longitudinally for descriptive purposes into four successive segments 231, 232, 233, and 234 from its inner end to its outer end, corresponding to the four segments of the replaceable core component as a whole. Like the replaceable core component, the absorbent structure may have two major surfaces having substantially equal areas and, for descriptive purposes, the area of each of the four longitudinal segments of the absorbent structure may be expressed as the area of the portion of one of the major surfaces falling within the segment. In some embodiments, an absorbent layer may extend from the first segment 111 of the replaceable core component to the fourth segment 114 of the replaceable core component, as shown in FIG. 33. In other embodiments, the absorbent layer may extend only from the first segment 111 to the second segment 112 or to the third segment 113 of the replaceable core component, as shown in FIG. 34. The first absorbent layer segment 231, or inner end segment of the absorbent layer, includes the inner end of the absorbent layer and may have an area less than an area of any one of the other segments of the absorbent layer. For example, the inner end of the absorbent layer may have a width smaller than a maximum width of the second segment of the absorbent layer and may have converging sides, i.e., the inner end segment may convergingly taper toward the inner end. The absorbent layer may have an overall shape similar to the shape of the replaceable core component, as a whole. For example, the absorbent layer may have a shape identical to that of the replaceable core component, but reduced in scale, so as to fit at some distance inside the perimeter of the replaceable core component. Alternatively, the absorbent layer and overall replaceable core component may have different shapes. For example, the overall replaceable core component may have a substantially rectangular shape, while the absorbent layer inside it may have a tapered shape.

Figure 36:
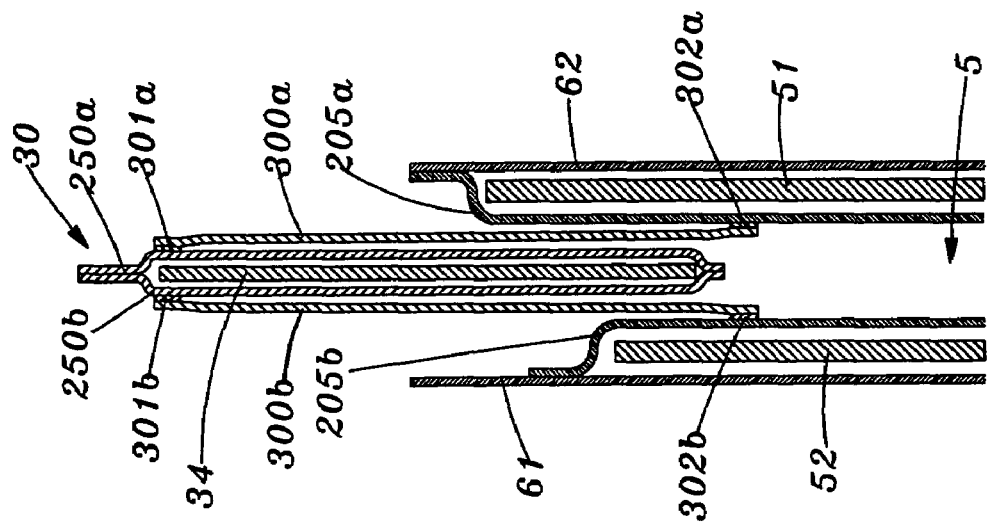
FIG. 36 is a partial section view showing the extensible covering layer of FIG. 35 in an extended state.
Figure 35:
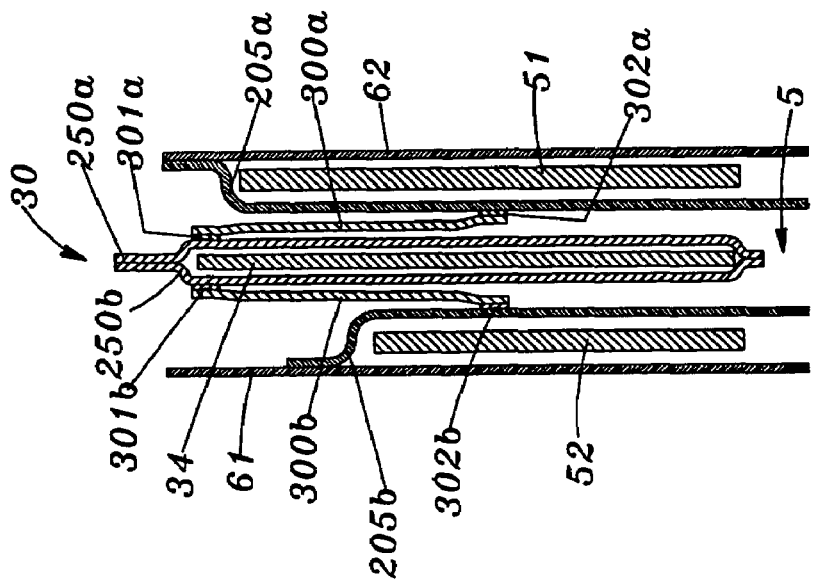
FIG. 35 is a partial section view showing an extensible covering layer in an unextended state.

As shown in FIG. 35 and FIG. 36, the replaceable core component may include an extensible covering layer 300 attached to one end segment of the replaceable core component. The extensible covering layer is preferably permanently attached to the replaceable core component in the outer end segment of the replaceable core component, such as by permanent attachment means 301, and is preferably sufficiently extensible to cover the used replaceable core component for disposal. Such an extensible covering layer may be releasably attached to the chassis when the replaceable core component is in the absorbent article, as shown in FIG. 35. During the removal of the replaceable core component from the absorbent article in the direction indicated by the arrow 321, a portion of the extensible covering layer is temporarily held by the releasable attachment means 302 and the extensible covering layer is thereby extended to cover the replaceable core component as it is withdrawn, as shown in FIG. 36. Once the replaceable core component is fully withdrawn from the chassis, the releasable attachment means may release the extensible covering layer from the chassis and the extensible covering layer may then continue to cover the replaceable core component. In some embodiments, the extensible covering layer may be joined to an insertion tool in a first area of joining so as to be peelably releasable and may be non-releasably joined to the replaceable core component in a second area of joining. In such an embodiment, the extensible covering layer may be released from the insertion tool and releasably attached to the chassis adjacent to the outer end of the replaceable core component as the insertion tool is withdrawn from the chassis. When the replaceable core component is subsequently removed from the chassis, the extensible covering layer may remain attached to the chassis, so as to extend to cover the outer surface of the replaceable core component, and then may be released from the chassis.

The extensible covering layer 300 may be constructed in a number of ways. For example, the extensibility may be provided by the use of an extensible, preferably low modulus material, or alternatively by folding or pleating the extensible covering layer so that removal of the replaceable component extends or unfolds the extensible covering layer to cover the replaceable component, as shown in FIG. 37 and FIG. 38. In some embodiments, the extensible covering layer may be plastically extensible or deformable. In exemplary embodiments including an extensible covering layer, the extensible covering layer preferably covers less than 75% of the area of the replaceable core component prior to extension of the extensible covering layer and, more preferably, covers less than 50% of the area. In the embodiments in which the extensible covering layer is unfolded to provide the extension of the extensible covering layer, the extensible covering layer has at least one fold, preferably at least two folds, and more preferably at least three folds. For embodiments comprising a folded extensible covering layer, the extensible covering layer preferably covers less than 75% of the area of the replaceable core component prior to extension of the extensible covering layer, more preferably less than 50% of the area, and most preferably less than 25% of the area. A combination of folding and extensibility can also be used to form the extensible covering layer. In such an embodiment, the extensible covering layer may first unfold and then extend, preferably through plastic deformation, to cover the remainder of the replaceable core component. The extensible covering layer should extend to cover at least the permeable liquid transfer region of the replaceable core component and, preferably, the extensible covering layer extends beyond the inner end of the replaceable core component as it is withdrawn. In some embodiments, the extensible covering layer may extend beyond the innermost end edge of the replaceable core component and the releasable attachment means may meet to form a partial closure of the openable pocket formed by the extensible covering layer.

The replaceable core component may include a location stabilizer 310, as shown in FIG. 39 and FIG. 40, adapted to releasably retain the replaceable core component in its fully inserted position, such as by releasably attaching the replaceable core component to the chassis in the waist region, in the crotch region, or in both regions. The location stabilizer may include a mechanical surface fastener such as either a hook or a loop member disposed on the replaceable core component and adapted to engage a complementary member disposed on the chassis, or to engage a non-woven surface of the chassis. In some embodiments, the location stabilizer may include an adhesive disposed on the surface of the replaceable core component and adapted to releasably engage a surface of the chassis. Alternatively, the chassis may include a location stabilizer adapted to releasably engage a surface of the replaceable core component. In some embodiments, the location stabilizer may include a tab adapted to be inserted into a slot and thereby releasably retain the replaceable core component in its fully inserted position. For example, a tab on the replaceable core component may be insertable into a slot in the chassis or vice versa. Such a tab disposed at the outer end segment of the replaceable core component may be inserted into a corresponding slot to serve as the location stabilizer 310 while the replaceable core component is fully inserted and then may be removed from the slot and used as the removal pull tab 46 when the replaceable core component is removed from the chassis.

As is also shown in FIG. 39 and FIG. 40, the replaceable core component may include a pull tab 46 that can be used to remove the core component from the chassis. Such a pull tab may include a gripping portion 237 to facilitate control of the replaceable core component during its removal. The gripping portion may include a material with a higher coefficient of friction than the remainder of the surface of the replaceable core component, or may have a textured surface, to facilitate grasping the pull tab for removal. In some embodiments, the pull tab may have various configurations, such as a configuration including a pull ring 236 into which a finger may be inserted to facilitate removal.

Figure 41:
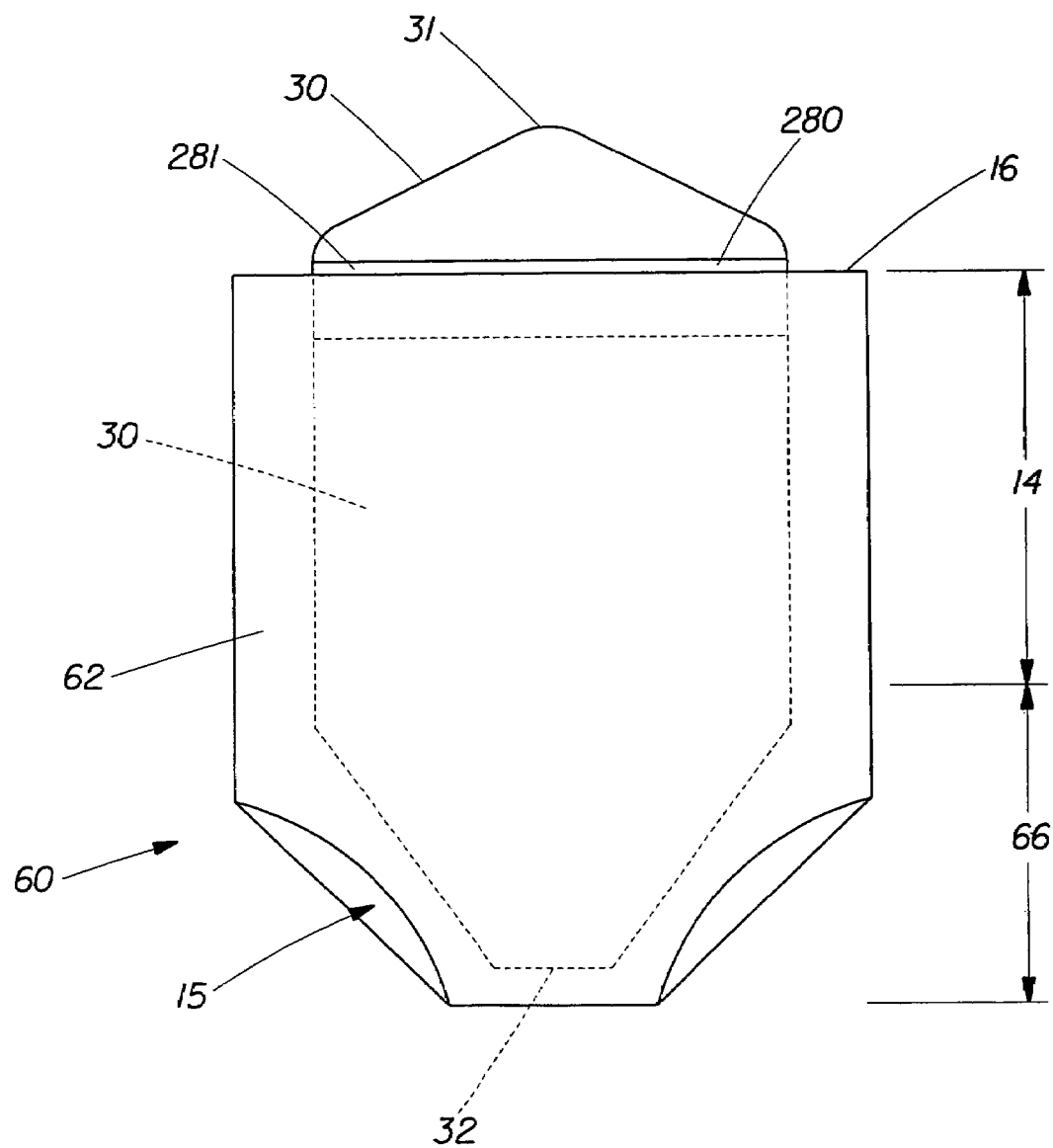
FIG. 41 is a plan view showing a replaceable absorbent core component having an insertion depth indicator.
Figure 43:
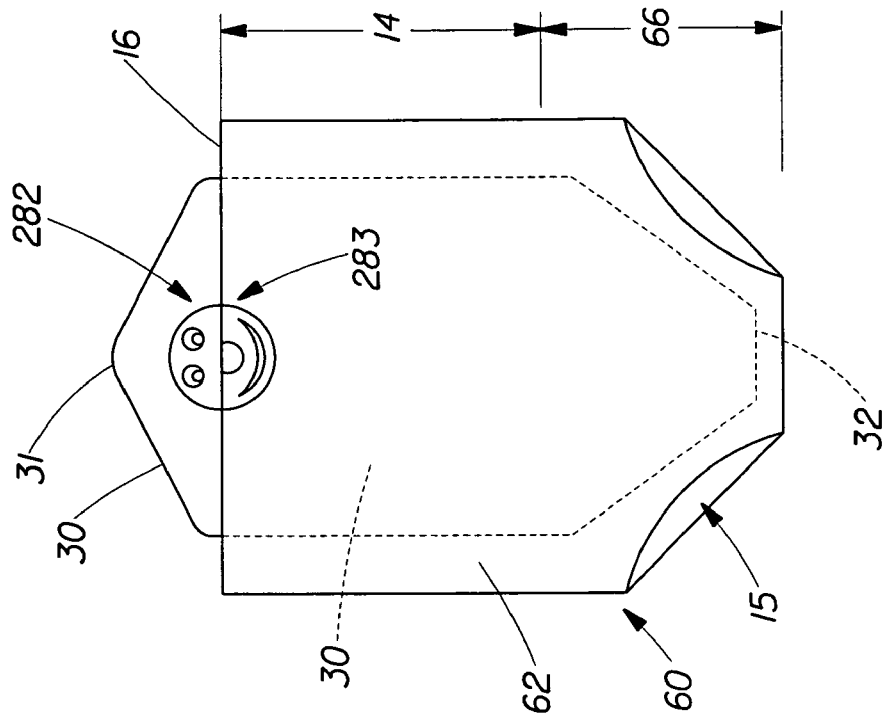
FIG. 43 is a plan view showing the replaceable absorbent core component of FIG. 42 in a fully inserted state.
Figure 42:
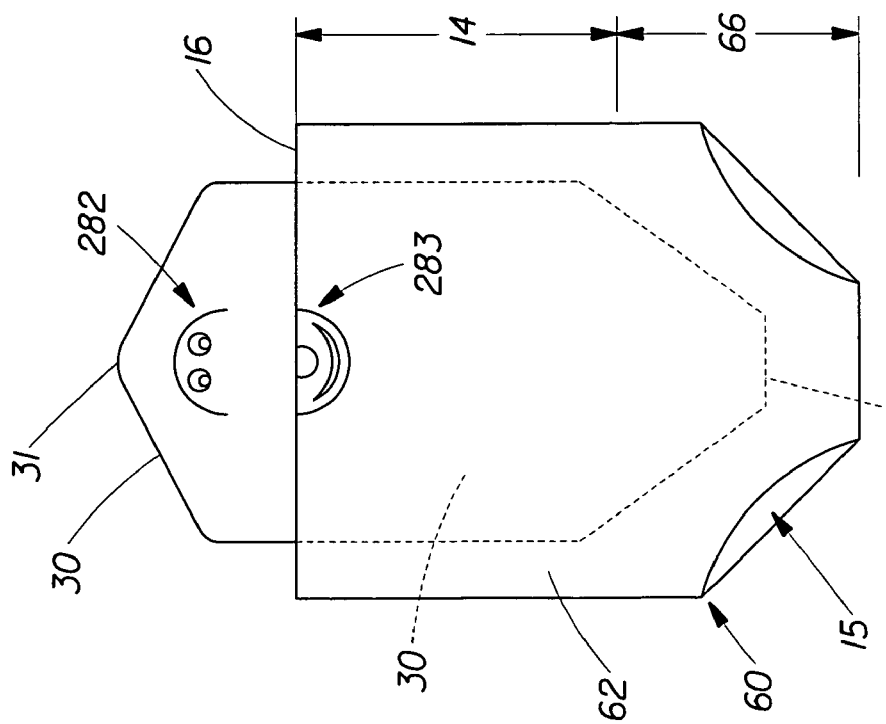
FIG. 42 is a plan view showing a replaceable absorbent core component having a graphical object insertion depth indicator in a partially inserted state.
Figure 45:
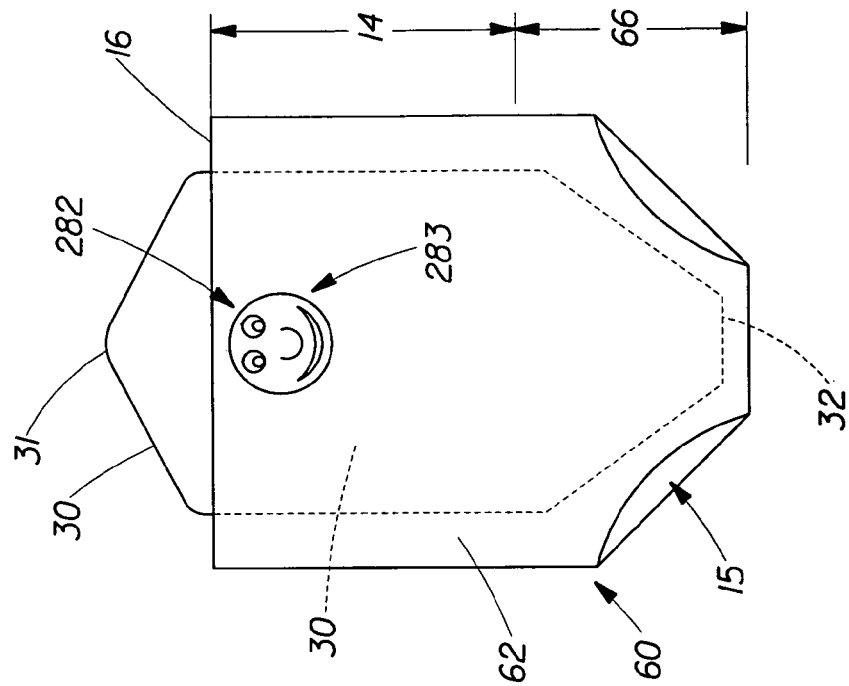
FIG. 45 is a plan view showing the replaceable absorbent core component of FIG. 44 in a fully inserted state.
Figure 44:
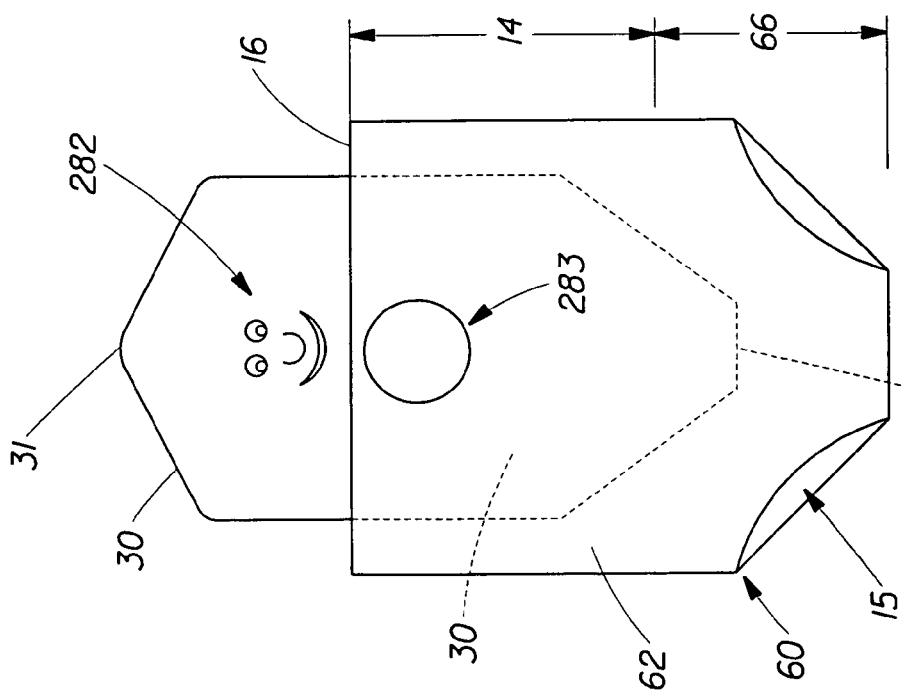
FIG. 44 is a plan view showing a replaceable absorbent core component having another graphical object insertion depth indicator in a partially inserted state.

The replaceable core component may include an insertion depth indicator 280 to provide an indication when a predetermined position of the replaceable core component relative to the chassis is reached. The insertion depth indicator may include a visible indicator such as a line 281 positioned in the outer end segment of the replaceable core component, as shown in FIG. 41, such that the line is aligned with the waist end edge 16 of the chassis when the predetermined position of the replaceable core component is reached. In another example of a visible insertion depth indicator, as shown in FIG. 42 and FIG. 43, a graphical object 282 on the replaceable core component may align with an adjacent graphical object 283 on the chassis to form a side-by-side composite graphical object when the predetermined position of the replaceable core component is reached. In yet another example of a visible insertion depth indicator, as shown in FIG. 44 and FIG. 45, a graphical object 282 on the replaceable core component may align with an adjacent graphical object 283 on the chassis to form an overlaid composite graphical object when the predetermined position of the replaceable core component is reached. In the latter example, the graphical object 282 on the replaceable core component may be visible through a translucent or transparent portion of the chassis layer coinciding with the graphical object 283 on the chassis.

Figure 46:
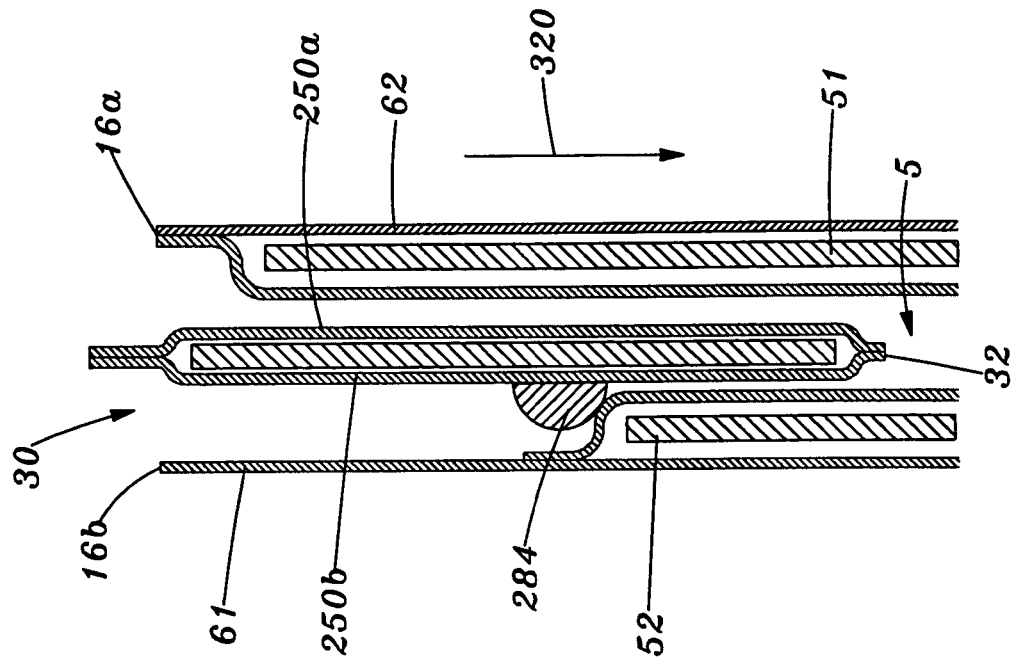
FIG. 46 is a partial section view showing a replaceable absorbent core component having a mechanical insertion depth indicator.
Figure 47:
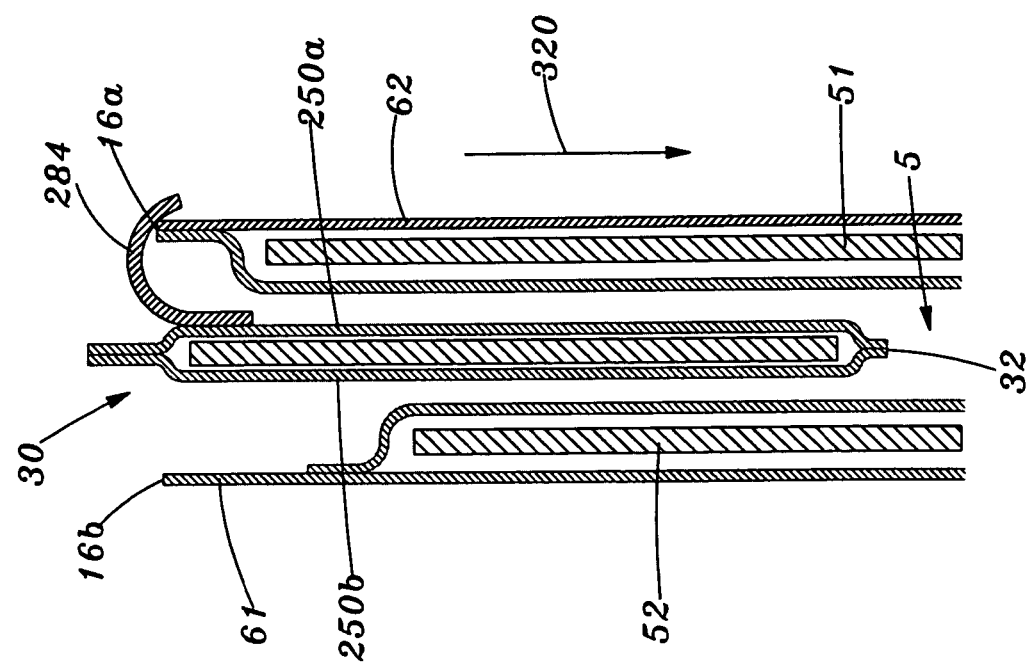
FIG. 47 is a partial section view showing a replaceable absorbent core component having another mechanical insertion depth indicator.

The insertion depth indicator may include a mechanical insertion depth indicator providing tactile feedback in some exemplary embodiments. For example, the insertion depth indicator may include a member disposed on the replaceable core component, for example, a mechanical surface fastener, such as either a hook member or a loop member, adapted to engage a complementary member disposed on the chassis or to engage a non-woven surface of the chassis when the predetermined position of the replaceable core component is reached. In another example of a mechanical insertion depth indicator, an outer surface of the replaceable core component may have a relatively higher coefficient of friction to a portion of an adjacent surface of the chassis, such that when the predetermined position of the replaceable core component is reached, an increase in the coefficient of friction markedly increases the force required to slide the replacement core component beyond the predetermined position. Such a mechanical insertion depth indicator may be disposed in the waist region, in the crotch region, or in both regions. In addition, such a mechanical insertion depth indicator may simultaneously serve as both an insertion depth indicator and a location stabilizer. For example, each of the location stabilizers 310 shown in FIG. 39 and FIG. 40 may also serve as a mechanical insertion depth indicator. Alternative forms of a mechanical insertion depth indicator are shown in FIG. 46 and FIG. 47, in which a mechanical insertion depth indicator 284 in the form of a protruding element prevents the insertion of the back panel 30 beyond a predetermined depth. As can be seen in these figures, a mechanical insertion depth indicator can be located anywhere between the ends of a replaceable core component. The mechanical insertion depth indicator may include a laterally extending or protruding element, in addition to or as an alternative to an element generally oriented in the thickness dimension of the replaceable core component such as described above. For example, the outer end segment of a replaceable core component may include a laterally extending portion that prevents the insertion of the back panel 30 beyond a predetermined depth, thus functioning similarly to the mechanical insertion depth indicator 284 in the form of a protruding element depicted in FIG. 46 and FIG. 47.

In some exemplary embodiments, an outer surface of the replaceable core component or an element disposed on the outer surface may have a directional coefficient of friction relative to the adjacent surfaces of the chassis and thereby provide tactile feedback related to whether or not the replaceable core component is being inserted in the intended end-to-end orientation. In such embodiments, a material forming the surface of the replaceable core component and having directional frictional characteristics may be oriented such that when the inner end of the replaceable core component is inserted first, the coefficient of sliding friction is relatively low, thus making the insertion of the replaceable core component into the chassis relatively easy. On the other hand, if the insertion of an inverted replaceable core component, i.e., a replaceable core component oriented such that its outer end is being inserted first, is attempted, a relatively higher coefficient of sliding friction of the directional material may provide a higher resistive force and, thus, make the insertion of the inverted replaceable core component into the chassis relatively more difficult. Such a directional frictional surface material may include, for example, a fabric having a directional nap or grain, a sheet having oriented protrusions or protuberances, a sheet having oriented teeth or hooks, or any other known structure having suitable directional frictional characteristics.

Figure 49:
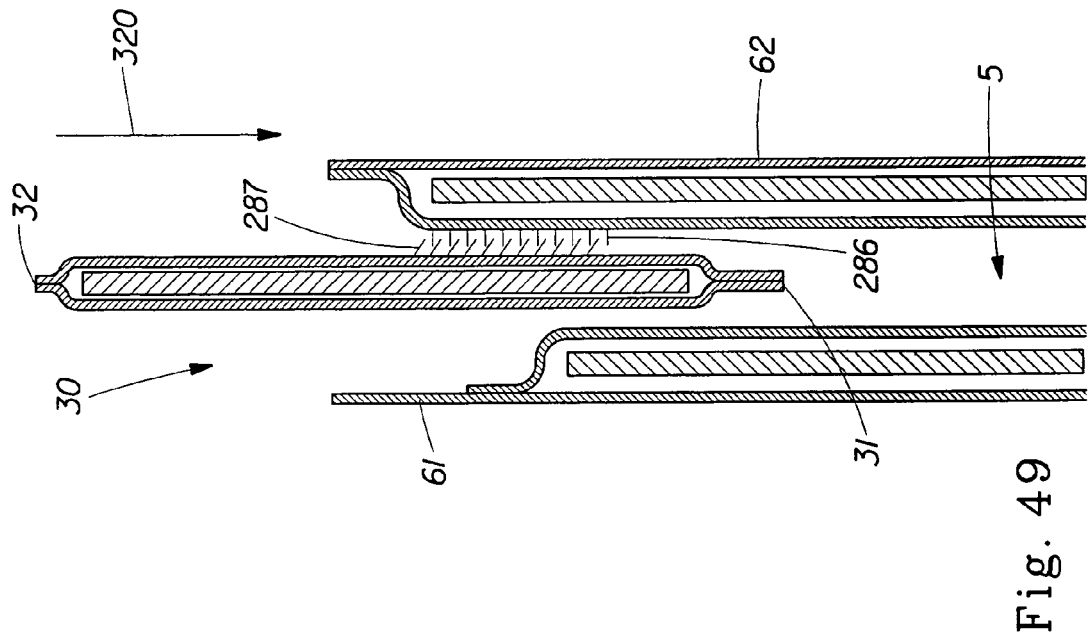
FIG. 49 is a partial section view showing the replaceable absorbent core component of FIG. 48 in an improper end-to-end orientation.
Figure 48:
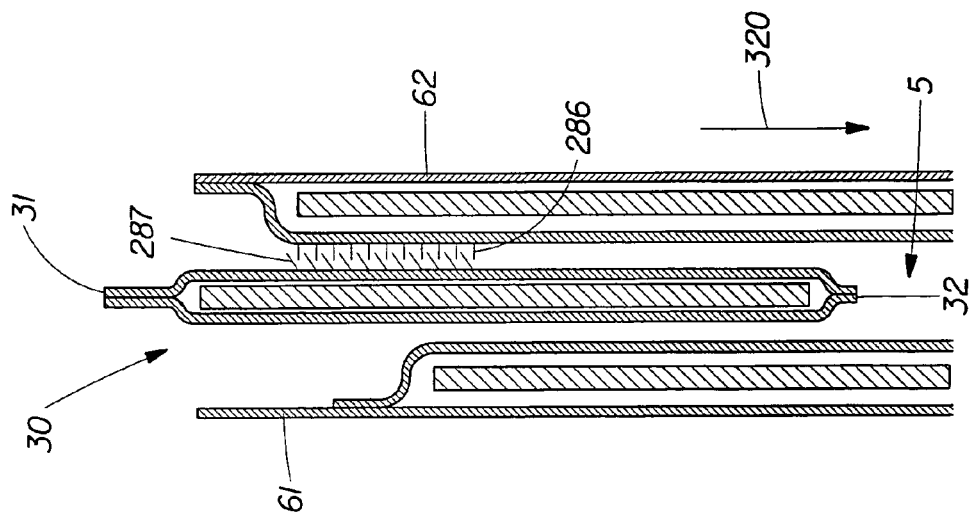
FIG. 48 is a partial section view showing a replaceable absorbent core component having directional coefficient of friction elements in a proper end-to-end orientation.

For example, in FIG. 48 and FIG. 49, the directional coefficient of friction is illustratively represented by the angled teeth 287 pointing toward the outer end 31 of the back panel 30 and the perpendicular teeth 286, such that movement of the back panel 30 in one direction can be visualized as causing the angled teeth to flex against the perpendicular teeth 286 and thereby present relatively little resistance to the movement, while movement of the back panel in an opposing direction can be visualized as causing the angled teeth to jam against the perpendicular teeth and thereby present relatively greater resistance to movement in this opposing direction. In FIG. 48, the back panel 30 is shown as oriented in the intended end-to-end orientation such that its inner end 32 is being inserted first. In this figure, movement of the back panel 30 in an inward direction, i.e., in a direction from its outer end 31 toward its inner end 32, can be visualized as causing the angled teeth 287 to flex against the perpendicular teeth 286 and thereby present relatively little resistance to the inward movement. On the other hand, in FIG. 49, the back panel 30 is shown as oriented oppositely to the intended end-to-end orientation such that its outer end 31 is being inserted first. In this figure, movement of the back panel 30 in an inward direction, i.e., in a direction from its inner end 32 toward its outer end 31, can be visualized as causing the angled teeth 287 to jam against the perpendicular teeth 286 and thereby present relatively greater resistance to the inward movement.

The directional frictional characteristics may tend to resist the outward movement of a replaceable core component that has been inserted in the intended end-to-end orientation in the chassis. For example, movement of the back panel 30 in FIG. 48 in an outward direction can be visualized as causing the angled teeth 287 to jam against the perpendicular teeth 286 and thereby present relatively greater resistance to the outward movement. Thus, an additional benefit of the use of such a directionally frictional surface material is that the relatively high frictional force resisting the outward movement of a replaceable core component inserted in the intended predetermined orientation may tend to assist in retaining the replaceable core component in the intended predetermined position after its insertion and this material may thereby serve as a location stabilizer.

In some exemplary embodiments, opposing outer surfaces of the replaceable core component may have different coefficients of friction relative to the adjacent surfaces of the chassis and thereby provide tactile feedback related to whether or not the replaceable core component is being inserted in the intended orientation of its predetermined wearer-facing and garment-facing surfaces. For example, in such embodiments, a material forming the wearer-facing surface of the replaceable core component and having directional frictional characteristics may be oriented such that when the replaceable core component is inserted with its predetermined wearer-facing surface oriented toward the wearer-facing layer of the chassis and with its predetermined garment-facing surface oriented toward the garment-facing layer of the chassis, the coefficient of sliding friction is relatively low, thus making the insertion of the replaceable core component into the chassis relatively easy. On the other hand, if the insertion of a reversed replaceable core component, i.e., a replaceable core component oriented such that its wearer-facing and garment-facing surfaces are reversed from its intended orientation, is attempted, a relatively higher coefficient of sliding friction of the directional material may provide a higher resistive force and, thus, make the insertion of the reversed replaceable core component into the chassis relatively more difficult. Such a directional frictional surface material may include, for example, a fabric having a directional nap or grain, a sheet having oriented protrusions or protuberances, a sheet having oriented teeth or hooks, or any other known structure having suitable directional frictional characteristics. This directional frictional surface material may be disposed on one or more of the major surfaces of the replaceable core component or may be disposed on laterally opposing edge surfaces.

Figure 50:
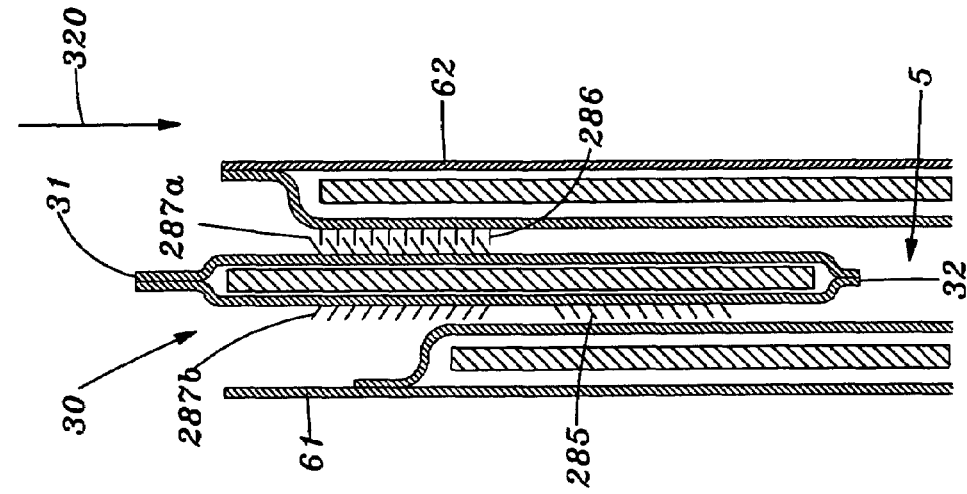
FIG. 50 is a partial section view showing a replaceable absorbent core component having directional coefficient of friction elements in a proper orientation of its wearer-facing and garment-facing surfaces.
Figure 51:
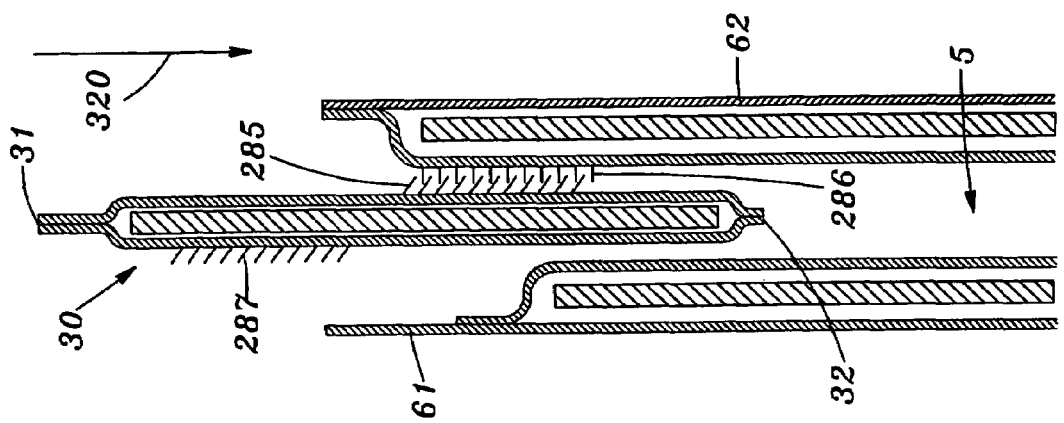
FIG. 51 is a partial section view showing the replaceable absorbent core component of FIG. 50 in an improper orientation of its wearer-facing and garment-facing surfaces.

For example, in FIG. 50 and FIG. 51, the directional coefficient of friction is represented by the first angled teeth 285, pointing toward the inner end 32 of the back panel 30, the second angled teeth 287, pointing toward the outer end 31 of the back panel 30, and the perpendicular teeth 286, such that movement of the back panel 30 in one direction can be visualized as causing the angled teeth to flex against the perpendicular teeth 286 and thereby present relatively little resistance to the movement, while movement of the back panel in an opposing direction can be visualized as causing the angled teeth to jam against the perpendicular teeth and thereby present relatively greater resistance to movement in this opposing direction. In FIG. 50, the back panel 30 is shown as oriented in the intended orientation of its predetermined wearer-facing and garment-facing surfaces such that the second angled teeth 287 are oriented toward the perpendicular teeth 286 and the first angled teeth 285 are oriented away from the perpendicular teeth 286. In this figure, movement of the back panel 30 in an inward direction, i.e., in a direction from its outer end 31 toward its inner end 32, can be visualized as causing the second angled teeth 287 to flex against the perpendicular teeth 286 and thereby present relatively little resistance to the inward movement. On the other hand, in FIG. 51, the back panel 30 is shown as oriented oppositely to the intended orientation of its predetermined wearer-facing and garment-facing surfaces such that the first angled teeth 285 are oriented toward the perpendicular teeth 286 and the second angled teeth 287 are oriented away from the perpendicular teeth 286. In this figure, movement of the back panel 30 in an inward direction, i.e., in a direction from its outer end 31 toward its inner end 32, can be visualized as causing the first angled teeth 285 to jam against the perpendicular teeth 286 and thereby present relatively greater resistance to the inward movement.

The directional frictional characteristics may tend to resist the outward movement of a replaceable core component that has been inserted in the intended orientation of its predetermined wearer-facing and garment-facing surfaces. For example, movement of the back panel 30 in FIG. 50 in an outward direction can be visualized as causing the second angled teeth 287 to jam against the perpendicular teeth 286 and thereby present relatively greater resistance to the outward movement. Thus, an additional benefit of the use of such a directionally frictional surface material is that the relatively high frictional force resisting the outward movement of a replaceable core component inserted in the intended predetermined orientation may tend to assist in retaining the replaceable core component in the intended predetermined position after its insertion and this material may thereby serve as a location stabilizer.

Figure 52:
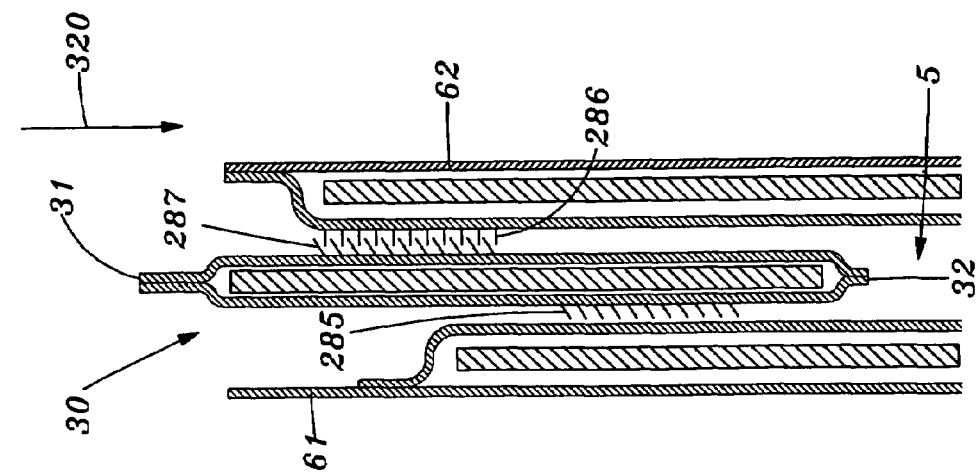
FIG. 52 is a partial section view showing a replaceable absorbent core component having directional coefficient of friction elements in a proper orientation of both its wearer-facing and garment-facing surfaces and its inner and outer ends.
Figure 57:
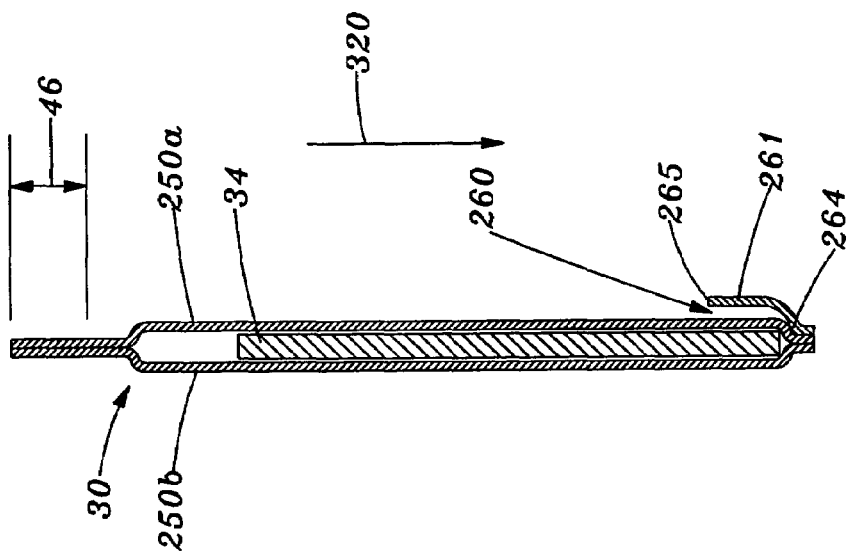
FIG. 57 is a partial section view showing the replaceable absorbent core component of FIG. 56.

The elements having the directional frictional characteristics described above may be combined in various ways to provide tactile feedback related to both related to whether or not the replaceable core component is being inserted in the intended end-to-end orientation and whether or not the replaceable core component is being inserted in the intended orientation of its predetermined wearer-facing and garment-facing surfaces. For example, as shown in FIG. 52, FIG. 53, FIG. 54, and FIG. 55, each of the first angled teeth 285, pointing toward the inner end 32 of the back panel 30, the second angled teeth 287, pointing toward the outer end 31 of the back panel 30, and the perpendicular teeth 286, again represent the directional coefficient of friction. In FIG. 52, the back panel 30 is oriented in the intended end-to-end orientation and in the intended orientation of its predetermined wearer-facing and garment-facing surfaces, such that movement of the back panel 30 in the insertion direction 320 can be visualized as causing the second angled teeth 287a to flex against the perpendicular teeth 286 and thereby present relatively little resistance to the movement. However, in FIG. 53, the back panel 30 is shown as oriented oppositely to the intended orientation of its predetermined wearer-facing and garment-facing surfaces, such that movement of the back panel 30 in the insertion direction 320 can be visualized as causing the first angled teeth 285 to jam against the perpendicular teeth 286 and thereby present relatively greater resistance to the inward movement. Then, in FIG. 54, the back panel 30 is shown as oriented oppositely to the intended end-to-end orientation such that its outer end 31 is being inserted first. In this figure, movement of the back panel 30 in an inward direction, i.e., in a direction from its inner end 32 toward its outer end 31, can be visualized as causing the angled teeth 287a to jam against the perpendicular teeth 286 and thereby present relatively greater resistance to the inward movement. Finally, in FIG. 55, the back panel 30 is shown as oriented oppositely to the intended end-to-end orientation and oppositely to the intended orientation of its predetermined wearer-facing and garment-facing surfaces. In this figure, movement of the back panel 30 in an inward direction, i.e., in a direction from its inner end 32 toward its outer end 31, can be visualized as causing the angled teeth 287b to jam against the perpendicular teeth 286 and thereby present relatively greater resistance to the inward movement.

As shown in FIG. 56, FIG. 57, FIG. 58, FIG. 59, FIG. 60, FIG. 61, FIG. 62, FIG. 63, FIG. 64, and FIG. 65, the replaceable core component may include an openable insertion pocket 260 into which a finger or fingers or an insertion tool 270 may be inserted for the application of a force to insert the replaceable core component into the chassis in the intended predetermined orientation. Such an insertion force is applied in a direction indicated by the arrow 320 from the outer end toward the inner end of the replaceable core component, e.g., in a direction from the outer end 31 toward the inner end 32 of the back panel 30. For example, the back panel 30 may have a piece of sheet material 261 joined to its outer surface by continuous linear bonds or by an array of spot bonds, or any combination thereof, to form the openable insertion pocket having an outer end edge 265, an inner end 264, and an openable end 263 located at its outer end edge and facing toward the outer end 31 of the back panel 30. The bonds 262 may be formed by any means known in the art, including ultrasonic bonding, heat bonding, pressure bonding, or adhesive bonding. In general, any piece of sheet material joined along at least two of its edges to an outer surface of the replaceable core component may form the openable insertion pocket. However, such a sheet may alternatively be bonded elsewhere, e.g., inboard of its edges, in any pattern that forms an openable pocket-like space that can similarly serve as an openable insertion pocket, i.e., that can be used in functional cooperation with the fingers or the insertion tool inserted into this pocket-like space to exert an insertion force in the direction 320 to insert the replaceable core component into the chassis in the intended predetermined orientation. For example, the bonds may have the form of the intermittent linear bonds 262 shown in FIG. 60 or the form of the spot bonds 262 shown in FIG. 61 and in FIG. 63. Such an openable insertion pocket may be disposed on one major surface of the replaceable core component or two openable insertion pockets may be disposed on the opposing major surfaces of the replaceable core component, as shown in FIG. 64 and FIG. 65. The openable insertion pocket is preferably disposed in the inner end segment of the replaceable core component. In some embodiments, an insertion tool may be predisposed inside the openable insertion pocket of the replaceable core component.

Figure 56:
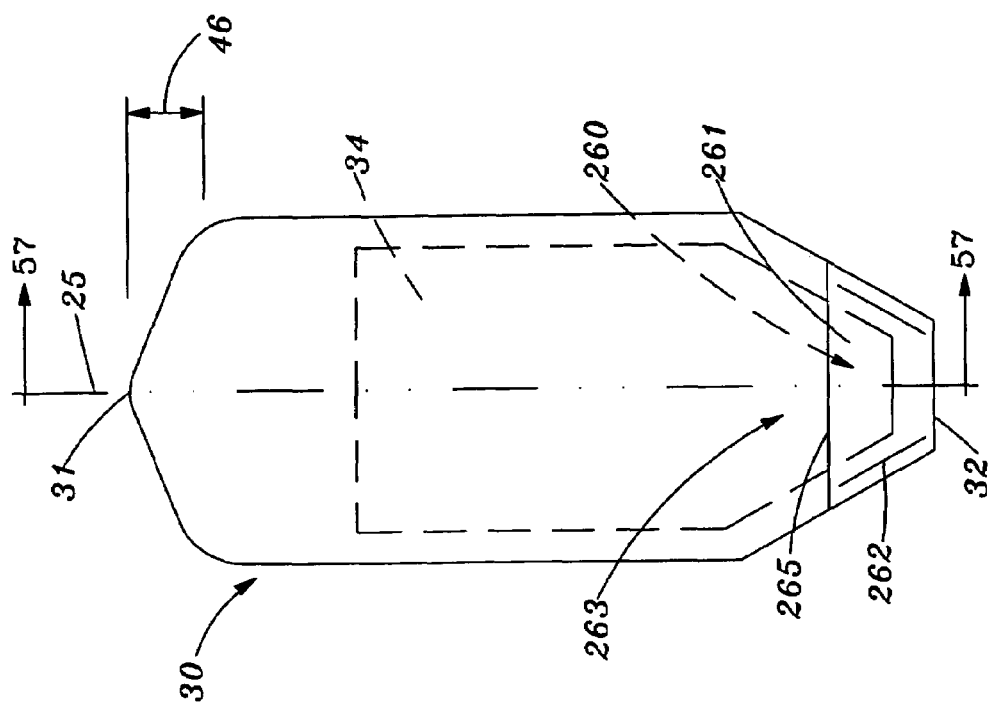
FIG. 56 is a plan view showing a replaceable absorbent core component having a relatively shallow insertion pocket on its outer surface.
Figure 68:
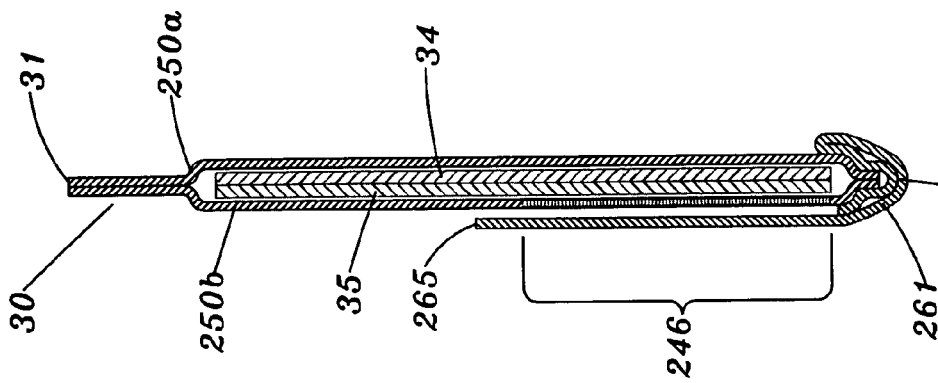
FIG. 68 is a partial section view showing the insertion pocket sheet of FIG. 67 folded over the inner end of the replaceable absorbent component to cover a permeable region for disposal.
Figure 67:
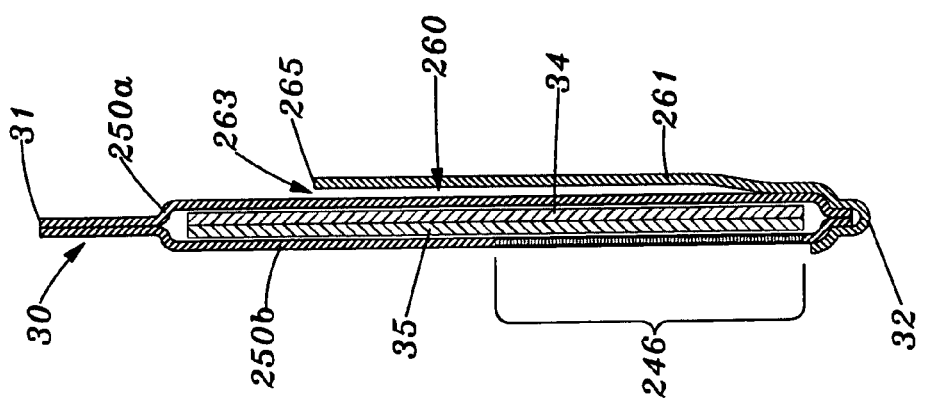
FIG. 67 is a partial section view showing a replaceable absorbent core component having an insertion pocket sheet in its initial pocket-forming configuration.
Figure 66:
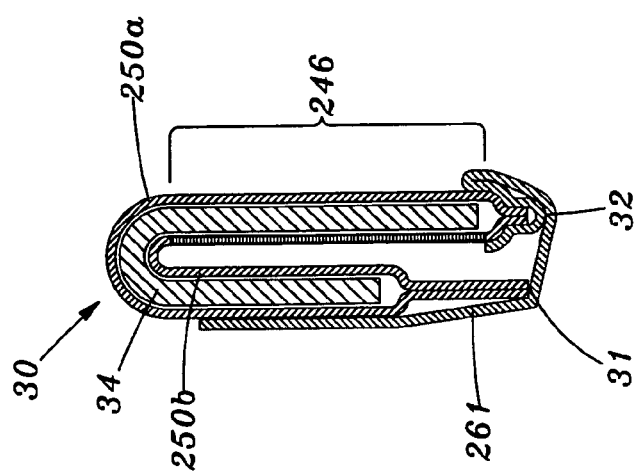
FIG. 66 is a partial section view showing a replaceable absorbent core component folded inside an extensible insertion pocket layer for disposable.

The openable insertion pocket may be of sufficient size to accept only a finger or fingers, of sufficient size to accept an entire hand of a caregiver, or of sufficient size to accept an insertion tool. A length of the insert pocket may be measured along the longitudinal centerline of the replaceable core component from the innermost end of the openable insertion pocket adjacent to the inner end of the replaceable core component to the outermost end of the openable insertion pocket. The length of the openable insertion pocket may be at least about 10% of the length of the replaceable core component, as shown in FIG. 56, and preferably is at least about 20%, as shown in FIG. 62, more preferably is at least about 40%, as shown in FIG. 63, and most preferably is at least about 60%, as shown in FIG. 58, of the length of the replaceable core component. The insertion pocket sheet material may be liquid impervious, but preferably is liquid pervious. The insertion pocket sheet material may be extensible to enable the openable insertion pocket to expand to accommodate the hand of the caregiver or to be wrapped around a folded replaceable core component for disposal, as shown in FIG. 66, or around an end of an unfolded replaceable core component to cover a portion of the opposing surface for disposal. For example, the insertion pocket sheet 261 shown in FIG. 67 may be folded around the inner end 32 of the back panel 30 to cover the permeable liquid transfer region 246 for disposal, as shown in FIG. 68. Preferably, the insertion pocket sheet material is elastically extensible. In some embodiments, the insertion pocket sheet 261 may be partially detachable, such as by means of perforations or a releasable adhesive attachment, from the surface of the replaceable core component to allow the insertion pocket sheet to be folded over a portion of the replaceable core component and thereby cover the permeable liquid transfer region 246 of the replaceable core component for disposal.

The replaceable core component may include a covering sheet 249, which may be liquid pervious or liquid impervious, covering a portion of a first major surface 251 of the replaceable core component and wrapping over an edge of the replaceable core component, such as the inner end 32 of the back panel 30, to cover at least a portion of the opposing second major surface 252 of the replaceable core component, as shown in FIG. 69. In such an embodiment, the wrapped over covering sheet 249 may form an openable insertion pocket 260 and thereby serve as an insertion pocket sheet 261 on one side of the replaceable core component, as shown in FIG. 70, or may form openable insertion pockets on both sides of the replaceable core component. The covering sheet 249 can also be wrapped completely around the replaceable core component and joined where its opposing edge margins overlap to form a tube-like structure enveloping the replaceable core component. In some embodiments, such a covering sheet that is liquid impervious may form a portion of the outer end segment and/or a portion of the pull tab, thereby preventing liquid in the absorbent layer from wetting the outer surface of this portion of the replaceable core component.

Figure 71:
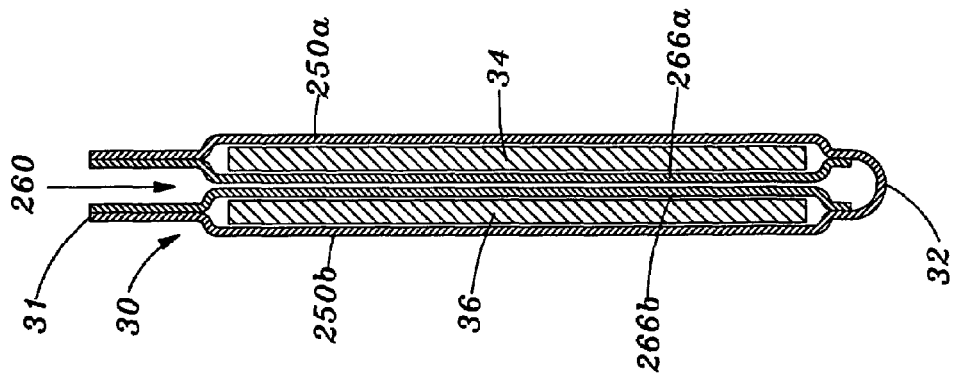
FIG. 71 is a partial section view showing a replaceable absorbent core component having an internal insertion pocket formed between absorbent layers.
Figure 72:
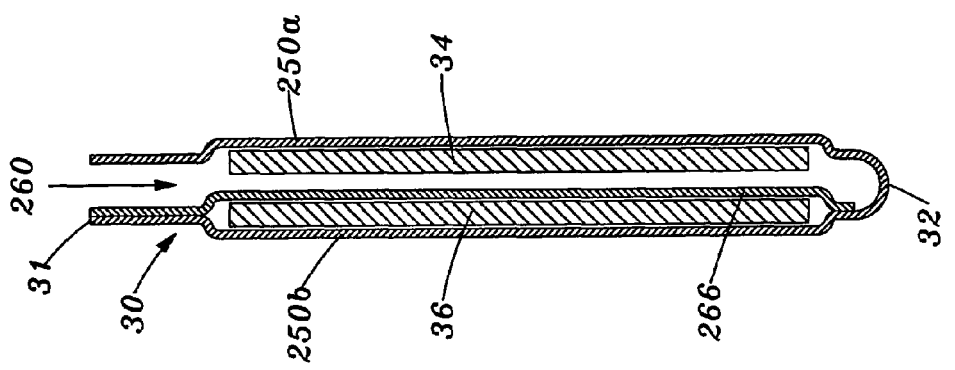
FIG. 72 is a partial section view showing a replaceable absorbent core component having an internal insertion pocket formed between an absorbent layer and an inner layer.
Figure 73:
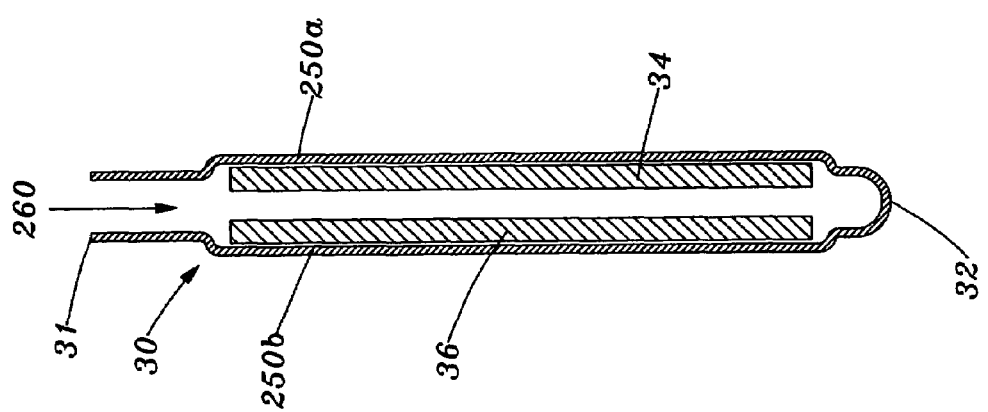
FIG. 73 is a partial section view showing a replaceable absorbent core component having an internal insertion pocket formed between two inner layers.

The openable insertion pocket 260 may also be formed internally to the replaceable core component. For example, an internal insertion pocket 260 may be formed in the back panel 30 between an absorbent layer 34 and a superposed absorbent layer 36, as shown in FIG. 71, between an absorbent layer 34 and an inner layer 266, as shown in FIG. 72, or between two inner layers 266*a* and 266*b*, as shown in FIG. 73. In such an embodiment, a finger or fingers or an insertion tool may be inserted into the internal insertion pocket for the application of a force to insert the replaceable core component into the chassis in the intended predetermined orientation. The layers forming the internal insertion pocket may be liquid pervious, thereby permitting the passage of liquid from one absorbent layer of the replaceable core component to another absorbent layer disposed on the opposing side of the internal insertion pocket. Alternatively, one or more of the layers forming the internal insertion pocket may be liquid impervious and thereby act as a barrier to liquid flow between the absorbent layer or layers and the internal insertion pocket. For example, the inner layer 266 may be liquid pervious or liquid impervious.

Figure 74:
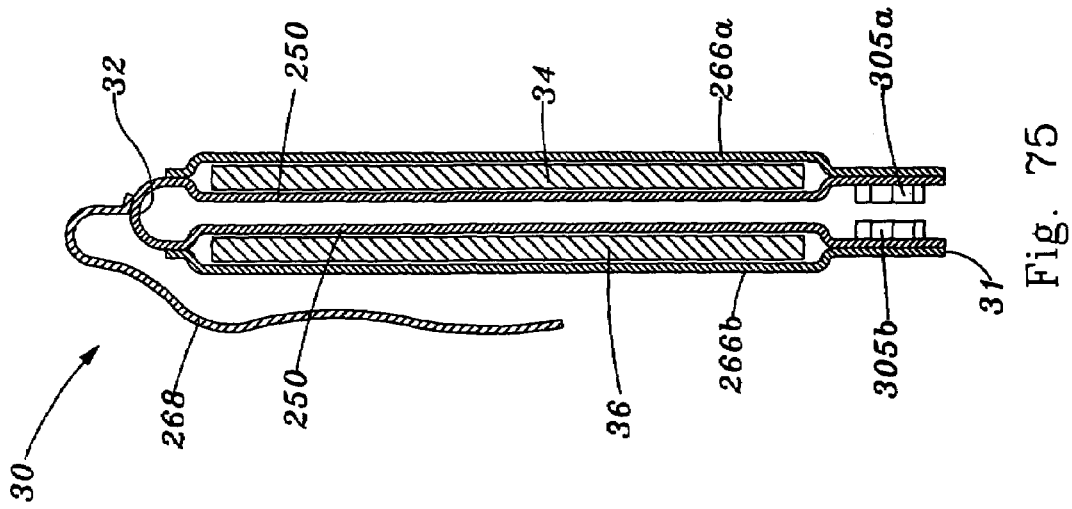
FIG. 74 is a partial section view showing a replaceable absorbent core component having an internal insertion pocket and an inverting pull tab in its initial state.
Figure 75:
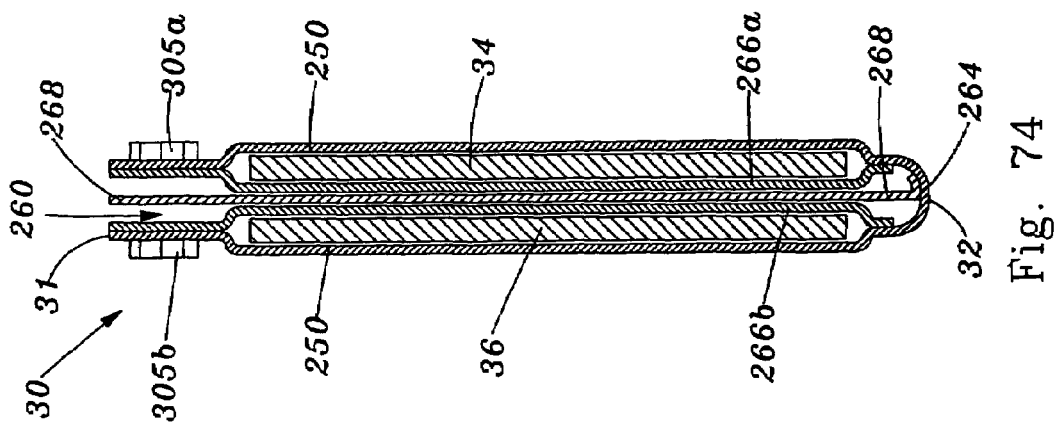
FIG. 75 is a partial section view showing the replaceable absorbent core component of FIG. 74 in its inverted state.

A replaceable core component having an internal insertion pocket may include an inverting pull tab 268 disposed inside the internal insertion pocket and extending from the inner end 264 of the internal insertion pocket adjacent to the inner end segment of the replaceable core component toward the outer end segment of the replaceable core component, as shown in FIG. 74. When the inverting pull tab is pulled toward the outer end of the replaceable core component, the replaceable core component is inverted, i.e., turned inside out, by drawing the inner end of the replaceable core component into and through the internal insertion pocket, such that the original outer layers of the replaceable core component are drawn inside and the original inner layers of the internal insertion pocket are drawn to the outside of the inverted replaceable core component. In other words, when inverted, the replaceable core component is turned inside out and wrapped within the original inner layers 266, as shown in FIG. 75. In this invertable embodiment, it is preferred that the inner layers be liquid impervious, so that the inverted replaceable core component is wrapped within these liquid impermeable layers for disposal. Also, the outer end segment of the replaceable core component may be releasably attached to the chassis when the replaceable core component is in the absorbent article, such that during removal of the replaceable core component from the absorbent article, the outer end segment is temporarily held by the releasable attachment means 305, thereby causing the replaceable core component to invert, i.e., turn inside out, as it is withdrawn. Once the replaceable core component is fully withdrawn from the chassis, the releasable attachment means may release the outer end segment and the original inner layers may then continue to cover the replaceable core component. In some embodiments, the releasable attachment means may be fastened together to secure the replaceable core component in the inverted configuration.

The replaceable core component needs to extend only from the crotch region to one of the waist regions of the article. However, the replaceable core component preferably extends from the crotch region beyond a waist end edge of one of the waist regions, so that the outer end of the replaceable core component is exposed and thereby visible when the absorbent article is worn. To this point in this disclosure, the outer end 31 of the back panel 30 has been shown extending beyond the adjacent waist end edge 16 in this manner in FIG. 17, FIG. 18, FIG. 28, FIG. 41, FIG. 43, and FIG. 45.

Figure 76:
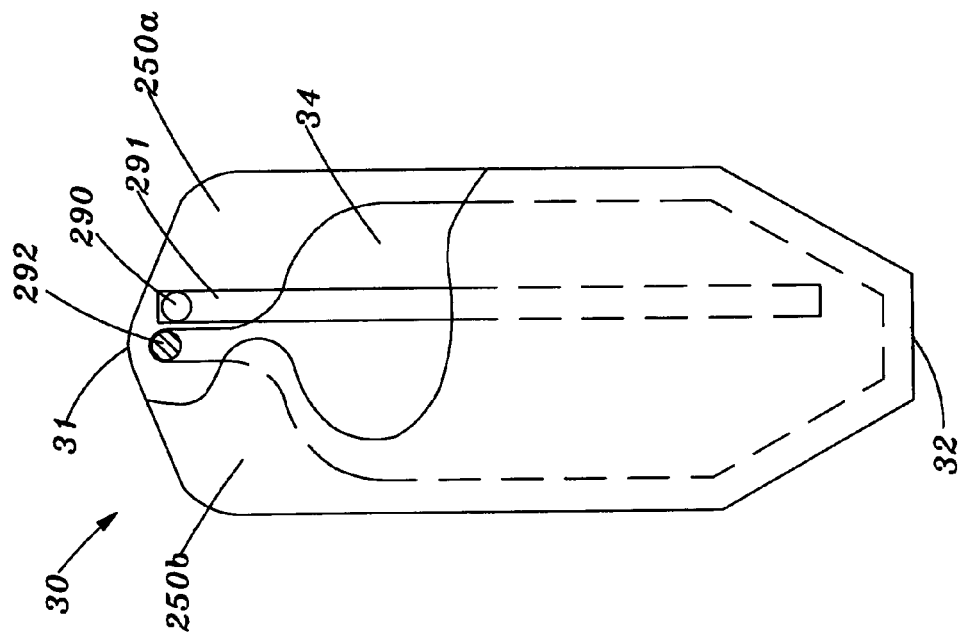
FIG. 76 is a plan view showing a replaceable absorbent core component having a liquid presence indicator including wicking strips.
Figure 77:
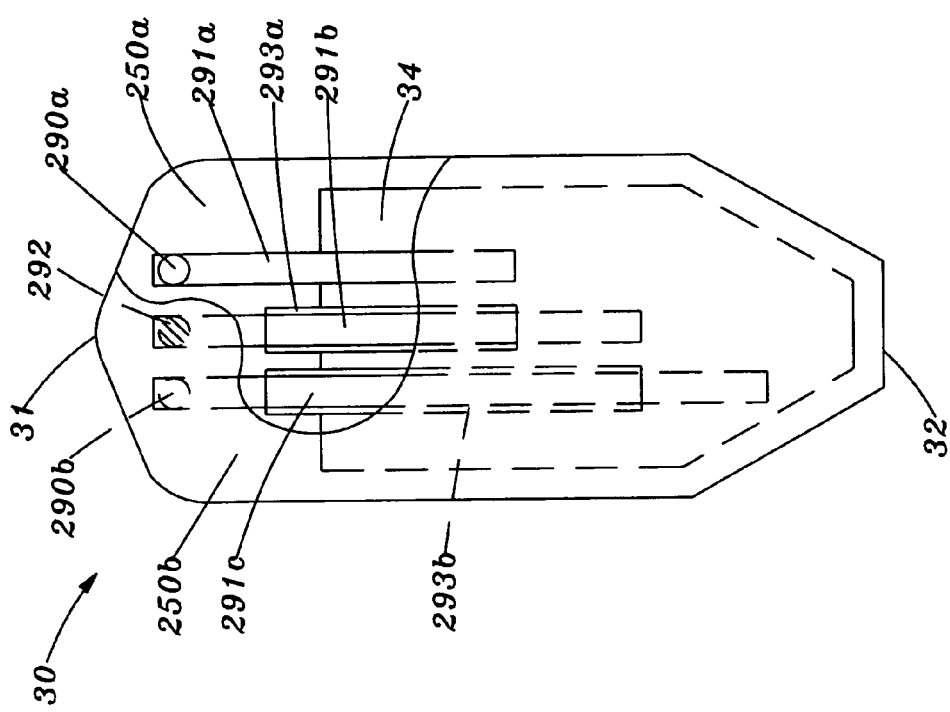
FIG. 77 is a plan view showing a replaceable absorbent core component having a liquid presence indicator including an indicating composition disposed on an absorbent layer.

A portion of the replaceable core component extending beyond the waist end edge may include a liquid presence indicator 290 adapted to provide an indication of a wetted condition of the replaceable core component. The liquid presence indicator may include multiple strips 291 of wicking material, as shown in FIG. 76, which may have differing characteristics such as the lengths of the strips, the thicknesses of the strips, the shapes and areas of the strips, the pore sizes of the wicking materials used in the various strips, the absorbent capacities of the strips, the degrees of hydrophilicity of the strips, and etc. A single wicking strip 291 may also be used, as shown in FIG. 77. A suitable wicking strip 291 may have a 30 minute vertical wicking height of at least 10 cm and, preferably, may have a 30 minute vertical wicking height of at least 20 cm or, more preferably, of at least 30 cm. The wicking strips may include such materials as high surface area fibers, capillary channel filaments, open celled polymeric foams, and/or densified cellulose substrates. The wicking strips may be disposed within the replaceable core component, e.g., the back panel 30, such that at least one of the wicking strips extends from the permeable liquid transfer region of the replaceable core component to the outer end segment. Each of the wicking strips is preferably in capillary liquid communication with at least a portion of the storage/redistribution member of the replaceable core component. A portion of the wicking strip may also be isolated from the storage/redistribution member by a liquid impermeable layer 293 disposed between the wicking strip and the absorbent layer of the replaceable core component. The wicking strip may have a visible liquid presence indication means 292 disposed on or adjacent to its outer end. The visible indication means may include a pH-activated or moisture-activated material, which may be applied to the wicking strip in the form of a hotmelt adhesive in some exemplary embodiments. Preferably, the visible indication means is visible through the material forming the outer surface of the replaceable core component, making it unnecessary for the wicking strip or strips to extend beyond the outer end of the replaceable core component in order to be visible.

In some exemplary embodiments, the liquid presence indicator 290 may include an indicating composition disposed on an absorbent layer of the replaceable core component, such as a storage member or a storage/redistribution member, as shown in FIG. 77. Such an indicating composition may preferably be disposed on the absorbent layer in the outer end segment of the replaceable core component. The indicating composition may provide a visible indication and may include a pH-activated or moisture-activated material, which may be applied to the absorbent layer in the form of a hotmelt adhesive or a water-soluble dye in some exemplary embodiments. The visible liquid presence indication means 292 is preferably disposed above the waist end edge of the chassis when the replaceable core component is inserted to the intended predetermined depth in the chassis.

Figure 79:
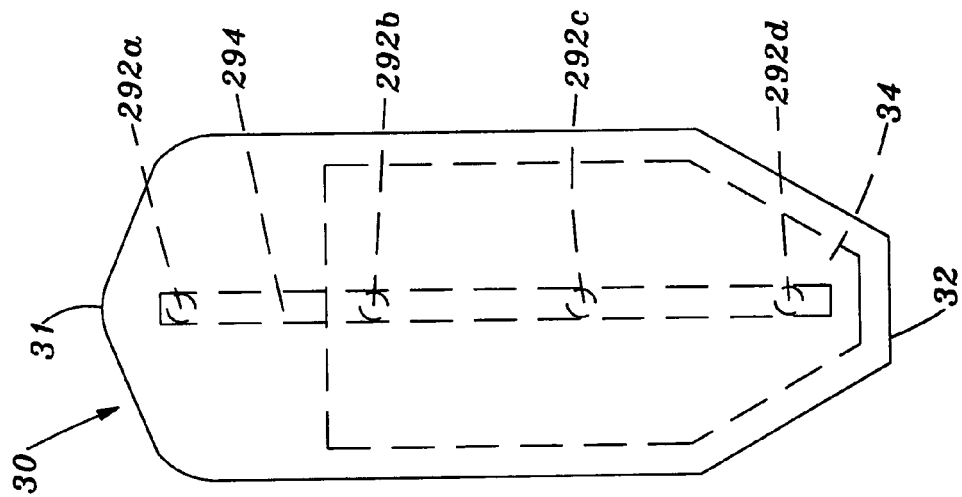
FIG. 79 is a plan view showing a replaceable absorbent core component having a liquid presence indicator in the form of a stationary absorbent strip including a series of visible liquid presence indication means.
Figure 78:
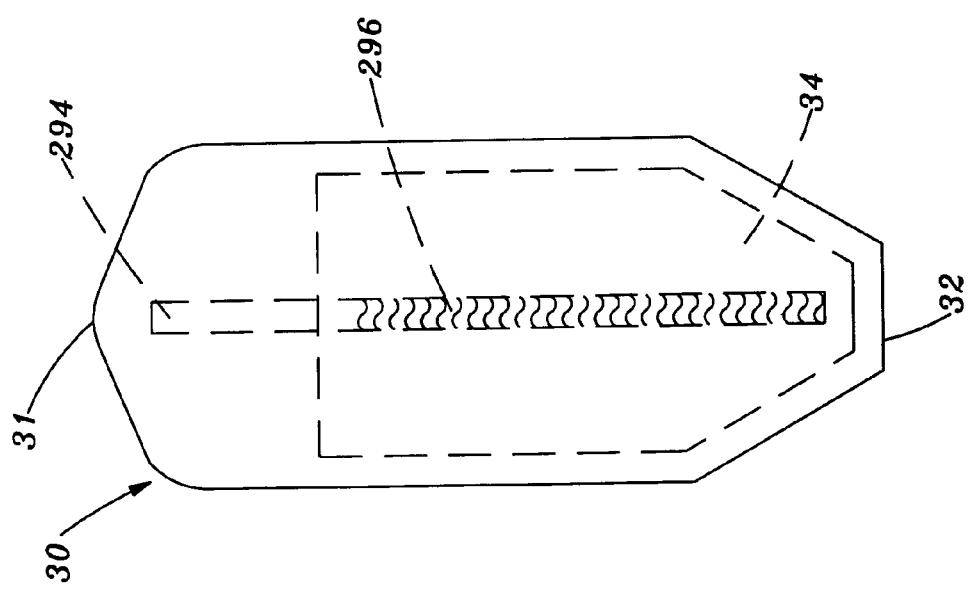
FIG. 78 is a plan view showing a replaceable absorbent core component having a liquid presence indicator in the form of a stationary absorbent strip indicating a wetted area.

However, in some embodiments, the visible indication means may be disposed below the waist end edge, i.e., between the backsheet and the wearer in the waist region of the article, when the replaceable core component is inserted to the intended predetermined depth. For example, a stationary absorbent strip 294 including a litmus paper-like substrate that changes color in a wetted area 296, as shown in FIG. 78, or a series of visible liquid presence indication means 292, as shown in FIG. 79, each of which undergoes a visible change in response to a liquid presence or to the pH of a liquid contacting the indication means. As another example, a pH-activated or moisture-activated material may be applied in a stripe on the outer surface of the replaceable core component. These approaches of providing a "liquid level" indication enable the user to assess the actual level of liquid loading in the replaceable core component, in addition to determining the presence of liquid. In some embodiments, the visible indication means may be visible through the backsheet when the replaceable core component is inserted to the intended predetermined depth. The replaceable core component may have a translucent or transparent region through which the liquid presence indication means is visible and, in some embodiments, a replaceable core component having a visible liquid presence indication means may be used in a chassis having a transparent or translucent region in the backsheet that aligns with the visible indication means when the replaceable core component is inserted into the article to the intended predetermined depth and in the intended predetermined position and orientation.

Some exemplary embodiments may have a "dipstick" type visible liquid presence indicator, as shown in FIG. 80, in which an absorbent strip 294 can be moved through a slit 295 in an outer layer of the replaceable core component between a fully inserted position within the replaceable core component and a partially inserted position, thereby exposing an inner portion of the visible liquid presence indication absorbent strip and facilitating a determination of the level to which the replaceable core component has been wetted. The usage of such a "dipstick" type visible liquid presence indication absorbent strip is similar to that of using a dipstick to check the fluid levels in an automobile engine, the fuel level in an aircraft fuel tank, or the level in an in-ground storage tank. The "dipstick" type visible liquid presence indication absorbent strip can include a litmus paper-like substrate that changes color in a wetted area 296, as shown in FIG. 81, or can include a series of visible liquid presence indication means 292, as shown in FIG. 82, each of which undergoes a visible change in response to a liquid presence or to the pH of a liquid contacting the indication means. The dipstick approach enables the user to assess the actual level of liquid loading in the replaceable core component, in addition to determining the presence of liquid.

Figure 84:
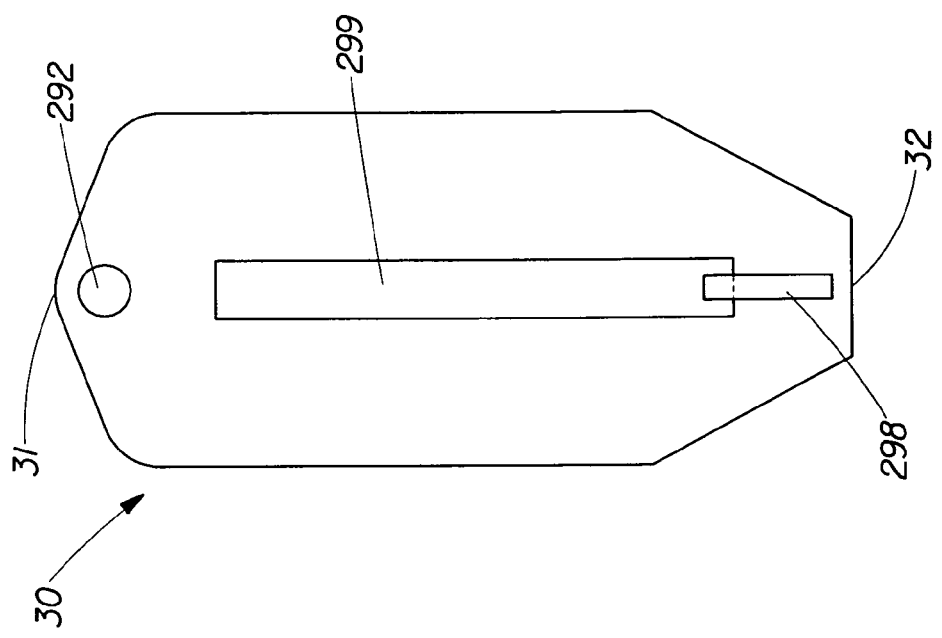
FIG. 84 is a plan view showing the liquid presence indicator of FIG. 83 after the movable indicator strip has moved to uncover it.
Figure 83:
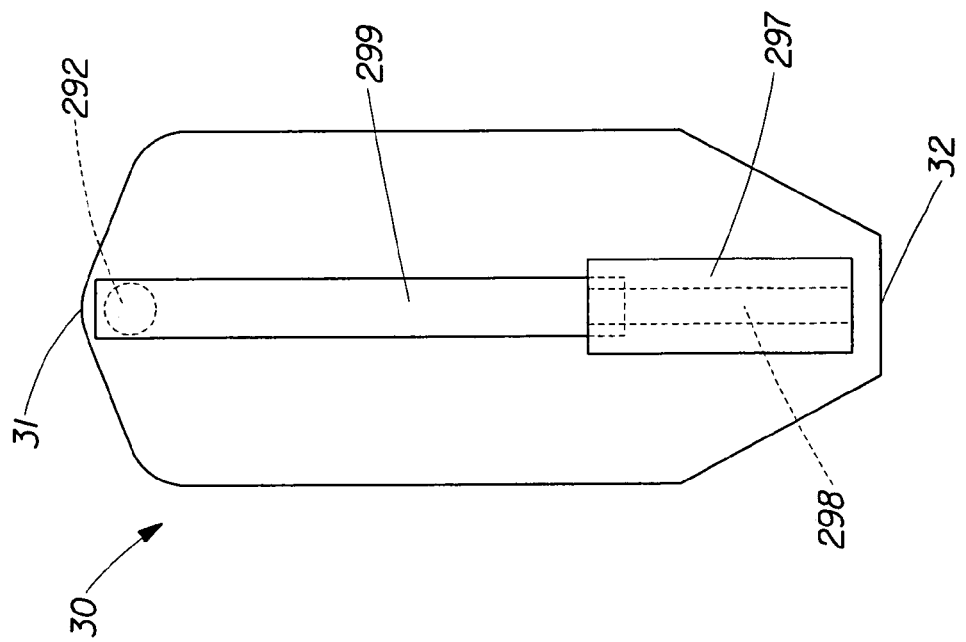
FIG. 83 is a plan view showing a replaceable absorbent core component having a liquid presence indicator covered by a movable indicator strip.

In some embodiments, the liquid presence indicator may include a water-sensitive restraining element whose dimension, tensile strength, resistance to compression, resistance to bending, or resistance to buckling is altered when it is contacted by water. The water-sensitive restraining element may include a water soluble material or a material that weakens, but does not dissolve, when wetted, such as cellulosic material. For example, as shown in FIG. 83 and FIG. 84, the liquid presence indicator may include a water-sensitive restraining element 297 joined to an elongated elastic force-generating element 298, either by joining the elastic element directly to the water-sensitive element or by attaching the water-sensitive element to an intermediate element that is attached to the elastic element. In its initial dry state, the water-sensitive element restrains the elastic element in its elongated state. When the water-sensitive element comes into contact with liquid as the product is loaded with bodily exudates, the water-sensitive element dissolves and releases the elastic element, thereby allowing the elastic element to relax by contracting. The resultant contraction of the elastic element moves a movable indicator strip 299 toward the inner end 32 of the back panel 30 to expose a visible liquid presence indication means 292 and thereby indicate the presence of liquid in the replaceable core component.

Figure 86:
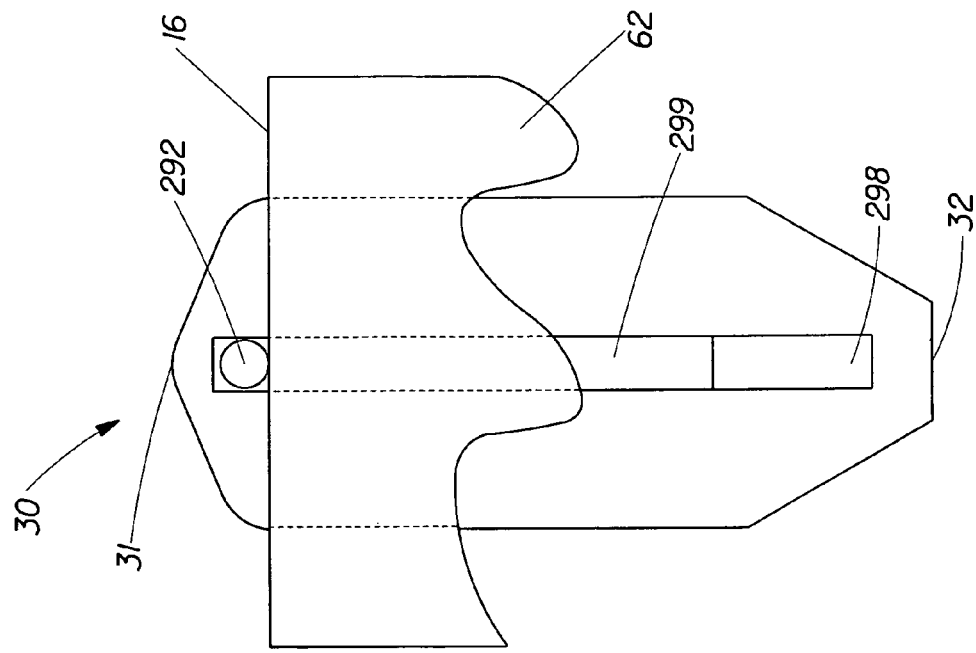
FIG. 86 is a plan view showing the liquid presence indicator of FIG. 85 after the movable indicator strip has moved to reveal it.
Figure 85:
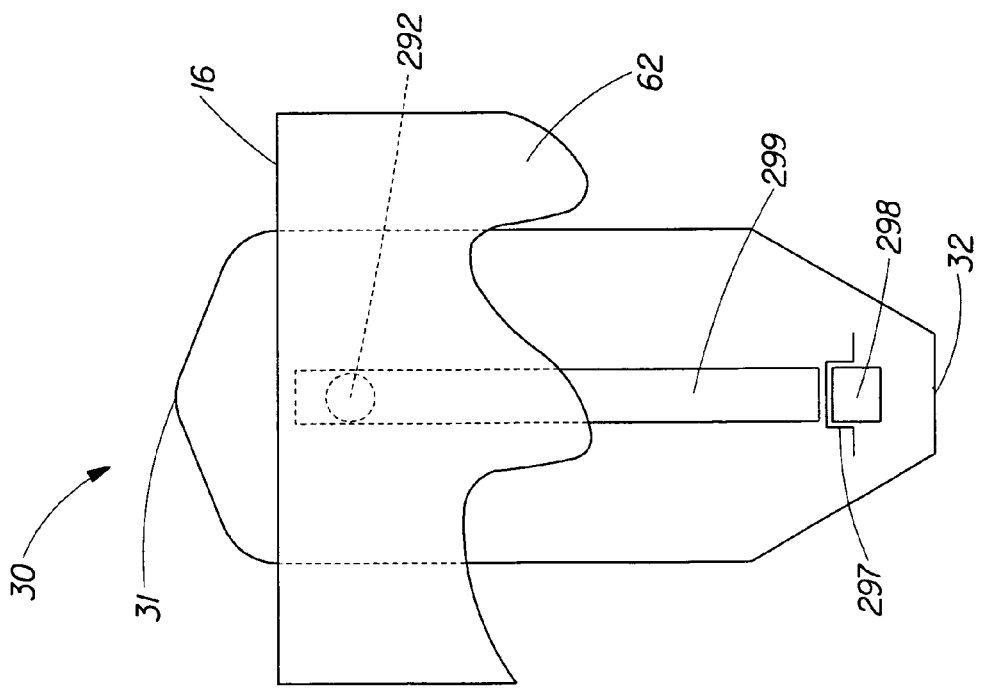
FIG. 85 is a plan view showing a replaceable absorbent core component having a liquid presence indicator disposed on a movable indicator strip and in its initial hidden state.

In other embodiments, the elastic force-generating element may initially be compressed, rather than elongated, and may relax by expanding, rather than contracting, when it is released. For example, as shown in FIG. 85 and FIG. 86, the visible liquid presence indication means 292 is disposed on the movable indicator strip 299 and is initially hidden below the waist end edge 16 of the chassis. The elastic element 298 is restrained in its initial compressed state by the water-sensitive restraining element 297. When the water-sensitive element comes into contact with liquid as the product is loaded with bodily exudates, the water-sensitive element dissolves and releases the elastic element, thereby allowing the elastic element to relax by expanding. The resultant expansion of the elastic element moves the movable indicator strip 299 toward the outer end 31 of the back panel 30, which outer end extends beyond the waist end edge of the chassis, to expose the visible liquid presence indication means 292 and thereby indicate the presence of liquid in the replaceable core component.

In some embodiments, a liquid presence indicator having a similar structure may provide a tactile indication of the presence of liquid in the replaceable core component. For example, when released, the elastic element may move a movable tactile indicator strip to a predetermined position in which the thickness of the strip provides the tactile impression of a raised area or a protuberance. As another example, when released, the elastic element may move a movable tactile indicator strip away from its initial position in which the thickness of the strip provided the tactile impression of a raised area or a protuberance and thereby eliminate that tactile impression, i.e., make the initially raised or protruding area feel smooth or flat.

The Insertion Tool

In order for the replaceable core component to be comfortable during wear, the replaceable core component is preferably relatively soft, relatively thin, and relatively flexible. However, the flexibility may make the insertion of the replaceable core component, by itself, difficult. For example, an attempt to insert the replaceable core component by grasping its outer end and pushing it into the chassis may result in the replaceable core component collapsing or buckling due to the sliding resistance between its outer surfaces and the adjacent surfaces of the chassis. Similarly, an attempt to insert the replaceable core component by grasping its inner end and inserting the grasping hand into the chassis may lead to wrinkling or folding of the replaceable core component. Also, the grasping hand may be too large to fit into the space into which the replaceable core component is being inserted and, therefore, only a partial insertion may be achieved.

Thus, the use of an insertion tool having a suitable thickness, a suitable stiffness, and a suitable buckling resistance may facilitate the insertion of the replaceable core component. Therefore, an absorbent article of the present invention may include an insertion tool for use in the application of a force to insert the replaceable core component into the chassis in the intended predetermined orientation. The use of such an insertion tool may obviate the need for a caregiver to insert her hand into the absorbent article when inserting a replaceable core component. Also, a suitable insertion tool may be significantly thinner than a human hand and thus facilitate the deeper insertion of the replaceable core component into the chassis, including when the chassis, or the margin of the openable end of an openable chassis pocket, is limited in its extensibility to accommodate the insertion. In different embodiments, the insertion tool may be withdrawn following the insertion of the replaceable core component or may remain in the chassis. Also, the insertion tool may be used without being attached to the replaceable core component, may be attached to the replaceable core component for its insertion and then detached from the replaceable core component, or may remain attached to the replaceable core component.

The insertion tool 270 may be inserted into an insertion pocket 260 attached on the outside of a replaceable core component, such as in the exemplary embodiments shown in FIG. 87, FIG. 88, FIG. 89, FIG. 90, FIG. 91, and FIG. 92, or it may be inserted into an internal insertion pocket formed internally of the replaceable core component, as described elsewhere in this disclosure. In some embodiments, two insertion tools may be inserted into two insertion pockets disposed on the opposing major surfaces of the replaceable core component, as shown in FIG. 93. When used in this manner, the two insertion tools may act as barriers preventing the exposure of the replaceable core component, for example, to the hand of a caregiver inserting the replaceable core component into the absorbent article. In addition, the surfaces of the two insertion tools may have a relatively low coefficient of friction to the adjacent materials of the chassis and thereby facilitate the insertion of the replaceable core component. Once it is inserted into the insertion pocket 260, the insertion tool 270 may be used to exert an insertion force in the direction indicated by the arrow 320 to insert the replaceable core component into the chassis. Then, the insertion tool may be withdrawn from the chassis in the opposing direction indicated by the arrow 321.

Such an insertion tool preferably has a planar surface area that is sufficiently large to aid in preventing the wrinkling or folding of the absorbent layer or layers of the replaceable core component during its insertion. To this end, the insertion tool preferably has a planar surface area of at least about 25% of the planar surface area of the replaceable core component. More preferably, the insertion tool has a planar surface area of at least about 50% or, most preferably, at least about 75%, of the planar surface area of the replaceable core component. The insertion tool may also be shaped to spread the replaceable core component and thereby prevent its wrinkling or folding during insertion. For example, as shown in the figures, the portion of the insertion tool adjacent to its inner end 318 is sized and shaped to conform to the tapered shape of the inner end segment of the absorbent layer 34 of the back panel 30.

Alternatively, the insertion tool may be releasably attached to the replaceable core component in a manner that is suitable for the effective insertion of the replaceable core component into the chassis. In such an embodiment, after the replaceable core component is inserted, the insertion tool may be released from the replaceable core component as the insertion tool is withdrawn from the chassis, as shown in FIG. 94, and FIG. 95. For example, the insertion tool 270 may be affixed adjacent to its inner end 318 to an intermediate member 315 in a first area of joining 316 and the replaceable core component may be joined to the intermediate member in a second area of joining 317 so as to be peelably releasable. In such an embodiment, the intermediate member may be disposed such that the intermediate member is subjected to a tensile force and the first area of joining and the second area of joining are subjected to substantially only a shear force as the insertion tool is used to apply an insertion force in the direction indicated by the arrow 320 to insert the replaceable core component into the chassis. Then, when the insertion tool is withdrawn from the chassis in the direction indicated by the arrow 321, the second area of joining is subjected to a peel force such that the intermediate member is released from the replaceable core component, while remaining affixed to the insertion tool and thereby being withdrawn with the insertion tool.

As another example, the insertion tool 270 may be joined adjacent to its inner end 318 to the intermediate member 315 in the first area of joining 316 so as to be peelably releasable and the replaceable core component may be affixed to the intermediate member in the second area of joining 317. In such an embodiment, the intermediate member may be similarly subjected to a tensile force and the first area of joining and the second area of joining may similarly be subjected to substantially only a shear force as the insertion tool is used to apply a force in the direction 320 to insert the replaceable core component into the chassis. Then, when the insertion tool is withdrawn from the chassis in the direction indicated by the arrow 321, and the first area of joining is thereby subjected to a peel force, the insertion tool may be released from the intermediate member, which remains affixed to the replaceable core component.

Rather than being joined or attached to the replaceable core component either directly or through an intermediate member, the insertion tool may have one or more protuberances, such as angled teeth or hooks, that engage the layer forming the outer surface of the replaceable core component when the insertion tool is slid along the outer surface in a first direction, and that disengage or fail to engage when the insertion tool is slid along the outer surface in an opposing second direction. Alternatively, the insertion tool may engage such protuberances on the outer surface of the replaceable core component. In either configuration, the movement of the insertion tool in the first direction applies an insertion force to the replaceable core component, while the movement of the insertion tool in the second direction disengages the insertion tool from the replaceable core component, thus leaving the replaceable core component in the inserted position. A surface of the insertion tool having a directional coefficient of friction relative to the outer surface layer of the replaceable core component may perform the same function as the protuberance by providing greater resistance when slid along the outer surface of the replaceable core component in the insertion direction and lesser resistance when withdrawn in the opposing direction.

In some embodiments, the extensible covering layer 300 shown in FIG. 35, FIG. 36, FIG. 37, and FIG. 38 may serve as the intermediate member 315 that remains attached to the replaceable core component after the withdrawal of the insertion tool. In such an embodiment, the extensible covering layer 300/intermediate member 315 may be releasably attached to the insertion tool for the insertion of the replaceable core component into the absorbent article. As the insertion tool is withdrawn, the extensible covering layer/intermediate member may be released from the insertion tool and attached to the chassis, as shown in FIG. 35 and FIG. 37. For example, in some embodiments, the extensible covering layer/intermediate member may be releasably attached to the insertion tool by releasable attachment means 302, which may be exposed by the withdrawal of the insertion tool and may then become attached to the chassis. In other embodiments, a second releasable attachment means disposed on the surface of the extensible covering layer/intermediate member opposite the releasable attachment means 302 may be exposed by the withdrawal of the insertion tool and may then become attached to the chassis. Similarly, a releasable attachment means having directional characteristics may be disposed adjacent to the releasable attachment of the extensible covering layer/intermediate member to the insertion tool. Such a directional releasable attachment means may not engage the chassis when moved in the insertion direction, but may engage the chassis when the insertion tool is removed. When the replaceable core component is subsequently removed from the chassis, the extensible covering layer may remain attached to the chassis, so as to extend to cover the outer surface of the replaceable core component as shown in FIG. 36 and FIG. 38, and then may be released from the chassis.

Figure 88:
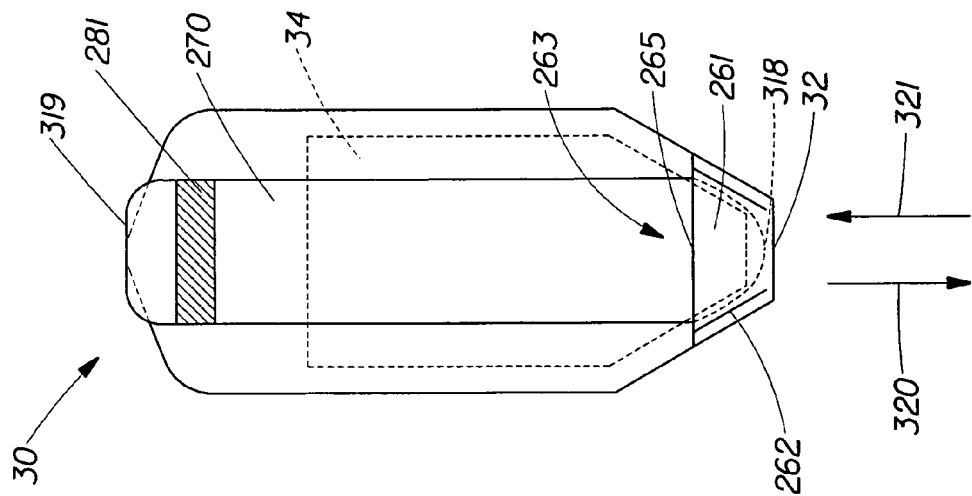
FIG. 88 is a plan view showing a replaceable absorbent core component having another insertion tool disposed in an insertion pocket.
Figure 87:
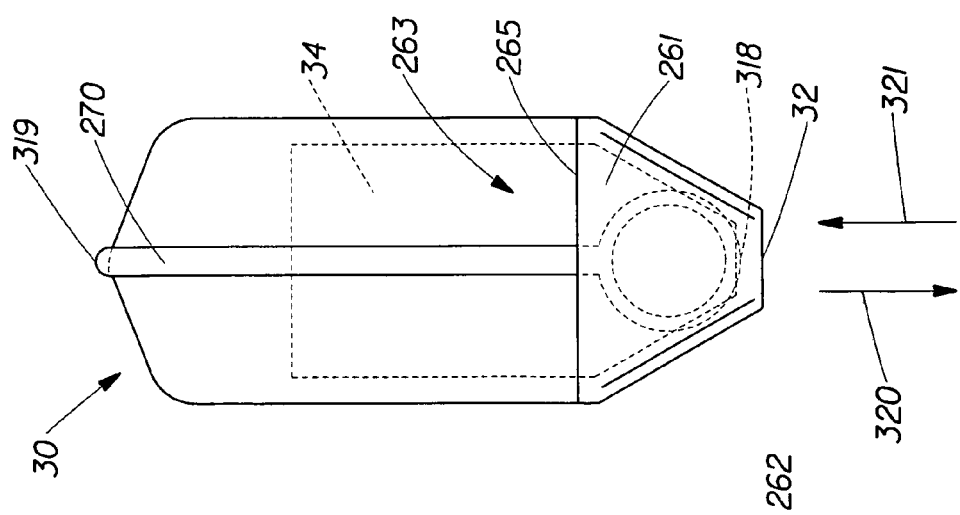
FIG. 87 is a plan view showing a replaceable absorbent core component having an insertion tool disposed in an insertion pocket.
Figure 90:
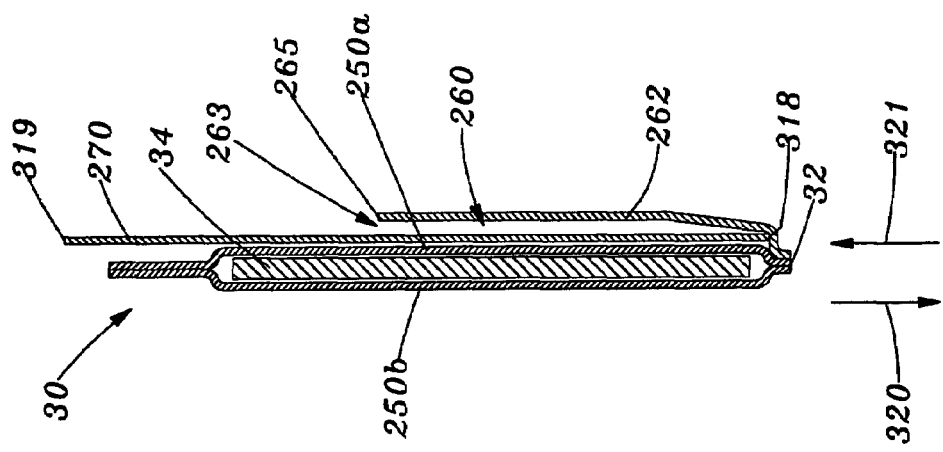
FIG. 90 is a partial section view showing the replaceable absorbent core component of FIG. 89.
Figure 89:
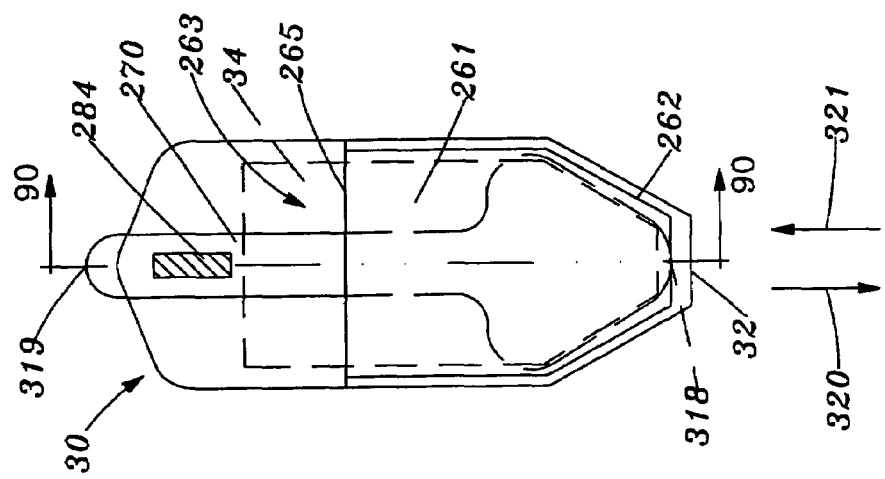
FIG. 89 is a plan view showing a replaceable absorbent core component having another insertion tool disposed in an insertion pocket.
Figure 92:
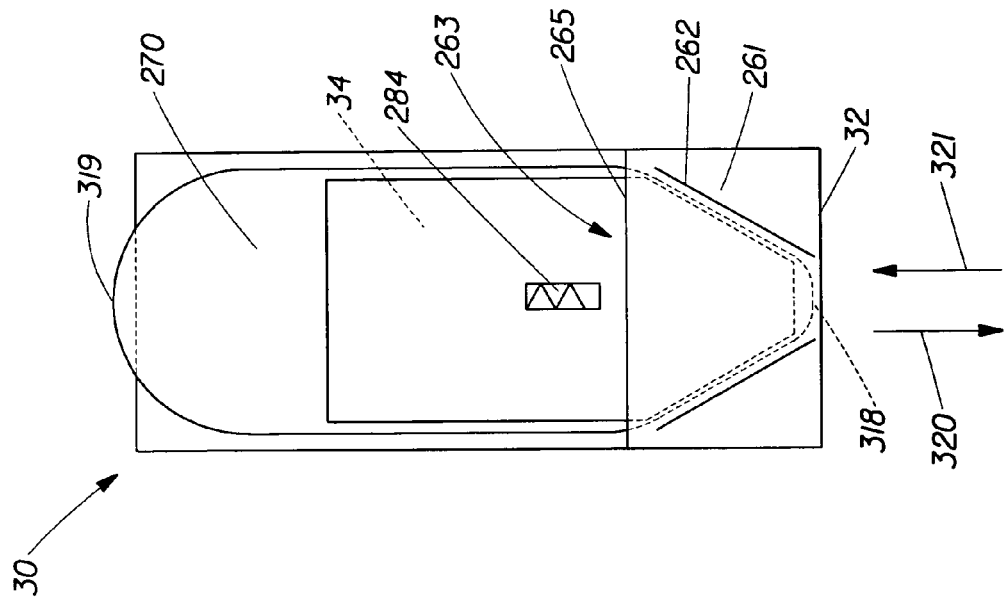
FIG. 92 is a plan view showing a replaceable absorbent core component having a rectangular inner end and having another insertion tool disposed in an insertion pocket.
Figure 91:
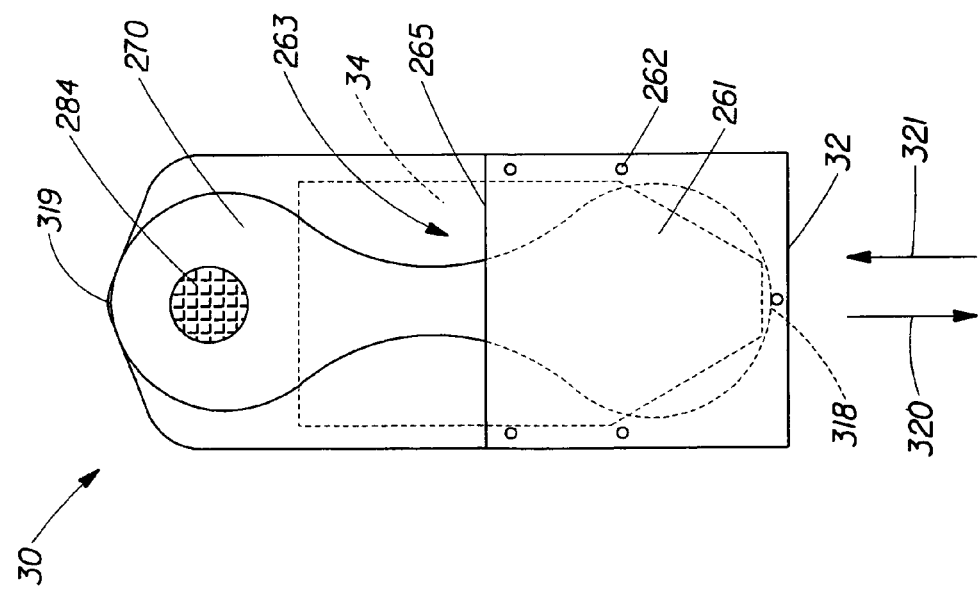
FIG. 91 is a plan view showing a replaceable absorbent core component having a rectangular inner end and having another insertion tool disposed in an insertion pocket.

The insertion tool may include an insertion depth indicator to provide an indication when a predetermined position of the insertion tool corresponding to a predetermined position of the replaceable core component relative to the chassis is reached. In general, the insertion tool may include any of the forms of an insertion depth indicator described with regard to the replaceable core component. For example, as shown in FIG. 88, the insertion depth indicator may include a visible indicator such as a line 281 positioned adjacent to the outer end 319 of the insertion tool such that the line is aligned with the waist end edge of the chassis when the predetermined position is reached. In another example of a visible insertion depth indicator, a graphical object on the insertion tool may align with an adjacent graphical object on the chassis to form a composite graphical object when the predetermined position is reached, similarly to the way in which a similar graphical object on the replaceable core component is herein described as aligning.

The insertion tool's insertion depth indicator may include a mechanical indicator providing tactile feedback in some exemplary embodiments. For example, as shown in FIG. 89, FIG. 90, FIG. 91, and FIG. 92, the insertion depth indicator of the insertion tool may include a mechanical insertion depth indicator 284 in the form of a mechanical surface fastener such as either a hook or a loop member disposed on the insertion tool and adapted to engage a complementary member disposed on the chassis, or to engage a non-woven surface of the chassis, when the predetermined position is reached. In another example of a mechanical insertion depth indicator, an outer surface of the insertion tool may have a relatively higher coefficient of friction to a portion of an adjacent surface of the chassis, such that when the predetermined position is reached, an increase in the coefficient of friction markedly increases the force required to slide the insertion tool farther and, thus, to insert the replaceable core component beyond the predetermined position. In addition, such a mechanical insertion depth indicator may simultaneously serve as both an insertion depth indicator and a location stabilizer, in embodiments in which the insertion tool remains in the chassis with the replaceable core component.

In some exemplary embodiments, an outer surface of the insertion tool may have a directional coefficient of friction relative to the adjacent surfaces of the chassis and thereby provide tactile feedback related to whether or not the insertion tool and the replaceable core component are being inserted in the intended end-to-end orientation. In general, the insertion tool may include any of the forms of such surfaces having directional coefficients of friction described with regard to the replaceable core component. For example, a material forming the surface of the insertion tool and having directional frictional characteristics may be oriented such that when the inner end of the insertion tool is inserted first, the coefficient of sliding friction is relatively low, thus making the insertion of the insertion tool and the replaceable core component into the chassis relatively easy. On the other hand, if the insertion of an inverted insertion tool, i.e., an insertion tool oriented such that its outer end is being inserted first, is attempted, a relatively higher coefficient of sliding friction of the directional material may provide a higher resistive force and, thus, make the insertion of the inverted insertion tool and replaceable core component into the chassis relatively more difficult. This directional frictional surface material may be disposed on one or more of the major surfaces of the insertion tool or may be disposed on laterally opposing edge surfaces.

In some exemplary embodiments, opposing outer surfaces of the insertion tool may have different coefficients of friction relative to the adjacent surfaces of the chassis and thereby provide tactile feedback related to whether or not the insertion tool and the replaceable core component are being inserted in the intended orientation of the replaceable core component's predetermined wearer-facing and garment-facing surfaces. For example, a material forming the wearer-facing surface of the insertion tool and having directional frictional characteristics may be oriented such that when the insertion tool is inserted with its predetermined wearer-facing surface oriented toward the wearer-facing layer of the chassis and with its predetermined garment-facing surface oriented toward the garment-facing layer of the chassis, the coefficient of sliding friction is relatively low, thus making the insertion of the insertion tool and the replaceable core component into the chassis relatively easy. On the other hand, if the insertion of a reversed insertion tool, i.e., an insertion tool oriented such that its wearer-facing and garment-facing surfaces are reversed from its intended orientation, is attempted, a relatively higher coefficient of sliding friction of the directional material may provide a higher resistive force and, thus, make the insertion of the reversed insertion tool and replaceable core component into the chassis relatively more difficult.

Figure 96:
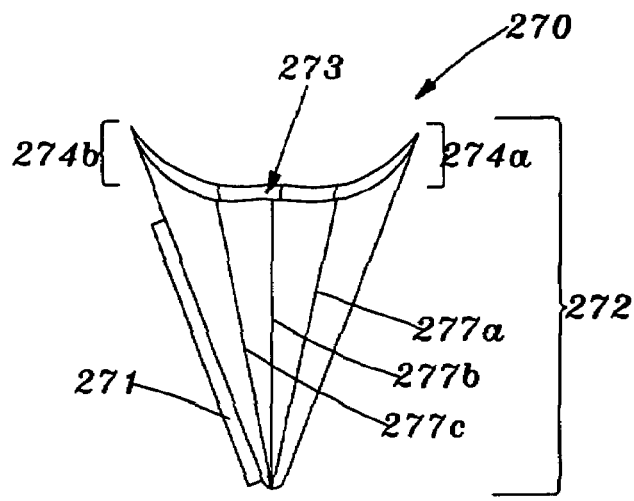
FIG. 96 is a side elevation view showing an insertion tool formed by a card-like element attached to a bag-like element.

The insertion tool may include a planar card-like element 271, as shown in FIG. 96. In order to be suitably thin and have a planar surface area that is sufficiently large to aid in preventing the wrinkling or folding of the replaceable core component during its insertion, this card-like element preferably has a relatively high ratio of its average width to its average thickness. For example, the card-like element may have an average width to average thickness ratio of at least 25:1. Preferably, the card-like element may have an average width to average thickness ratio of at least about 50:1 and, more preferably, at least about 100:1 and, most preferably, at least about 300:1. In some embodiments, the insertion tool may include two such planar card-like elements in a superposed configuration that are separable from each other along at least a portion of the perimeter of one or both of the superposed planar card-like elements. The planar card-like element may provide the desired stiffness to facilitate the insertion of the replaceable core component into the chassis. In embodiments in which the layers forming the insertion pocket of the replaceable absorbent core component and/or the layers forming the openable chassis pocket into which the replaceable core component is being inserted provide a constraining force tending to prevent the deflection of the replaceable core component and the insertion tool from a smooth plane or curved planar shape during the insertion process, this constraining force may lessen the required stiffness of the insertion tool.

Figure 97:
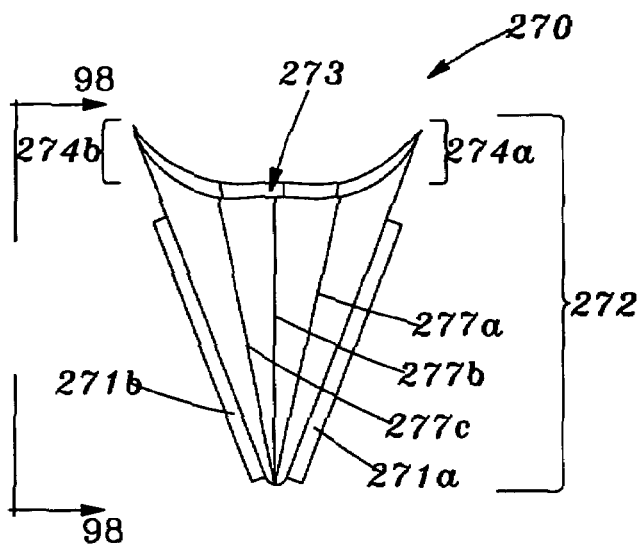
FIG. 97 is a side elevation view showing an insertion tool formed by two card-like elements attached to a bag-like element.
Figure 98:
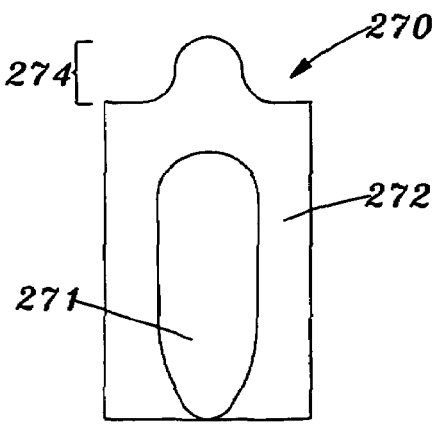
FIG. 98 is an elevation view showing one major surface of the insertion tool of FIG. 97.

Such an insertion tool may also include a bag-like element 272 forming an openable insertion tool pocket 273, as shown in an open state in FIG. 96. The bag like element may be joined to one side of the planar card-like element, as in FIG. 96, or alternatively, the bag-like element may be disposed between and joined to two planar card-like elements, as shown in FIG. 97. The bag-like element may be made of an extensible sheet material or may be formed of a sheet having folds or pleats 277 so as to be expandable for opening. The openable insertion tool pocket 273 may be of sufficient size to accept and retain a replaceable core component. Thus, the openable insertion tool pocket may be used to contain an unused replaceable core component prior to use or to accept and contain a used replaceable core component for disposal. The bag-like structure of the insertion tool may include a closure means, such as a tie-style closure that may include one or more closure tabs 274, as shown in FIG. 98, a drawstring closure, a mechanical fastener, a zipper, a button, a snap, an adhesive closure, or another closure means known in the art. In embodiments in which the unused replaceable core component is disposed inside the openable insertion tool pocket, this closure means may be used to secure the replaceable core component inside the pocket prior to its insertion into the absorbent article. This closure means may also be used to secure a used replaceable core component inside the openable insertion tool pocket after its removal from the absorbent article.

Figure 100:
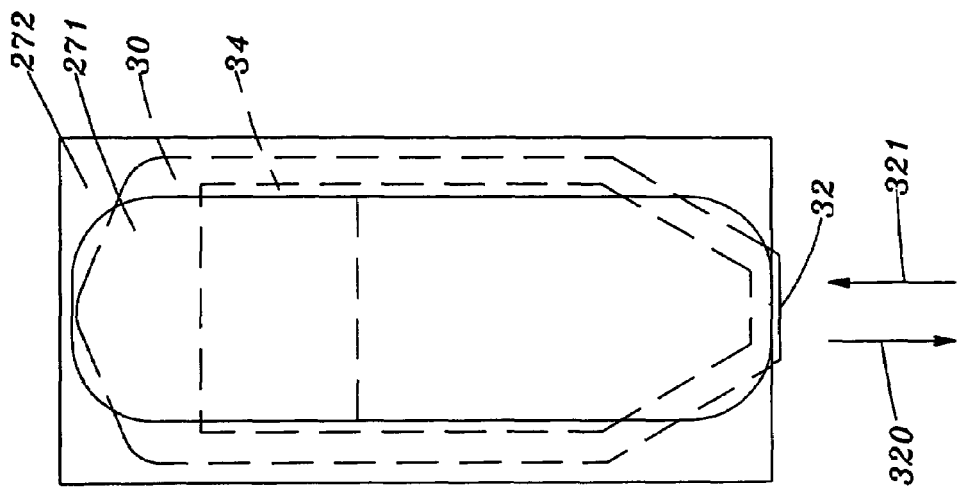
FIG. 100 is a plan view showing one major surface of the insertion tool of FIG. 99 containing the replaceable absorbent core component.
Figure 99:
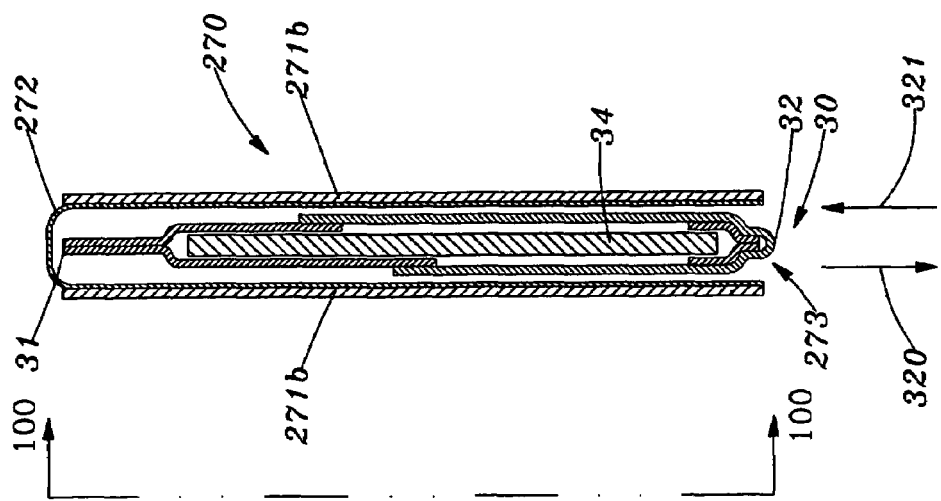
FIG. 99 is a partial section view showing a replaceable absorbent core component disposed inside an insertion tool pocket in an insertion tool configured for insertion.

In some embodiments, an insertion tool having the form of a card-like element 271 and an attached bag-like element 272 may be inserted into an insertion pocket of a replaceable core component and used in the manner described to exert an insertion force. Also, in some embodiments, as shown in FIG. 99 and FIG. 100, a replaceable core component, such as back panel 30, may be disposed inside the openable insertion tool pocket 273 prior to its insertion into the absorbent article. In such an embodiment, the insertion tool containing the replaceable core component inside its openable insertion tool pocket may be inserted into the absorbent article and then withdrawn, thereby leaving the replaceable core component in the absorbent article. When used in this manner, the card-like element and/or the bag-like element of the insertion tool may act as a barrier preventing the exposure of the replaceable core component, for example, to the hand of a caregiver inserting the replaceable core component into the absorbent article or to potential contaminants prior to its insertion into the absorbent article.

In some embodiments, a replaceable core component including the extensible covering layer 300 shown in FIG. 35 and FIG. 36 may be disposed inside the openable insertion tool pocket 273, as shown in FIG. 99, for insertion into the absorbent article. In such an embodiment, the releasable attachment means 302 may serve to attach the extensible covering layer 300 to the insertion tool in the first area of joining 316 so as to be peelably releasable. As the insertion tool is withdrawn, it may be peelably released from the extensible covering layer 300 and the releasable attachment means 302 may become exposed and attached to the chassis, as shown in FIG. 35. When the replaceable core component is subsequently removed from the chassis, the extensible covering layer may remain attached to the chassis, so as to extend to cover the outer surface of the replaceable core component as shown in FIG. 36, and then may be released from the chassis.

The insertion tool may have a substantially planar portion having a generally uniform thickness and a portion adjacent to its inner end having a greater thickness and thereby serving as a "plow" to separate the separable layers of the chassis as the insertion tool in inserted into the absorbent article. The greater thickness 276 of the insertion tool in the end portion, relative to the generally uniform thickness 275 in the planar portion, may be formed by folding the inner end 318 of the insertion tool 270 upon itself, for example as shown in FIG. 101 and FIG. 102, by forming a bend in the inner end, for example as in FIG. 103 and FIG. 104, by adding a layer to the inner end, for example as in FIG. 105 and FIG. 106, or by simply forming the inner end of the insertion tool with a greater planar thickness. The greater thickness of the insertion tool in the end portion may be at least about 5 times the generally uniform thickness in the substantially planar portion and is, preferably, at least about 10 times or, more preferably, at least about 20 times the generally uniform thickness. In some embodiments, the insertion tool may include a resilient element 278 serving to make the relatively thicker region elastically compressible and thereby facilitate the use of the insertion tool by allowing it to resiliently conform as it is inserted into an insertion pocket and as it is used to exert a force to insert a replaceable core component into a chassis.

In embodiments in which the openable chassis pocket and the replaceable core component are "keyed" to each other, so as to prevent the insertion of the replaceable core component in any orientation other than a predetermined orientation contemplated in the design of the replaceable core component, the insertion tool may be correspondingly keyed to the openable chassis pocket and the replaceable core component. Thus, the openable chassis pocket may be shaped and the insertion tool may be correspondingly shaped to fit within the shaped openable chassis pocket.

For example, in embodiments described in detail elsewhere in this disclosure, the openable chassis pocket may include a separator that bifurcates or partitions the openable chassis pocket into at least two connected branches. In embodiments having such a bifurcated openable chassis pocket, the insertion tool may include a cooperative structure that permits the insertion of its inner end beyond the outer end of the separator, i.e., to a point farther from the waist end edge than the outer end of the separator. Such a cooperative structure 227 in the insertion tool may include a slit, a slot, or a groove formed in the insertion tool, as shown in FIG. 107, for receiving and/or bypassing the separator. The separator in the openable chassis pocket may be formed along the longitudinal centerline 17 of the chassis and the cooperative structure in the insertion tool may be formed so as to coincide with the longitudinal centerline 25 of the replaceable core component or, alternatively, either the separator or the cooperative structure, or both, may be offset from the respective longitudinal centerline, as in FIG. 107. Similarly to the manner described with regard to the cooperative structure in the replaceable core component, such an offset configuration may serve to ensure that the insertion tool is inserted with its inner end in the crotch region and its outer end in the waist region and is inserted in a predetermined lateral position, thereby ensuring that the replaceable core component being inserted with the insertion tool is inserted with its liquid pervious surface region in a predetermined longitudinal and/or lateral position, and so on.

As shown in FIG. 108, in embodiments in which the openable chassis pocket is divided into several separate connected branches or non-interconnected sections, i.e., divided effectively into separate openable chassis pockets, the insertion tool may have a corresponding number of protruding finger-like sections 279. These finger-like sections may be placed into the branches or sections of the openable chassis pocket in a side-by-side lateral relationship and, thus, may be used to insert a correspondingly shaped replaceable core component or to insert multiple replaceable core component into the respective branches or sections.

In embodiments including more than one shaping element, as well as shaping elements other than a separator, the insertion tool may be correspondingly shaped. For example, a shaping element may include a slot into which a corresponding "key" fits in only a predetermined orientation, one or more holes or depressions into which one or more corresponding pins, bosses, or protuberances fits in only a predetermined orientation, a partition within the openable chassis pocket that requires the insertion tool to be partially inserted and then rotated and/or translated in order for the insertion to be completed, and similar configurations.

Those skilled in the art will recognize that additional exemplary embodiments of absorbent articles providing access to a removable and replaceable absorbent core component or absorbent insert are possible without departing from the scope of the present invention. Furthermore, it is contemplated that, without departing from the scope of the present invention, additional combinations of the absorbent core components, the absorbent core members, the placement of the absorbent core components and members, and the absorptive characteristics may be used, with the desired functional requirements influencing the ultimate design. Specifically, not only the illustrated embodiments, but all structurally feasible combinations of the disclosed elements and configurations are contemplated. Also, methods of use of the disposable absorbent articles of the present invention in which the replaceable core component is removed, inserted, and/or replaced are contemplated. In addition, articles of commerce, such as packages, bags, containers, display packs, and the like, in which the disposable absorbent articles of the present invention are included with instructions for their use are likewise contemplated.

While particular exemplary embodiments of the present invention have been illustrated and described, it would be obvious to those skilled in the art that various other changes and modifications can be made without departing from the spirit and scope of the present invention. The foregoing is therefore intended to cover in the appended claims all such changes and modifications that are within the scope of the present invention.

What is claimed is:

1. A disposable absorbent article adapted to be worn about a lower torso of a human body, comprising:
   a chassis forming a waist opening and a pair of leg openings and having longitudinally opposing first and second waist end edges, longitudinally opposing first and second waist regions adjacent to the respective waist end edges, and a crotch region longitudinally intermediate of the waist regions;
   a non-removable absorbent core component disposed in the crotch region; and
   a first replaceable absorbent core component disposed in capillary liquid communication with the non-removable absorbent core component and having a major surface having a liquid permeable region and a liquid impermeable region, the first replaceable absorbent core component having an outer distal end and an inner proximal end disposed relatively nearer the crotch region than the outer distal end, at least a portion of the liquid impermeable region extending longitudinally from the outer distal end toward the inner proximal end and at least a portion of the liquid permeable region being disposed longitudinally between the portion of the liquid impermeable region and the inner proximal end.

2. The disposable absorbent article of claim 1 wherein the first replaceable absorbent core component extends from the crotch region beyond a waist end edge of the first waist region.

3. The disposable absorbent article of claim 1 wherein the first replaceable absorbent core component comprises an openable insertion pocket having an openable end facing away from the inner proximal end.

4. The disposable absorbent article of claim 1 wherein the first replaceable absorbent core component comprises an insertion depth indicator adapted to provide an indication when a predetermined depth of insertion of the first replaceable absorbent core component into the chassis is reached.

5. The disposable absorbent article of claim 4 wherein the insertion depth indicator comprises a mechanical indicator comprising a mechanical fastener adapted to engage a surface of the chassis when the predetermined position is reached.

6. The disposable absorbent article of claim 1 comprising an openable chassis pocket formed by the chassis and having a shape, wherein the first replaceable absorbent core component has a shape corresponding to the shape of the openable chassis pocket and allowing the first replaceable absorbent core component to be inserted into the shaped openable chassis pocket in only a predetermined orientation.

7. The disposable absorbent article of claim 1 wherein the first replaceable absorbent core component comprises a location stabilizer releasably attached to the chassis in a waistband region.

8. The disposable absorbent article of claim 1 wherein the first replaceable absorbent core component has a generally planar body comprising longitudinally successive first, second, third, and fourth segments defined by respective quarters of its length, the first segment including the inner proximal end and having an area less than an area of any one of the second, third, and fourth segments, and the fourth segment including the outer distal end and having an area less than at least one of the second segment and the third segment.

9. The disposable absorbent article of claim 1 wherein the outer distal end is shaped to form an integral pull tab for removal of the first replaceable absorbent core component from the absorbent article.

10. The disposable absorbent article of claim 1 wherein the first replaceable absorbent core component comprises a multi-piece absorbent structure.

11. The disposable absorbent article of claim 1 wherein the non-removable absorbent core component comprises a first absorbent layer extending from the first waist region into and ending in the crotch region and a second absorbent layer extending from the second waist region into and ending in the crotch region.

12. The disposable absorbent article of claim 1 wherein the chassis comprises a first extensible waistband disposed in the first waist region and a second extensible waistband disposed in the first waist region, the second extensible waistband being disposed in a layered configuration with the first extensible waistband.

13. The disposable absorbent article of claim 12 wherein the chassis has a wearer-facing layer and a garment-facing layer and the first extensible waistband is attached to the wearer-facing layer, and the second extensible waistband is attached to the garment-facing layer.

14. The disposable absorbent article of claim 13 wherein the first extensible waistband and the second extensible waistband are separable for access into an openable chassis pocket formed by and between the wearer-facing layer and the garment-facing layer.

15. The disposable absorbent article of claim 14 wherein a portion of the first extensible waistband is unattached to the wearer-facing layer.

16. The disposable absorbent article of claim 1 wherein the chassis comprises a first extensible waistband disposed in the first waist region and a second extensible waistband disposed in the first waist region relatively nearer the crotch region than the first extensible waistband.

17. The disposable absorbent article of claim 1 wherein the chassis comprises an extensible waistband disposed in the first waist region and including a first portion and a second portion independently extensible from the first portion disposed relatively nearer the crotch region than the first portion.

18. The disposable absorbent article of claim 1 wherein the chassis comprises a topsheet and a backsheet forming an openable chassis pocket having an openable end disposed in the first waist region, an extensible waistband attached to the topsheet adjacent to the openable end, and an extensible portion of the backsheet adjacent to the openable end.

19. The disposable absorbent article of claim 1 wherein the chassis comprises a topsheet and a backsheet forming an openable chassis pocket adapted to receive the first replaceable absorbent core component and the first replaceable absorbent core component is removably disposed inside the openable chassis pocket.

20. The disposable absorbent article of claim 1 wherein the chassis comprises a topsheet and a backsheet forming an openable chassis pocket adapted to receive the first replaceable absorbent core component, the first replaceable absorbent core component is removably disposed inside the openable chassis pocket, and the openable chassis pocket has an inner end located in the crotch region and formed by an area of joining of the topsheet and the non-removable absorbent core component, the backsheet and the non-removable absorbent core component, the topsheet and the backsheet and the non-removable absorbent core component, or the topsheet and the backsheet.

21. An article of commerce comprising a disposable absorbent article adapted to be worn about a lower torso of a human body, the absorbent article comprising:

a chassis forming a waist opening and a pair of leg openings and having longitudinally opposing first and second waist end edges, longitudinally opposing first and second waist regions adjacent to the respective waist end edges, and a crotch region longitudinally intermediate of the waist regions;

a non-removable absorbent core component disposed in the crotch region; and a first replaceable absorbent core component disposed in capillary liquid communication with the non-removable absorbent core component and having a planar surface having a liquid permeable region and a liquid impermeable region, the first replaceable absorbent core component having an outer end and an inner end disposed relatively nearer the crotch region than the outer end, at least a portion of the liquid impermeable region extending longitudinally from the outer end toward the inner end and at least a portion of the liquid permeable region being disposed longitudinally between the portion of the liquid impermeable region and the inner end, the article of commerce further comprising instructions for removing the first replaceable absorbent core component from the absorbent article, or inserting the first replaceable absorbent core component into the absorbent article, or inserting a like replacement of the first replaceable absorbent core component into the absorbent article, or replacing the first replaceable absorbent core component by removing the first replaceable absorbent core component from the absorbent article and inserting a like replacement of the first replaceable absorbent core component into the absorbent article.

22. The article of commerce of claim 21 wherein the first replaceable absorbent core component comprises an insertion pocket and the instructions include instructions for using the insertion pocket to insert the first replaceable absorbent core component into the absorbent article.

* * * * *